(12) United States Patent
May et al.

(10) Patent No.: US 9,688,972 B2
(45) Date of Patent: Jun. 27, 2017

(54) CRISPR HYBRID DNA/RNA POLYNUCLEOTIDES AND METHODS OF USE

(71) Applicant: PIONEER HI-BRED INTERNATIONAL. INC., Johnston, IA (US)

(72) Inventors: Andrew Paul May, San Francisco, CA (US); Paul Daniel Donohoue, Berkeley, CA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 0 days.

(21) Appl. No.: 15/408,920

(22) Filed: Jan. 18, 2017

(65) Prior Publication Data

US 2017/0121694 A1  May 4, 2017

Related U.S. Application Data

(60) Continuation of application No. 15/238,464, filed on Aug. 16, 2016, now Pat. No. 9,580,701, which is a division of application No. 15/008,054, filed on Jan. 27, 2016, now Pat. No. 9,650,617.

(60) Provisional application No. 62/251,548, filed on Nov. 5, 2015, provisional application No. 62/108,931, filed on Jan. 28, 2015.

(51) Int. Cl.
| | | |
|---|---|---|
| *C12Q 1/68* | (2006.01) | |
| *C12N 15/60* | (2006.01) | |
| *C12N 15/63* | (2006.01) | |
| *C12N 15/11* | (2006.01) | |
| *C12N 9/22* | (2006.01) | |

(52) U.S. Cl.
CPC .............. *C12N 9/22* (2013.01); *C12Y 301/00* (2013.01)

(58) Field of Classification Search
CPC .... C12N 15/111; C12N 15/63; C12N 15/902; C12N 2310/10; C12N 2320/51; C12N 2320/53; C12N 9/16; C12N 9/22; C12Q 1/6827; C12Y 301/00
See application file for complete search history.

(56) References Cited

U.S. PATENT DOCUMENTS

| | | | |
|---|---|---|---|
| 8,697,359 B1 | 4/2014 | Zhang | |
| 8,771,945 B1 | 7/2014 | Zhang | |
| 8,795,965 B2 | 8/2014 | Zhang | |
| 8,865,406 B2 | 10/2014 | Zhang et al. | |
| 8,871,445 B2 | 10/2014 | Cong et al. | |
| 8,889,356 B2 | 11/2014 | Zhang | |
| 8,889,418 B2 | 11/2014 | Zhang et al. | |
| 8,895,308 B1 | 11/2014 | Zhang et al. | |
| 8,906,616 B2 | 12/2014 | Zhang et al. | |
| 8,932,814 B2 | 1/2015 | Cong et al. | |
| 8,945,839 B2 | 2/2015 | Zhang | |
| 8,993,233 B2 | 3/2015 | Zhang et al. | |
| 8,999,641 B2 | 4/2015 | Zhang et al. | |
| 2014/0068797 A1 | 3/2014 | Doudna et al. | |
| 2014/0170753 A1 | 6/2014 | Zhang | |
| 2014/0179006 A1 | 6/2014 | Zhang | |
| 2014/0179770 A1 | 6/2014 | Zhang et al. | |
| 2014/0186843 A1 | 7/2014 | Zhang et al. | |
| 2014/0186919 A1 | 7/2014 | Zhang et al. | |
| 2014/0186958 A1 | 7/2014 | Zhang et al. | |
| 2014/0189896 A1 | 7/2014 | Zhang et al. | |
| 2014/0227787 A1 | 8/2014 | Zhang | |
| 2014/0234972 A1 | 8/2014 | Zhang | |
| 2014/0242664 A1 | 8/2014 | Zhang et al. | |
| 2014/0242699 A1 | 8/2014 | Zhang | |
| 2014/0242700 A1 | 8/2014 | Zhang et al. | |
| 2014/0248702 A1 | 9/2014 | Zhang et al. | |
| 2014/0256046 A1 | 9/2014 | Zhang et al. | |
| 2014/0273231 A1 | 9/2014 | Zhang et al. | |
| 2014/0273232 A1 | 9/2014 | Zhang et al. | |
| 2014/0273234 A1 | 9/2014 | Zhang et al. | |
| 2014/0310830 A1 | 10/2014 | Zhang et al. | |
| 2014/0335620 A1 | 11/2014 | Zhang et al. | |
| 2014/0357530 A1 | 12/2014 | Zhang et al. | |
| 2015/0059010 A1 | 2/2015 | Cigan et al. | |
| 2015/0079681 A1 | 3/2015 | Zhang | |

FOREIGN PATENT DOCUMENTS

| | | |
|---|---|---|
| WO | WO-2011/143124 A2 | 11/2011 |
| WO | WO-2013/098244 A1 | 7/2013 |
| WO | WO-2013/141680 A1 | 9/2013 |
| WO | WO-2013/142578 A1 | 9/2013 |
| WO | WO-2014/018423 A2 | 1/2014 |
| WO | WO-2014/093712 A1 | 6/2014 |
| WO | WO-2014/144761 A2 | 9/2014 |
| WO | WO-2014/150624 A1 | 9/2014 |

(Continued)

OTHER PUBLICATIONS

Houdebine, L., Journal of Biotechnology 98:145-160, 2002.*
Phillips, A., J. Pharm. Pharmacology 53:1169-1174, 2001.*
Gardlik et al., Med. Sci. Monit. 11(4):RA110-121, 2005.*
Briner et al., "Guide Rna Functional Modules Direct Cas9 Activity and Orthogonality," Molecular Cell (2014); 56:1-7. [online], <URL: http://dx.doi.org/10.1016/j.molcel.2014.09.019>.
Cong et al., "Multiplex Genome Engineering Using CRISP/CAS Systems," Science, (2013), 339(6121): 819-823.

(Continued)

*Primary Examiner* — Delia Ramirez

(74) *Attorney, Agent, or Firm* — Porzio, Bromberg & Newman P.C.

(57) ABSTRACT

The present disclosure provides DNA-guided CRISPR systems; polynucleotides comprising DNA, RNA and mixtures thereof for use with CRISPR systems; and methods of use involving such polynucleotides and DNA-guided CRISPR systems.

20 Claims, 16 Drawing Sheets

(56) References Cited

FOREIGN PATENT DOCUMENTS

WO    WO-2015/026885 A1    2/2015

OTHER PUBLICATIONS

Deltcheva et al., "CRISPR RNA maturation by trans-encoded small RNA and host factor RNase III," Nature, (2011); 471(7340):602-9.

Gasiunas et al., "Cas9-crRNA ribonucleoprotein complex mediates specific DNA cleavage for adaptive immunity in bacteria," PNAS, (2012); 109(39).

International Search Report and Written Opinion issued in International Application No. PCT/US2016/015145, mailed May 3, 2016.

Jinek et al., "Bacterial Immunity a Programmable Dual-RNA-Guided DNA Endonuclease in Adaptive," Science, (2012); 337:816-821.

Jinek et al., "Structures of Cas9 Endonucleases Reveal RNA-Mediated Conformational Activation," Science, (2014); 343: 1215, 1247997-1-1247997-11.

Mali et al., "RNA-Guided Human Genome Engineering via Cas9," Science, (2013); 339: 823-826.

Marakova et al. "An updated evolutionary classification of CRISPR-Cas systems," Nature Reviews Microbiology, [online] published Sep. 28, 2015; [retrieved on ]. Retrieved from the Internet: <URL: doi: 10.1038/nrmicro3569.>.

Nishimasu et al., "Crystal Structure of Cas9 in Complex with Guide RNA and Target DNA," Cell, (2014); 156: 935-949.

Ran et al., "In vivo genome editing using *Staphylococcus aureua* Cas9," Nature, (2015); 520(7546): 186-191.

Shmakov et al. " Discovery and Functional Characterization of Diverse Class 2 CRISPR-Cas Systems," Molecular Cell, (2015); 60(3): 385-397.

Svitashev et al., "Targeted Mutagenesis, Precise Gene Editing, and Site-Specific Gene Insertion in Maize Using Cas9 and Guide RNA," Plant Physiology, (2015); 169(2): 931-945.

Zetsche et al., "Cpf1 Is a Single RNA-Guided Endonuclease of a Class 2 CRISPR-Cas System," Cell, (2015); 163(3):759-71.

\* cited by examiner

|   | A   | B   | C   | D    |
|---|-----|-----|-----|------|
| 1 | n/d | n/d | 79% | 100% |
| 2 | n/d | n/d | 74% | 62%  |
| 3 | n/d | n/d | 84% | 80%  |
| 4 | n/d | n/d | 78% | 100% |
| 5 | n/d | n/d | 83% | 99%  |
| 6 | n/d | n/d | 24% | 100% |
| 7 | n/d | n/d | 74% | 60%  |
| 8 | n/d | n/d | 54% | 100% |

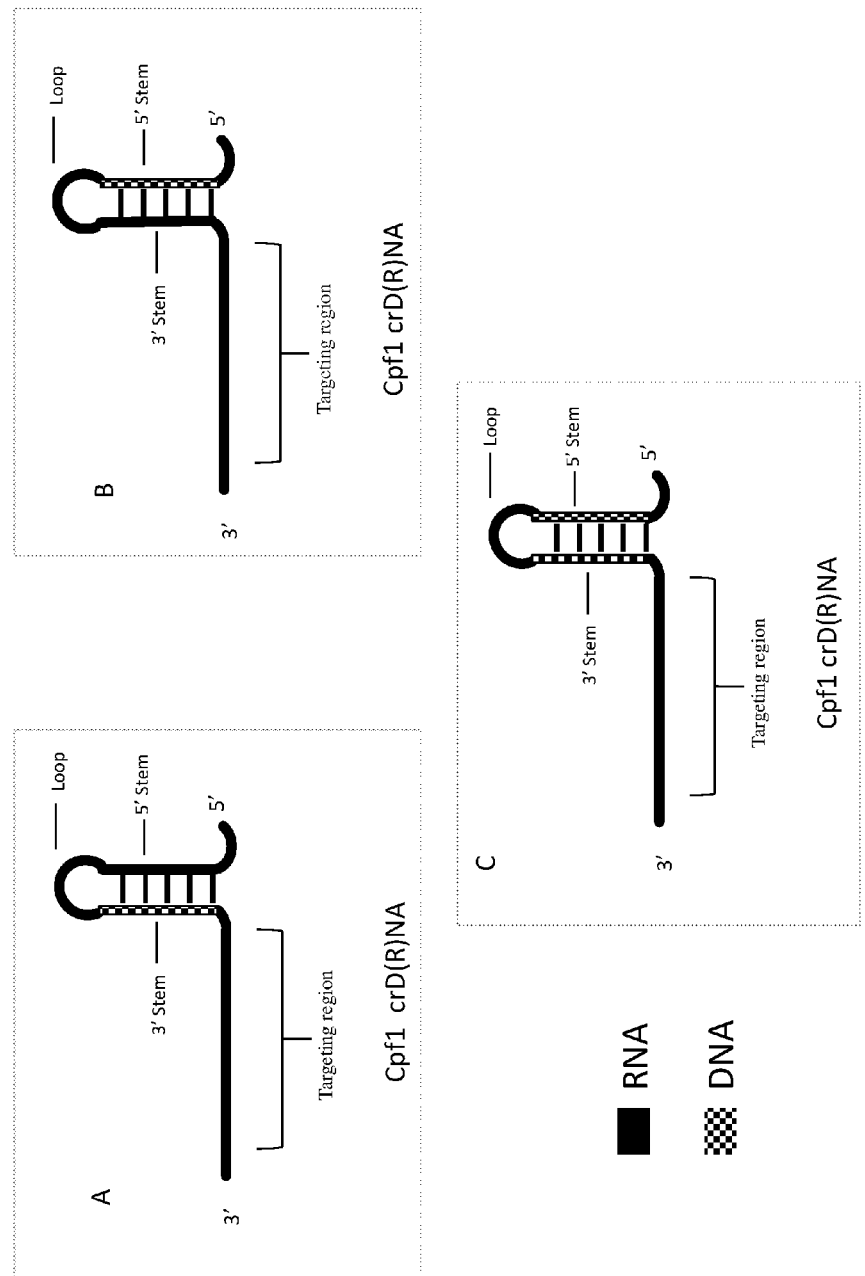
FIG. 10A-C

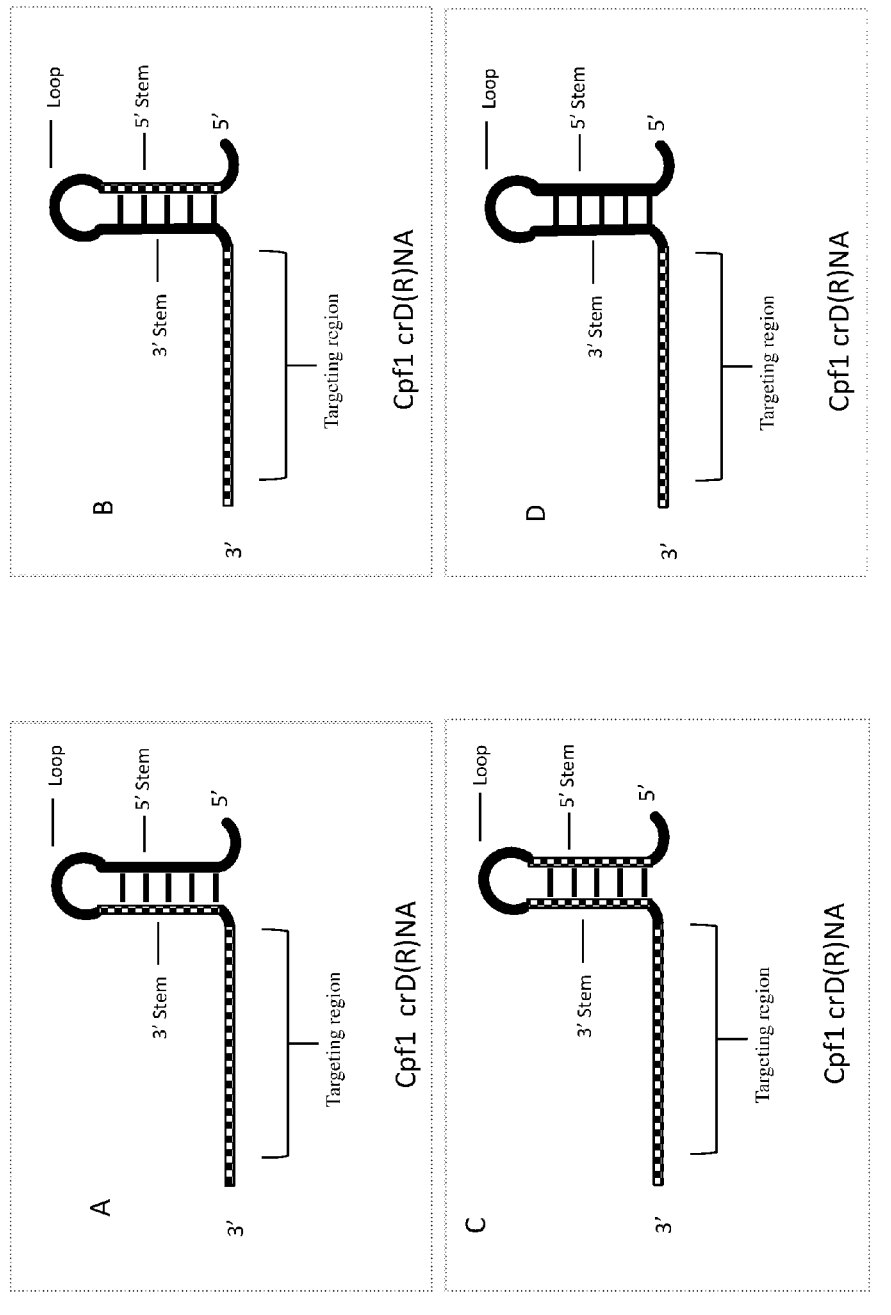
FIG. 11A-D

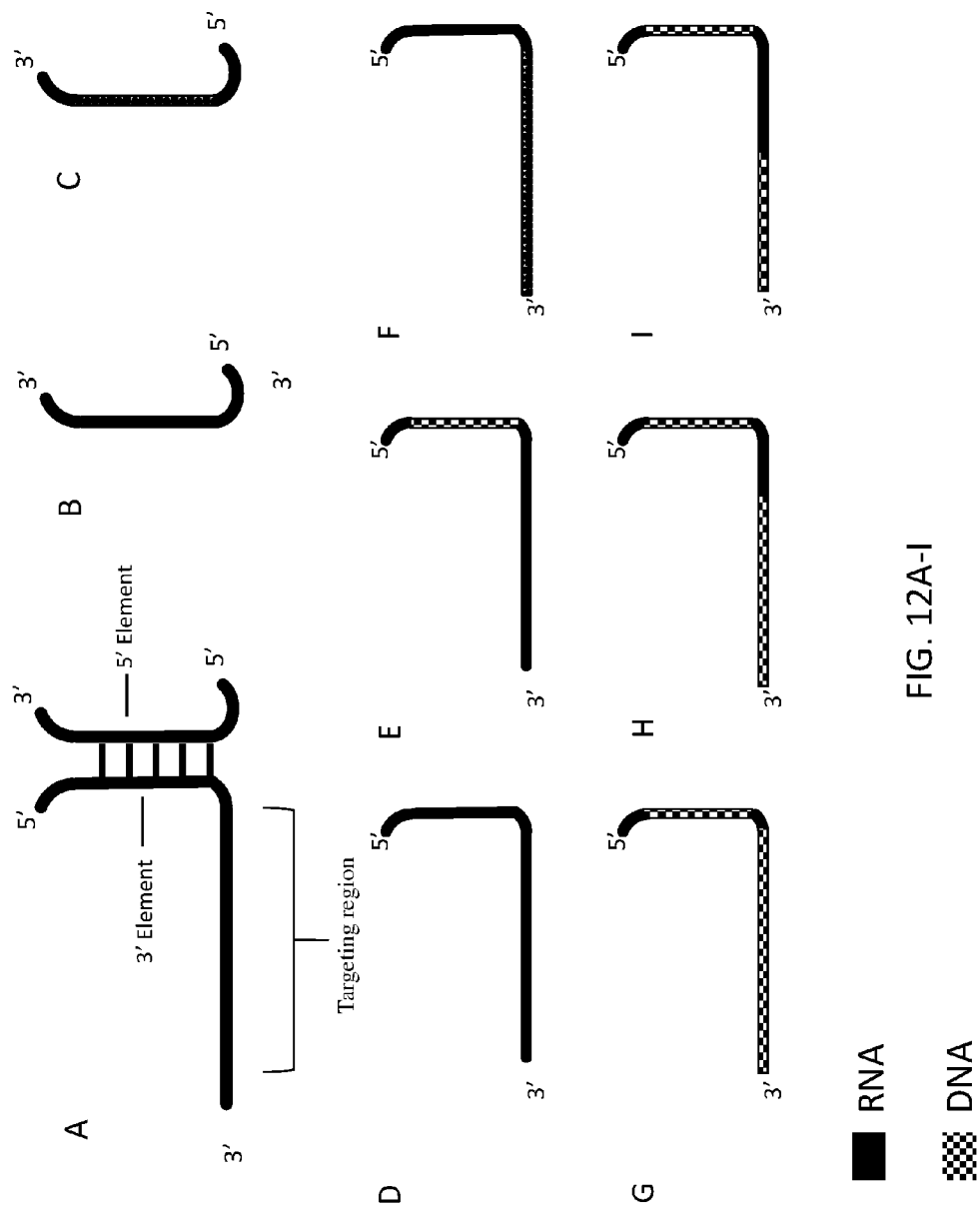
FIG. 12A-I

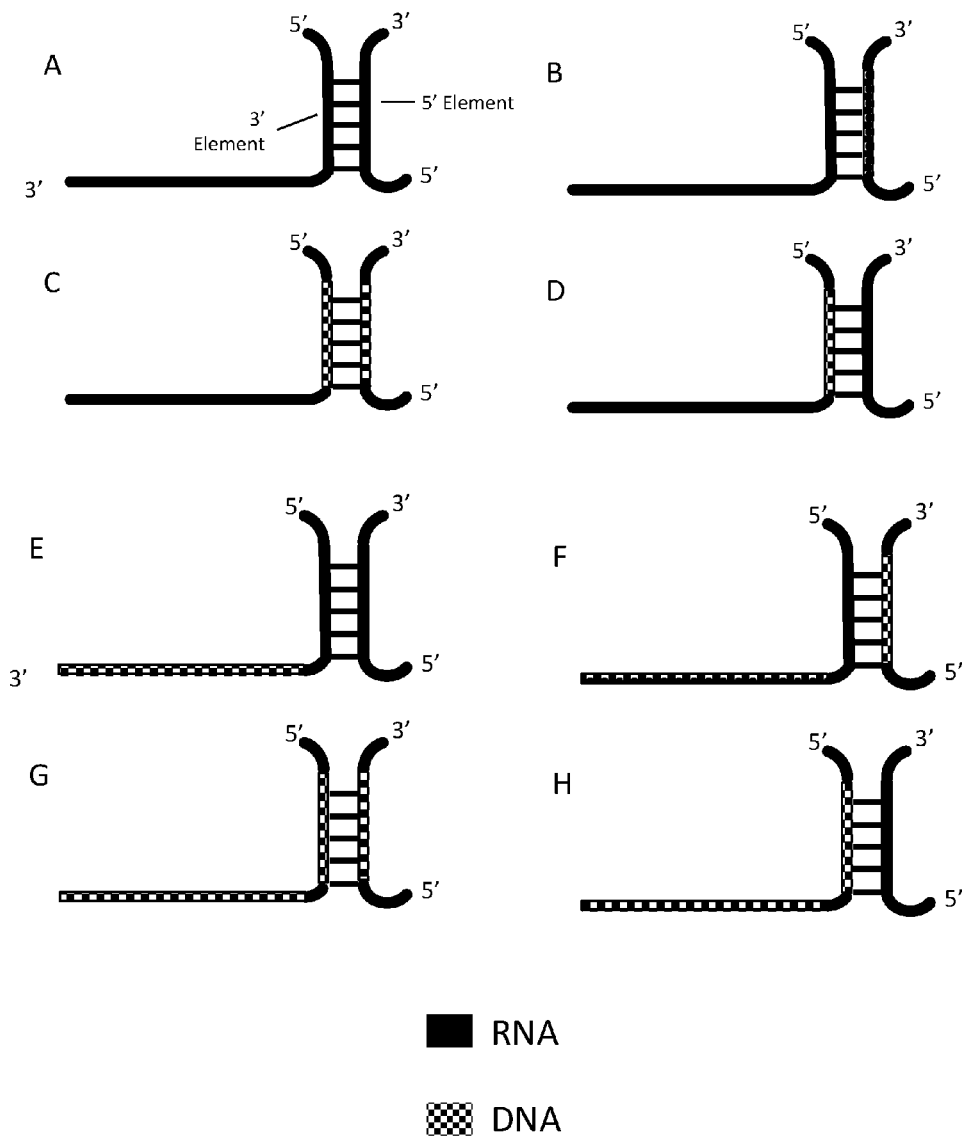
FIG. 13A-H

| | | Protospacer Target | Expected Site of Cleavage | Protospacer Adjacent Motif | SEQ ID NO: | Frequency in Treated | Frequency in Control |
|---|---|---|---|---|---|---|---|
| | Reference | CAGCGCACGTATATATACGCGTACGCGTACGT | ▼ | TGAGGTATATATATCCTCCGCCG | 216 | | |
| sgD(R)NA corresponding to SEQ ID NO.: 204 | Mutation 1 | CAGCGCACGTATATATACGCGTACGCGTACGT- | | TGAGGTATATATATCCTCCGCCG | 217 | 5 | 0 |
| sgD(R)NA corresponding to SEQ ID NO.: 205 | Mutation 1 | CAGCGCACGTATATATACGCGTACGCGTACGT<u>t</u>GTGAGGTATATATATCCTCCGCCG | | | 218 | 113 | 0 |
| | Mutation 2 | CAGCGCACGTATATATACGCGTACGCGTACG- | | GTGAGGTATATATATCCTCCGCCG | 219 | 62 | 0 |
| | Mutation 3 | CAGCGCAC------------------------- | | GTATATATATCCTCCGCCG | 220 | 12 | 0 |
| | Mutation 4 | CAGCGCACGTATATATACGCGTACGCGTACGT- | | TGAGGTATATATATCCTCCGCCG | 221 | 5 | 0 |
| sgD(R)NA corresponding to SEQ ID NO.: 206 | Mutation 1 | CAGCGCACGTATATATACGCGTACGCGTACGCGTA----TGAGGTATATATATCCTCCGCCG | | | 222 | 5 | 0 |
| | Mutation 2 | CAGCGCACGTATATATACGCGTACGCGTACGT- | | TGAGGTATATATATCCTCCGCCG | 223 | 4 | 0 |

FIG. 14A

| | Protospacer Target | Expected Site of Cleavage | Protospacer Adjacent Motif | SEQ ID NO: | Frequency in Treated | Frequency in Control |
|---|---|---|---|---|---|---|
| sgD(R)NA corresponding to SEQ ID NO.: 224 | | | | | | |
| Reference | AGTCCGCTGGCCGAGGTCGACTACCGCCGGTGAAGCAC | | | 234 | | |
| Mutation 1 | AGTCCCGCTGGCCGAGGTCGACTACCaGGGCCGGTGAAGCAC | | | 235 | 88 | 16 |
| Mutation 2 | AGTCCGCTGGCCGAGGTCGACTtgCCGGCCGGTGAAGCAC | | | 236 | 30 | 0 |
| Mutation 3 | AGTCCGCTGGCC---------------GGTGAAGCAC | | | 237 | 17 | 0 |
| Mutation 4 | AGTCCGCTGGCCGAGGTCGAC--caGGCCGGTGAAGCAC | | | 238 | 14 | 0 |
| Mutation 5 | AGTCCGCTGGCCGAGGTCGACTACCtGGCCGGTGAAGCAC | | | 239 | 12 | 0 |
| Mutation 6 | AGTCCGC----------------caGTGAAGCAC | | | 240 | 10 | 0 |
| Mutation 7 | AGTCCGCTGGCCGAGGTCGACTAC-GGCCGGTGAAGCAC | | | 241 | 10 | 0 |
| Mutation 8 | AGTCCGCTGGCCGAGGTCGACTACCGGCCGGTGAAGCAC | | | 242 | 9 | 0 |
| sgD(R)NA corresponding to SEQ ID NO.: 225 | | | | | | |
| Mutation 1 | AGTCCGCTGGCCGAGGTCGACTACCaGGGCCGGTGAAGCAC | | | 243 | 81 | 16 |
| Mutation 2 | AGTCCGCTGGCCG----------GTGAAGCAC | | | 244 | 27 | 0 |
| Mutation 3 | AGTCCGCTGGCCGAGGTCGACTAC-GGCCGGTGAAGCAC | | | 245 | 9 | 0 |
| Mutation 4 | AGTCCGCTGGCCGAGGTCGACT--tGGCCGGTGAAGCAC | | | 246 | 8 | 0 |
| sgD(R)NA corresponding to SEQ ID NO.: 226 | | | | | | |
| Mutation 1 | AGTCCGCTGGCCGAGGTCGACTACCaGGCCGGTGAAGCAC | | | 247 | 638 | 16 |
| Mutation 2 | AGTCCGCTGGCCGAGGTCGACTAC-GGCCGGTGAAGCAC | | | 248 | 52 | 0 |
| Mutation 3 | AGTCCGCTGGCCGAGGTCGACTACCtGGCCGGTGAAGCAC | | | 249 | 46 | 0 |
| Mutation 4 | AGTCCGCTGGCCGAGGTCGACTACCCGGCCGGTGAAGCAC | | | 250 | 35 | 0 |
| Mutation 5 | AGTCCGCGGTC-------aaGCCGGCGAAGCAC | | | 251 | 29 | 0 |
| Mutation 6 | AGTCCGCTGGCCG----------GTGAAGCAC | | | 252 | 28 | 0 |
| Mutation 7 | AGTCCGCTGGCCGAGGTCGACTA--aGCCGGTGAAGCAC | | | 253 | 27 | 0 |
| Mutation 8 | AGTCCGCTGGCCGACGT---------GAAGCAC | | | 254 | 23 | 0 |

FIG. 14B

CRISPR HYBRID DNA/RNA POLYNUCLEOTIDES AND METHODS OF USE

CROSS-REFERENCE TO RELATED APPLICATIONS

This application is a continuation of U.S. patent application Ser. No. 15/238,464, filed Aug. 16, 2016, which is a divisional of U.S. patent application Ser. No. 15/008,054, filed Jan. 27, 2016, which claims benefit of U.S. Provisional Patent Application Ser. No. 62/108,931, filed Jan. 28, 2015, and of U.S. Provisional Patent Application Ser. No. 62/251,548, filed Nov. 5, 2015, all of which are herein incorporated by reference.

INCORPORATION BY REFERENCE OF SEQUENCE LISTING PROVIDED AS A TEXT FILE

The instant application contains a Sequence Listing which has been submitted electronically in ASCII format and is hereby incorporated by reference in its entirety. Said ASCII copy, created on Jan. 26, 2016, is named 0198470101PTUS-_SL.txt and is 76,524 bytes in size.

BACKGROUND

Clustered Regularly Interspaced Short Palindromic Repeats (CRISPR) and CRISPR-associated (Cas) systems are prokaryotic immune system first discovered by Ishino in *E. coli*. Ishino et al. 1987 (Journal of Bacteriology 169 (12): 5429-5433 (1987)). This immune system provides immunity against viruses and plasmids by targeting the nucleic acids of the viruses and plasmids in a sequence-specific manner.

There are two main stages involved in this immune system, the first is acquisition and the second is interference. The first stage involves cutting the genome of invading viruses and plasmids and integrating segments of this into the CRISPR locus of the organism. The segments that are integrated into the genome are known as protospacers and help in protecting the organism from subsequent attack by the same virus or plasmid. The second stage involves attacking an invading virus or plasmid. This stage relies upon the protospacers being transcribed to RNA, this RNA, following some processing, then hybridizing with a complementary sequence in the DNA of an invading virus or plasmid while also associating with a protein, or protein complex that effectively cleaves the DNA.

There are several different CRISPR/Cas systems and the nomenclature and classification of these has changed as the systems are further characterized. In Type II systems there are two strands of RNA, a CRISPR RNA (crRNA) and a transactivating CRISPR RNA (tracrRNA) that are part of the CRISPR/Cas system. The tracrRNA hybridizes to a complementary region of pre-crRNA causing maturation of the pre-crRNA to crRNA. The duplex formed by the tracrRNA and crRNA is recognized by, and associates with a protein, Cas9, which is directed to a target nucleic acid by a sequence of the crRNA that is complementary to, and hybridizes with, a sequence in the target nucleic acid. It has been demonstrated that these minimal components of the RNA-based immune system could be reprogrammed to target DNA in a site-specific manner by using a single protein and two RNA guide sequences or a single RNA molecule. The CRISPR/Cas system is superior to other methods of genome editing involving endonucleases, meganucleases, zinc finger nucleases, and transcription activator-like effector nucleases (TALENs), which may require de novo protein engineering for every new target locus.

Being a RNA-guided system, CRISPR/Cas systems can be prone to issues with RNA-DNA hybrid structures, such as RNase A degradation of the RNA strand and higher possibility of RNA-DNA mismatches. Furthermore, synthesis of DNA oligonucleotides is more economical and robust than synthesis of RNA oligonucleotides. DNA-guided CRISPR systems may also recruit additional machinery to a specific target, compared to naturally occurring RNA-guided CRISPR systems. A need exists for an improved system that overcomes the problems associated with RNA based CRISPR/Cas systems, provides access to the decreased cost and increased robustness of DNA synthesis, and improves the specificity of the CRISPR/Cas system.

SUMMARY OF THE INVENTION

In some embodiments, the disclosure provides a single polynucleotide for use with a Class 2 CRISPR system comprising: a targeting region comprising deoxyribonucleic acid (DNA); and an activating region comprising ribonucleic acid (RNA). In some embodiments the targeting region comprises a mixture of DNA and RNA; and the activating region comprises DNA, RNA or a mixture of DNA and RNA.

In some embodiments, the disclosure provides a single polynucleotide for use with a Class 2 CRISPR system comprising: a targeting region comprising deoxyribonucleic acid (DNA); and an activating region comprising a polynucleotide region adjacent to said targeting region comprising a ribonucleic acid (RNA). In some embodiments the targeting region comprises a mixture of DNA and RNA; and the activating region comprises DNA, RNA or a mixture of DNA and RNA. In some embodiments the activating region is downstream of the targeting region. In some embodiments, the activating region is upstream of the targeting region. In some embodiments, the activating region comprises a structure selected from the group consisting of a lower stem, a bulge, an upper stem, a nexus, and a hairpin. In some embodiments, the activating region comprises a stem loop structure. In some embodiments, the activating region interacts with a Cas9 protein. In some embodiments, the activating region interacts with a Cpf1 protein.

In some embodiments, the disclosure provides a Class 2 CRISPR system comprising: a single polynucleotide comprising a targeting region comprising deoxyribonucleic acid (DNA) and configured to hybridize with a target sequence in a nucleic acid; an activating region adjacent to said targeting region comprising a ribonucleic acid (RNA); and a site-directed polypeptide. In some embodiments the nucleic acid is DNA, in some embodiments the nucleic acid is RNA, in some embodiments the nucleic acid is a mixture of RNA and DNA. In some embodiments, the activating region is downstream of the targeting region. In some embodiments, the activating region is upstream of the targeting region. In some embodiments, the site-directed polypeptide is a Cas9 protein. In some embodiments, the site-directed polypeptide is a Cpf1 protein. In some embodiments, the activating region comprises a structure selected from the group consisting of a lower stem, a bulge, an upper stem, a nexus, and a hairpin. In some embodiments, the activating region comprises a stem loop structure. In some embodiments, the activating region interacts with the site-directed polypeptide. In some embodiments the activating region comprises a mixture of DNA and RNA. In some embodiments, the targeting region comprises a mixture of DNA and RNA. In some embodiments, the Class 2 CRISPR system further comprises a donor polynucleotide.

In some embodiments, the disclosure provides a Class 2 CRISPR system comprising a first polynucleotide comprising (i) a targeting region comprising deoxyribonucleic acid (DNA) and configured to hybridize with a target sequence in a nucleic acid and (ii) an activating region adjacent to said targeting region comprising ribonucleic acid (RNA); a second polynucleotide comprising a sequence that is complementary to a sequence in said activating region of said first polynucleotide; and a site-directed polypeptide. In some embodiments, the activating region and the second polynucleotide hybridize to form one or more structures selected from the group consisting of a lower stem, a bulge, an upper stem, a nexus, and a duplex. In some embodiments, the site-directed polypeptide is a Cas9 protein. In some embodiments, the site-directed polypeptide is a Cpf1 protein. In some embodiments, the site-directed polypeptide interacts with the activating region. In some embodiments, the activating region comprises a mixture of DNA and RNA. In some embodiments, the second polynucleotide comprises RNA, DNA or a mixture of DNA and RNA.

In some embodiments, the disclosure provides two polynucleotides for use with a Class 2 CRISPR system comprising a first polynucleotide comprising (i) a targeting region comprising deoxyribonucleic acid (DNA) and configured to hybridize with a target sequence in a nucleic acid and (ii) an activating region adjacent to said targeting region comprising ribonucleic acid (RNA); and a second polynucleotide comprising a sequence that is complementary to a sequence in said activating region of said first polynucleotide. In some embodiments, the activating region and the second polynucleotide hybridize to form one or more structures selected from the group consisting of a lower stem, a bulge, an upper stem, a nexus, and a duplex. In some embodiments, the targeting region comprises a mixture of DNA and RNA, the activating region comprises a mixture of DNA and RNA and the second polynucleotide comprises a mixture of DNA and RNA.

In some embodiments, the disclosure provides a method of modifying a target nucleic acid molecule, the method comprising: contacting a target nucleic acid molecule having a target sequence with: a single polynucleotide comprising a targeting region comprising deoxyribonucleic acid (DNA) and configured to hybridize with a target sequence in a nucleic acid; an activating region adjacent to said targeting region comprising a ribonucleic acid (RNA); and a site-directed polypeptide, wherein the single polynucleotide forms a complex with the site-directed polypeptide and wherein said target nucleic acid molecule is cleaved or transcription of at least one gene encoded by the target nucleic acid molecule is modulated. In some embodiments the target nucleic acid is DNA, in some embodiments the target nucleic acid is RNA, in some embodiments the target nucleic acid is a mixture of RNA and DNA. In some embodiments, the activating region is downstream of the targeting region. In some embodiments, the activating region is upstream of the targeting region. In some embodiments, the site-directed polypeptide is a Cas9 protein. In some embodiments, the site-directed polypeptide is a Cpf1 protein. In some embodiments, the activating region comprises a structure selected from the group consisting of a lower stem, a bulge, an upper stem, a nexus, and a hairpin. In some embodiments, the activating region comprises a stem loop structure. In some embodiments, the activating region interacts with the site-directed polypeptide. In some embodiments the activating region comprises a mixture of DNA and RNA. In some embodiments, the targeting region comprises a mixture of DNA and RNA. In some embodiments, the method further includes providing a donor polynucleotide.

In some embodiments, the disclosure provides a method of modifying a target nucleic acid molecule, the method comprising: contacting a target nucleic acid molecule having a target sequence with: a first polynucleotide comprising (i) a targeting region comprising deoxyribonucleic acid (DNA) and configured to hybridize with a target sequence in a nucleic acid and (ii) an activating region adjacent to said targeting region comprising ribonucleic acid (RNA); providing a second polynucleotide comprising a sequence that is complementary to a sequence in said activating region of said first polynucleotide and a site-directed polypeptide, wherein the first and second polynucleotides form a complex with the site-directed polypeptide and wherein said target nucleic acid molecule is cleaved or transcription is modulated of at least one gene encoded by the target nucleic acid molecule is modulated. In some embodiments, the activating region and the second polynucleotide hybridize to form one or more structures selected from the group consisting of a lower stem, a bulge, an upper stem, a nexus, and a duplex. In some embodiments, the targeting region comprises a mixture of DNA and RNA, the activating region comprises a mixture of DNA and RNA and the second polynucleotide comprises a mixture of DNA and RNA. In some embodiments, the method further includes providing a donor polynucleotide.

In some embodiments, the disclosure provides a method for reducing off-target modification using a Class 2 CRISPR system comprising: contacting a target nucleic acid molecule having a target sequence with: a single polynucleotide comprising a targeting region comprising deoxyribonucleic acid (DNA) and configured to hybridize with a target sequence in a nucleic acid; an activating region adjacent to said targeting region comprising a ribonucleic acid (RNA); and a site-directed polypeptide, wherein the single polynucleotide forms a complex with the site-directed polypeptide and wherein said target nucleic acid molecule is cleaved or edited at the target sequence more preferentially than at other sequences in the target nucleic acid, thereby reducing off-target modification. In some embodiments the target nucleic acid is DNA, in some embodiments the target nucleic acid is RNA, in some embodiments the target nucleic acid is a mixture of RNA and DNA. In some embodiments, the activating region is downstream of the targeting region. In some embodiments, the activating region is upstream of the targeting region. In some embodiments, the site-directed polypeptide is a Cas9 protein. In some embodiments, the site-directed polypeptide is a Cpf1 protein. In some embodiments, the activating region comprises a structure selected from the group consisting of a lower stem, a bulge, an upper stem, a nexus, and a hairpin. In some embodiments, the activating region comprises a stem loop structure. In some embodiments, the activating region interacts with the site-directed polypeptide. In some embodiments the activating region comprises a mixture of DNA and RNA. In some embodiments, the targeting region comprises a mixture of DNA and RNA. In some embodiments, said targeting region is free of uracil. In some embodiments, the method further includes providing a donor polynucleotide.

In some embodiments, the disclosure provides a method for reducing off-target modification using a Class 2 CRISPR system comprising: contacting a target nucleic acid molecule having a target sequence with: a first polynucleotide comprising (i) a targeting region comprising deoxyribonucleic acid (DNA) and configured to hybridize with a target sequence in a nucleic acid and (ii) an activating region adjacent to said targeting region comprising ribonucleic acid (RNA); providing a second polynucleotide comprising a sequence that is complementary to a sequence in said activating region of said first polynucleotide and a site-directed polypeptide, wherein the first and second polynucleotides form a complex with the site-directed polypeptide and wherein said target nucleic acid molecule is cleaved or edited at the target sequence more preferentially than at other sequences in the target nucleic acid, thereby reducing off-target modification. In some embodiments the target nucleic acid is DNA, in some embodiments the target nucleic acid is RNA, in some embodiments the target nucleic acid is a mixture of RNA and DNA. In some embodiments, the activating region and the second polynucleotide hybridize to form one or more structures selected from the group consisting of a lower stem, a bulge, an upper stem, a nexus, and a duplex. In some embodiments, the site-directed polypeptide is a Cas9 protein. In some embodiments, the site-directed polypeptide is a Cpf1 protein. In some embodiments, the targeting region comprises a mixture of DNA and RNA, the activating region comprises a mixture of DNA and RNA and the second polynucleotide comprises a mixture of DNA and RNA. In some embodiments, said targeting region is free of uracil. In some embodiments, the method further includes providing a donor polynucleotide.

In some embodiments, the disclosure provides a method for increasing target specific modification using a Class 2 CRISPR system comprising: contacting a target nucleic acid molecule having a target sequence with: a single polynucleotide comprising a targeting region comprising deoxyribonucleic acid (DNA) and configured to hybridize with a target sequence in a nucleic acid; an activating region adjacent to said targeting region comprising a ribonucleic acid (RNA); and a site-directed polypeptide, wherein the single polynucleotide forms a complex with the site-directed polypeptide and wherein said target nucleic acid molecule is cleaved or edited at the target sequence more preferentially than at other sequences in the target nucleic acid, thereby increasing target specific modification. In some embodiments the target nucleic acid is DNA, in some embodiments the target nucleic acid is RNA, in some embodiments the target nucleic acid is a mixture of RNA and DNA. In some embodiments, the activating region is downstream of the targeting region. In some embodiments, the activating region is upstream of the targeting region. In some embodiments, the site-directed polypeptide is a Cas9 protein. In some embodiments, the site-directed polypeptide is a Cpf1 protein. In some embodiments, the activating region comprises a structure selected from the group consisting of a lower stem, a bulge, an upper stem, a nexus, and a hairpin. In some embodiments, the activating region comprises a stem loop structure. In some embodiments, the activating region interacts with the site-directed polypeptide. In some embodiments the activating region comprises a mixture of DNA and RNA. In some embodiments, the targeting region comprises a mixture of DNA and RNA. In some embodiments, the method further includes providing a donor polynucleotide.

In some embodiments, the disclosure provides a method for increasing target specific modification using a Class 2 CRISPR system comprising: contacting a target nucleic acid molecule having a target sequence with: a first polynucleotide comprising (i) a targeting region comprising deoxyribonucleic acid (DNA) and configured to hybridize with a target sequence in a nucleic acid and (ii) an activating region adjacent to said targeting region comprising ribonucleic acid (RNA); providing a second polynucleotide comprising a sequence that is complementary to a sequence in said activating region of said first polynucleotide and a site-directed polypeptide, wherein the first and second polynucleotides form a complex with the site-directed polypeptide and wherein said target nucleic acid molecule is cleaved or edited at the target sequence more preferentially than at other sequences in the target nucleic acid, thereby increasing target specific modification. In some embodiments the target nucleic acid is DNA, in some embodiments the target nucleic acid is RNA, in some embodiments the target nucleic acid is a mixture of RNA and DNA. In some embodiments, the activating region and the second polynucleotide hybridize to form one or more structures selected from the group consisting of a lower stem, a bulge, an upper stem, a nexus, and a duplex. In some embodiments, the site-directed polypeptide is a Cas9 protein. In some embodiments, the site-directed polypeptide is a Cpf1 protein. In some embodiments, the targeting region comprises a mixture of DNA and RNA, the activating region comprises a mixture of DNA and RNA and the second polynucleotide comprises a mixture of DNA and RNA. In some embodiments, said targeting region is free of uracil. In some embodiments, the method further includes providing a donor polynucleotide.

In some embodiments, the disclosure provides a method of introducing a donor polynucleotide into the genome of a cell or organism using a Class 2 CRISPR system comprising: contacting a target nucleic acid molecule having a target sequence with: a single polynucleotide comprising a targeting region comprising deoxyribonucleic acid (DNA) and configured to hybridize with a target sequence in a nucleic acid; an activating region adjacent to said targeting region comprising a ribonucleic acid (RNA); and a site-directed polypeptide, wherein the single polynucleotide forms a complex with the site-directed polypeptide and wherein said target nucleic acid molecule is cleaved at, or near the target sequence and providing a donor polynucleotide that is introduced into the genome of the cell or organism at the cleavage site. In some embodiments the target nucleic acid is DNA, in some embodiments the target nucleic acid is RNA, in some embodiments the target nucleic acid is a mixture of RNA and DNA. In some embodiments, the activating region is downstream of the targeting region. In some embodiments, the activating region is upstream of the targeting region. In some embodiments, the site-directed polypeptide is a Cas9 protein. In some embodiments, the site-directed polypeptide is a Cpf1 protein. In some embodiments, the activating region comprises a structure selected from the group consisting of a lower stem, a bulge, an upper stem, a nexus, and a hairpin. In some embodiments, the activating region comprises a stem loop structure. In some embodiments, the activating region interacts with the site-directed polypeptide. In some embodiments the activating region comprises a mixture of DNA and RNA. In some embodiments, the targeting region comprises a mixture of DNA and RNA. In some embodiments the donor polynucleotide is introduced into the nucleic acid by homologous recombination. In some embodiments the donor polynucleotide is introduced into the nucleic acid by non-homologous end joining.

In some embodiments, the disclosure provides a method of introducing a donor polynucleotide into the genome of a cell or organism using a Class 2 CRISPR system comprising: contacting a target nucleic acid molecule having a target sequence with: a first polynucleotide comprising (i) a targeting region comprising deoxyribonucleic acid (DNA) and configured to hybridize with a target sequence in a nucleic acid and (ii) an activating region adjacent to said targeting region comprising ribonucleic acid (RNA); providing a second polynucleotide comprising a sequence that is complementary to a sequence in said activating region of said first polynucleotide and a site-directed polypeptide, wherein the first and second polynucleotides form a complex with the site-directed polypeptide and wherein said target nucleic acid molecule is cleaved at, or near the target sequence and providing a donor polynucleotide that is introduced into the genome of the cell or organism at the cleavage site. In some embodiments the target nucleic acid is DNA, in some embodiments the target nucleic acid is RNA, in some embodiments the target nucleic acid is a mixture of RNA and DNA. In some embodiments, the activating region and the second polynucleotide hybridize to form one or more structures selected from the group consisting of a lower stem, a bulge, an upper stem, a nexus, and a duplex. In some embodiments, the targeting region comprises a mixture of DNA and RNA, the activating region comprises a mixture of DNA and RNA and the second polynucleotide comprises a mixture of DNA and RNA. In some embodiments, the activating region interacts with the site-directed polypeptide. In some embodiments the activating region comprises a mixture of DNA and RNA. In some embodiments, the targeting region comprises a mixture of DNA and RNA. In some embodiments, the site-directed polypeptide is a Cas9 protein. In some embodiments, the site-directed polypeptide is a Cpf1 protein. In some embodiments the donor polynucleotide is introduced into the nucleic acid by homologous recombination. In some embodiments the donor polynucleotide is introduced into the nucleic acid by non-homologous end joining. In some embodiments, the donor polynucleotide is introduced by microhomology-mediated end joining. In some embodiments, the donor polynucleotide is introduced by single-stranded annealing.

BRIEF DESCRIPTION OF THE DRAWINGS

FIGS. 10A-C show possible structures of a single guide D(R)NA of the present disclosure for use with a Type V CRISPR system.

FIGS. 11A-E show possible structures of a single guide D(R)NA of the present disclosure for use with a Type V CRISPR system.

FIGS. 12A-I show possible components of dual guides of the present disclosure comprising crRNA and/or crD(R)NA for use with a Type V CRISPR system.

FIGS. 13A-H show possible configurations of dual guides of the present disclosure comprising crRNA and/or crD(R) NA for use with a Type V CRISPR system.

FIGS. 14A-B show sequencing results of an in planta assay to determine the amount of cleavage of a target sequence by a Type II CRISPR/Cas system using nucleic acid targeting polynucleotides of the present disclosure.

DETAILED DESCRIPTION

Figure 1A:
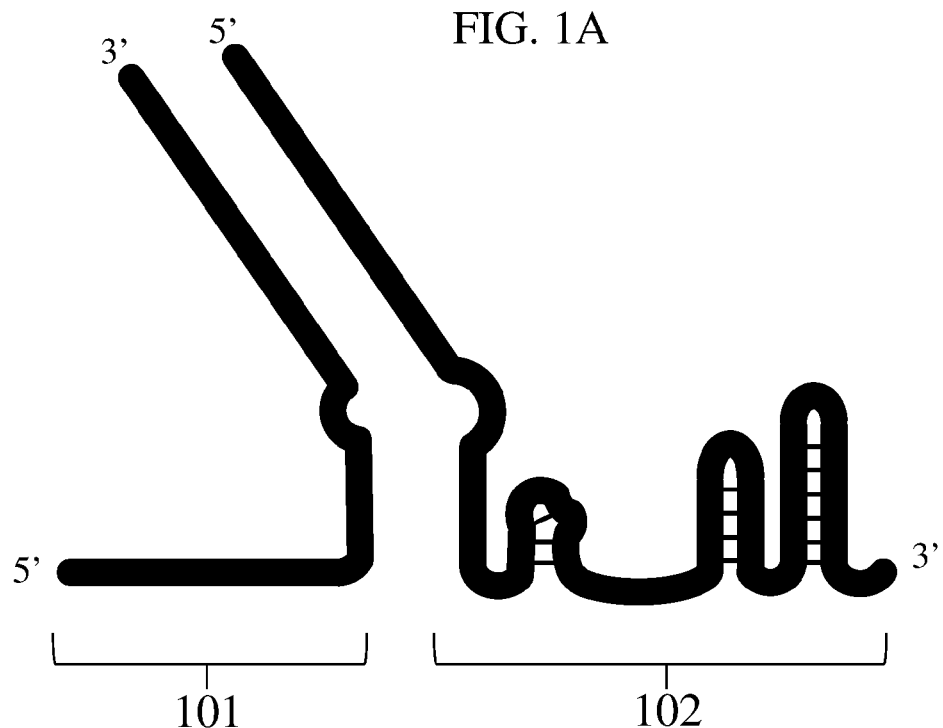
FIG. 1A shows a crD(R)NA and a tracrRNA of a Type II CRISPR system.

CRISPR/Cas systems have recently been reclassified into two classes, comprising five types and sixteen subtypes. Makarova et al. (Nature Reviews Microbiology 13:1-15 (2015)). This classification is based upon identifying all cas genes in a CRISPR/Cas locus and then determining the signature genes in each CRISPR/Cas locus, ultimately determining that the CRISPR/Cas systems can be placed in either Class 1 or Class 2 based upon the genes encoding the effector module, i.e., the proteins involved in the interference stage.

Class 1 systems have a multi-subunit crRNA-effector complex, whereas Class 2 systems have a single protein, such as Cas 9, Cpf1, C2c1, C2c2, C2c3, or a crRNA-effector complex. Class 1 systems comprise Type I, Type III and Type IV systems. Class 2 systems comprise Type II and Type V systems.

Type I systems all have a Cas3 protein that has helicase activity and cleavage activity. Type I systems are further divided into seven sub-types (I-A to I-F and I-U). Each type I subtype has a defined combination of signature genes and distinct features of operon organization. For example, sub-types I-A and I-B appear to have the cas genes organized in two or more operons, whereas sub-types I-C through I-F appear to have the cas genes encoded by a single operon. Type I systems have a multiprotein crRNA-effector complex that is involved in the processing and interference stages of the CRISPR/Cas immune system. This multiprotein complex is known as CRISPR-associated complex for antiviral defense (Cascade). Sub-type I-A comprises csa5 which encodes a small subunit protein and a cas8 gene that is split into two, encoding degraded large and small subunits and also has a split cas3 gene. An example of an organism with a sub-type I-A CRISPR/Cas system is *Archaeoglobus fulgidus*.

Sub-type I-B has a cas1-cas2-cas3-cas4-cas5-cas6-cas7-cas8 gene arrangement and lacks a csa5 gene. An example of an organism with sub-type I-B is *Clostridium kluyveri*.

Sub-type I-C does not have a cas6 gene. An example of an organism with sub-type I-C is *Bacillus halodurans*. Sub-type I-D has a Cas10d instead of a Cas8. An example of an organism with sub-type I-D is *Cyanothece* sp. Sub-type I-E does not have a cas4. An example of an organism with sub-type I-E is *Escherichia coli*. Sub-type I-F does not have a cas4 and has a cas2 fused to a cas3. An example of an organism with sub-type I-F is *Yersinia pseudotuberculosis*. An example of an organism with sub-type I-U is *Geobacter sulfurreducens*.

All type III systems possess a cas10 gene, which encodes a multidomain protein containing a Palm domain (a variant of the RNA recognition motif (RRM)) that is homologous to the core domain of numerous nucleic acid polymerases and cyclases and that is the largest subunit of type III crRNA-effector complexes. All type III loci also encode the small subunit protein, one Cas5 protein and typically several Cas7 proteins. Type III can be further divided into four sub-types, III-A through III-D. Sub-type III-A has a csm2 gene encoding a small subunit and also has cas1, cas2 and cas6 genes. An example of an organism with sub-type III-A is *Staphylococcus epidermidis*. Sub-type III-B has a cmr5 gene encoding a small subunit and also typically lacks cas1, cas2 and cas6 genes. An example of an organism with sub-type III-B is *Pyrococcus furiosus*. Sub-type III-C has a Cas10 protein with an inactive cyclase-like domain and lacks a cas1 and cas2 gene. An example of an organism with sub-type III-C is *Methanothermobacter thermautotrophicus*. Sub-type III-D has a Cas10 protein that lacks the HD domain, it lacks a cas1 and cas2 gene and has a cas5-like gene known as csx10. An example of an organism with sub-type III-D is *Roseiflexus* sp.

Type IV systems encode a minimal multisubunit crRNA-effector complex comprising a partially degraded large subunit, Csf1, Cas5, Cas7, and in some cases, a putative small subunit. Type IV systems lack cas1 and cas2 genes. Type IV systems do not have sub-types, but there are two distinct variants. One Type IV variant has a DinG family helicase, whereas a second type IV variant lacks a DinG family helicase, but has a gene encoding a small ca-helical protein. An example of an organism with a Type IV system is *Acidithiobacillus ferrooxidans*.

Type II systems have cas1, cas2 and cas9 genes. cas9 encodes a multidomain protein that combines the functions of the crRNA-effector complex with target DNA cleavage. Type II systems also encode a tracrRNA. Type II systems are further divided into three sub-types, sub-types II-A, II-B and II-C. Sub-type II-A contains an additional gene, csn2. An example of an organism with a sub-type II-A system is *Streptococcus thermophilus*. Sub-type II-B lacks csn2, but has cas4. An example of an organism with a sub-type II-B system is *Legionella pneumophila*. Sub-type II-C is the most common Type II system found in bacteria and has only three proteins, Cas1, Cas2 and Cas9. An example of an organism with a sub-type II-C system is *Neisseria lactamica*.

Type V systems have a cpf1 gene and cas1 and cas2 genes. The cpf1 gene encodes a protein, Cpf1, that has a RuvC-like nuclease domain that is homologous to the respective domain of Cas9, but lacks the HNH nuclease domain that is present in Cas9 proteins. Type V systems have been identified in several bacteria, including *Parcubacteria bacterium* GWC2011_GWC2_44_17 (PbCpf1), *Lachnospiraceae bacterium* MC2017 (Lb3 Cpf1), *Butyrivibrio proteoclasticus* (BpCpf1), *Peregrinibacteria bacterium* GW2011_GWA_33_10 (PeCpf1), *Acidaminococcus* sp. BV3L6 (AsCpf1), *Porphyromonas macacae* (PmCpf1), *Lachnospiraceae bacterium* ND2006 (LbCpf1), *Porphyromonas crevioricanis* (PcCpf1), *Prevotella disiens* (PdCpf1), *Moraxella bovoculi* 237 (MbCpf1), *Smithella* sp. SC_K08D17 (SsCpf1), *Leptospira inadai* (LiCpf1), *Lachnospiraceae bacterium* MA2020 (Lb2Cpf1), *Franciscella novicida* U112 (FnCpf1), *Candidatus methanoplasma termitum* (CMtCpf1), and *Eubacterium eligens* (EeCpf1).

In Class 1 systems, the expression and interference stages involve multisubunit CRISPR RNA (crRNA)-effector complexes. In Class 2 systems, the expression and interference stages involve a single large protein, e.g., Cas9, Cpf1, C2C1, C2C2, or C2C3.

In Class 1 systems, pre-crRNA is bound to the multisubunit crRNA-effector complex and processed into a mature crRNA. In Type I and III systems this involves an RNA endonuclease, e.g., Cas6. In Class 2 Type II systems, pre-crRNA is bound to Cas9 and processed into a mature crRNA in a step that involves RNase III and a tracrRNA. However, in at least one Type II CRISPR-Cas system, that of *Neisseria meningitidis*, crRNAs with mature 5' ends are directly transcribed from internal promoters, and crRNA processing does not occur.

In Class 1 systems the crRNA is associated with the crRNA-effector complex and achieves interference by combining nuclease activity with RNA-binding domains and base pair formation between the crRNA and a target nucleic acid.

In Type I systems, the crRNA and target binding of the crRNA-effector complex involves Cas7, Cas5, and Cas8 fused to a small subunit protein. The target nucleic acid cleavage of Type I systems involves the HD nuclease domain, which is either fused to the superfamily 2 helicase Cas3' or is encoded by a separate gene, cas3".

In Type III systems, the crRNA and target binding of the crRNA-effector complex involves Cas7, Cas5, Cas10 and a small subunit protein. The target nucleic acid cleavage of Type III systems involves the combined action of the Cas7 and Cas10 proteins, with a distinct HD nuclease domain fused to Cas10, which is thought to cleave single-stranded DNA during interference.

In Class 2 systems the crRNA is associated with a single protein and achieves interference by combining nuclease activity with RNA-binding domains and base pair formation between the crRNA and a target nucleic acid.

In Type II systems, the crRNA and target binding involves Cas9 as does the target nucleic acid cleavage. In Type II systems, the RuvC-like nuclease (RNase H fold) domain and the HNH (McrA-like) nuclease domain of Cas9 each cleave one of the strands of the target nucleic acid. The Cas9 cleavage activity of Type II systems also requires hybridization of crRNA to tracrRNA to form a duplex that facilitates the crRNA and target binding by the Cas9.

In Type V systems, the crRNA and target binding involves Cpf1 as does the target nucleic acid cleavage. In Type V systems, the RuvC-like nuclease domain of Cpf1 cleaves both strands of the target nucleic acid in a staggered configuration, producing 5' overhangs, which is in contrast to the blunt ends generated by Cas9 cleavage. These 5' overhangs may facilitate insertion of DNA through non-homologous end-joining methods.

The Cpf1 cleavage activity of Type V systems also does not require hybridization of crRNA to tracrRNA to form a duplex, rather the crRNA of Type V systems use a single crRNA that has a stem loop structure forming an internal duplex. Cpf1 binds the crRNA in a sequence and structure specific manner, that recognizes the stem loop and sequences adjacent to the stem loop, most notably, the nucleotide 5' of the spacer sequences that hybridizes to the target nucleic acid. This stem loop structure is typically in the range of 15 to 19 nucleotides in length. Substitutions that disrupt this stem loop duplex abolish cleavage activity, whereas other substitutions that do not disrupt the stem loop duplex do not abolish cleavage activity. In Type V systems, the crRNA forms a stem loop structure at the 5' end and the sequence at the 3' end is complementary to a sequence in a target nucleic acid.

Other proteins associated with Type V crRNA and target binding and cleavage include Class 2 candidate 1 (C2c1) and Class 2 candidate 3 (C2c3). C2c1 and C2c3 proteins are similar in length to Cas9 and Cpf1 proteins, ranging from approximately 1,100 amino acids to approximately 1,500 amino acids. C2c1 and C2c3 proteins also contain RuvC-like nuclease domains and have an architecture similar to Cpf1. C2c1 proteins are similar to Cas9 proteins in requiring a crRNA and a tracrRNA for target binding and cleavage, but have an optimal cleavage temperature of 50° C. C2c1 proteins target an AT-rich PAM, which similar to Cpf1, is 5' of the target sequence, see, e.g., Shmakov et al. (Molecular Cell; 60 (3): 385-397 (2015)).

Class 2 candidate 2 (C2c2) does not share sequence similarity to other CRISPR effector proteins, and therefore may be in a putative Type VI system. C2c2 proteins have two HEPN domains and are predicted to have RNase activity, and therefore may target and cleave mRNA. C2c2 proteins appear similar to Cpf1 proteins in requiring crRNA for target binding and cleavage, while not requiring tracrRNA. Also like Cpf1, the crRNA for C2c2 proteins forms a stable hairpin, or stem loop structure, that may aid in association with the C2c2 protein.

As used herein, "site-directed polypeptide" refers to a single protein, or protein complex, used in a CRISPR system with the polynucleotides disclosed herein. A site-directed polypeptide can comprise one or more nuclease domains. A site-directed polypeptide of the disclosure can comprise a HNH or HNH-like nuclease domain, a RuvC or RuvC-like nuclease domain, and/or HEPN-superfamily-like nucleases. HNH or HNH-like domains can comprise a McrA-like fold. HNH or HNH-like domains can comprise two antiparallel β-strands and an a-helix. HNH or HNH-like domains can comprise a metal binding site (e.g., divalent cation binding site). HNH or HNH-like domains can cleave one strand of a target nucleic acid (e.g., complementary strand of the crRNA targeted strand). Proteins that comprise an HNH or HNH-like domain can include endonucleases, colicins, restriction endonucleases, transposases, and DNA packaging factors.

A site-directed polypeptide can be a Cas9 protein, a Cpf1 protein, a C2c1 protein, a C2c2 protein, a C2c3 protein, Cas3, Cas 5, Cas7, Cas8, Cas10, or complexes of these, dependent upon the particular CRISPR system being used. In some embodiments, the site-directed polypeptide can be a Cas9 or a Cpf1 protein. In some embodiments, a site-directed polypeptide with reduced nuclease activity can be a nickase, i.e., it can be modified to cleave one strand of a target nucleic acid duplex. In some embodiments, a site-directed polypeptide can be modified to have no nuclease activity, i.e., it does not cleave any strand of a target nucleic acid duplex, or any single strand of a target nucleic acid. Examples of site-directed polypeptides with reduced, or no nuclease activity can include a Cas9 with a modification to the HNH and/or RuvC nuclease domains, and a Cpf1 with a modification to the RuvC nuclease domain. Non-limiting examples of such modifications can include D917A, E1006A and D1225A to the RuvC nuclease domain of the *F. novicida* Cpf1 and alteration of residues D10, G12, G17, E762, H840, N854, N863, H982, H983, A984, D986, and/or A987 of the *S. pyogenes* Cas9, and their corresponding amino acid residues in other Cpf1 and Cas9 proteins.

In some embodiments, a site-directed polypeptide may be modified. Such modifications may include the incorporation or fusion of a domain from another polypeptide to a site-directed polypeptide, or replacement of a domain of a site-directed polypeptide with a domain of another polypeptide. For example, a modified site-directed polypeptide can contain a first domain from a Cas9 or Cpf1 protein and a second domain from a protein other than Cas9 or Cpf1. The modification to include such domains in the modified site-directed polypeptides may confer additional activity on the modified site-directed polypeptides. Such activities can include nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity, glycosylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity) that modifies a polypeptide associated with target nucleic acid (e.g., a histone).

In some embodiments, a site-directed polypeptide can introduce double-stranded breaks or single-stranded breaks in nucleic acid sequences, (e.g., genomic DNA). In certain embodiments, a nucleic acid sequence may be a target nucleic acid. Certain site-directed polypeptides of the present disclosure can introduce blunt-end cleavage sites while certain embodiments produce cleavage sites having sticky ends, i.e., 5' or 3' overhangs. Cpf1, for example, may introduce a staggered DNA double-stranded break with about a 4 or 5 nucleotide (nt) 5' overhang. A double-stranded break can stimulate a cell's endogenous DNA-repair pathways (e.g., homologous recombination and non-homologous end joining (NHEJ) or alternative non-homologous end-joining (A-NHEJ)). NHEJ can repair a cleaved target nucleic acid without the need for a homologous template. This can result in deletions of the target nucleic acid. Homologous recombination (HR) can occur with a homologous template. The homologous template can comprise sequences that are homologous to sequences flanking the target nucleic acid cleavage site. After a target nucleic acid is cleaved by a site-directed polypeptide the site of cleavage can be destroyed (e.g., the site may not be accessible for another round of cleavage with a nucleic acid-targeting polynucleotide and site-directed polypeptide).

In some cases, homologous recombination can insert an exogenous polynucleotide sequence into the target nucleic acid cleavage site. An exogenous polynucleotide sequence can be called a donor polynucleotide or a donor sequence. In some embodiments, a donor polynucleotide, a portion of a donor polynucleotide, a copy of a donor polynucleotide, or a portion of a copy of a donor polynucleotide can be inserted into a target nucleic acid cleavage site. A donor polynucleotide can be an exogenous polynucleotide sequence. A donor polynucleotide can be single-stranded DNA. A donor polynucleotide can be double-stranded DNA. A donor polynucleotide can be RNA. A donor polynucleotide can be a duplex of RNA and DNA. A donor polynucleotide can be a sequence that does not naturally occur at a target nucleic acid cleavage site. In some embodiments, modifications of a target nucleic acid due to NHEJ and/or HR can lead to, for example, mutations, deletions, alterations, integrations, gene correction, gene replacement, gene tagging, transgene insertion, nucleotide deletion, gene disruption, and/or gene mutation. The process of integrating non-native nucleic acid(s) into genomic DNA can be referred to as "genome engineering."

Figure 2:
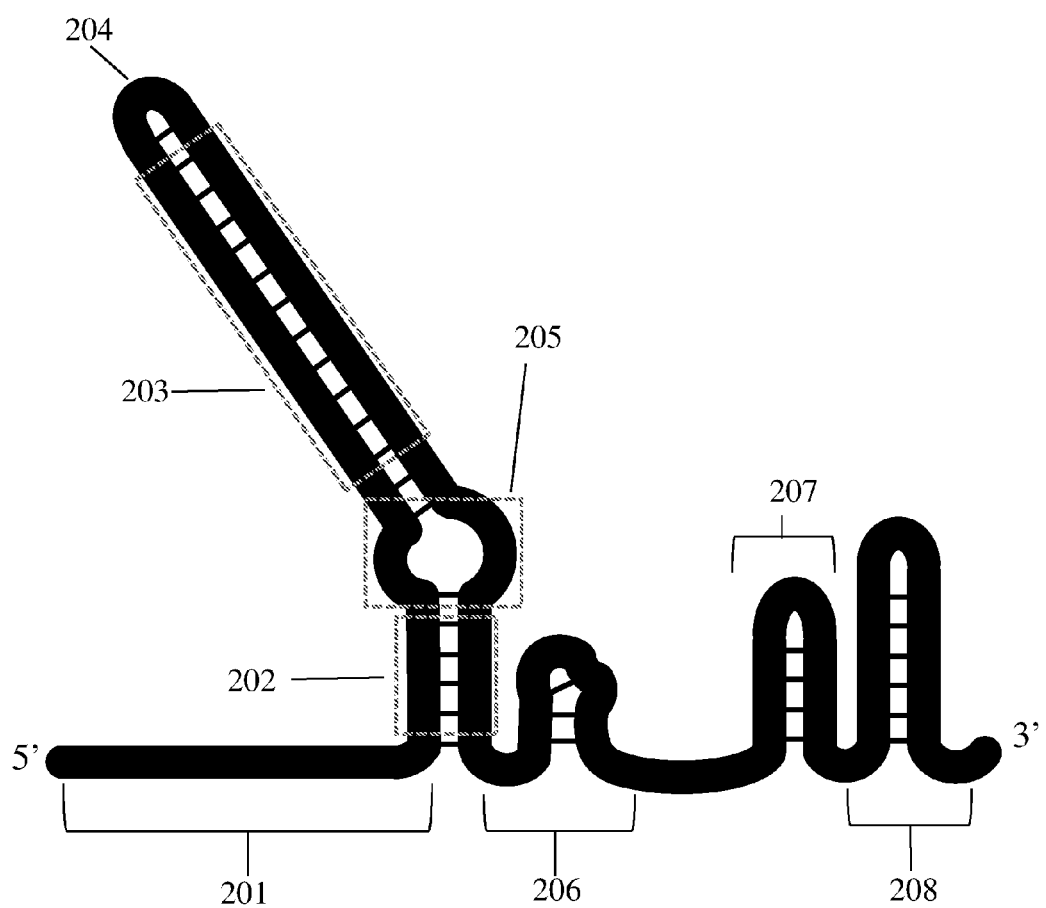
FIG. 2 shows a single polynucleotide of the present disclosure comprising a targeting region linked to an activating region (also referred to as a "single guide" system or a "single guide D(R)NA" or "sg D(R)NA").

A CRISPR system of the present disclosure may be referred to as a "DNA-guided CRISPR system." A CRISPR system of the present disclosure can be programmed to cleave a target nucleic acid using two nucleic acid targeting polynucleotides ("dual guide"). In some embodiments a dual guide CRISPR system can include a CRISPR-D(R)NA (crD(R)NA) and a transactivating CRISPR RNA (tracrRNA), e.g., one polynucleotide comprising both DNA and RNA and a second polynucleotide comprising RNA. In some embodiments, a dual guide system can include a crD(R)NA and a tracrD(R)NA, e.g., one polynucleotide comprising both DNA and RNA and a second polynucleotide comprising both DNA and RNA. crD(R)NA and tracrD(R)NA or tracrRNA elements can be connected by a fusion region (e.g., a linker) and synthesized as a single element (e.g., sgD(R)NA) as illustrated in FIG. 2 ("single guide").

As used herein, the term "crD(R)NA" refers to a polynucleotide comprising a targeting region and an activating region, wherein the targeting region comprises DNA, or DNA and RNA, and wherein the activating region comprises RNA, or DNA, or a mixture of DNA and RNA. In certain embodiments, a targeting region is upstream of an activating region. In certain embodiments, an activating region is upstream of a targeting region. In some embodiments a tracrRNA comprises a sequence that is complementary to a sequence in the activating region of a crD(R)NA.

As used herein, the term "tracrD(R)NA" refers to a polynucleotide having a sequence that is complementary to a sequence in the activating region of a crD(R)NA and wherein the polynucleotide comprises DNA or a mixture of DNA and RNA.

As used herein, the term "targeting region" refers to a region of a polynucleotide comprising DNA, or a mixture of DNA and RNA that is complementary to a sequence in a target nucleic acid. In certain embodiments, a targeting region may also comprise other nucleic acids, or nucleic acid analogues, or combinations thereof. In certain embodiments, a targeting region may be comprised solely of DNA because this configuration may be less likely to decompose inside of a host cell. In some embodiments this configuration may increase the specificity of target sequence recognition and/or reduce the occurrence of off-target binding/hybridization.

As used herein, the term "activating region" refers to a portion of a polynucleotide comprising RNA, or DNA, or a mixture of DNA and RNA that interacts, or is capable of associating, or binding with a site-directed polypeptide. In certain embodiments, an activating region may also comprise other nucleic acids, or nucleic acid analogues, or combinations thereof. In certain embodiments, an activating region is adjacent to a targeting region. In certain embodiments, the activating region is downstream from the targeting region. In certain embodiments, the activating region is upstream from the targeting region.

As used herein, the term "sgD(R)NA," or "single guide D(R)NA" refers to a polynucleotide comprising a targeting region and an activating region, wherein the targeting region comprises DNA, RNA, or a mixture of DNA and RNA that is complementary to a sequence in a target nucleic acid, wherein the activating region comprises RNA, or DNA, or a mixture of DNA and RNA, wherein either the targeting region or the activating region or both comprise at least one DNA nucleotide, and wherein the activating region has sequences that are self complementary, which hybridize to form a duplex, which may contain secondary structures. An example of a single guide D(R)NA can be constructed from a crD(R)NA and tracrD(R)NA or tracrRNA, wherein the crD(R)NA and tracrD(R)NA, or the crD(R)NA and tracrRNA are connected by a sequence of nucleotides, which can be DNA, RNA, or a mixture of DNA and RNA.

As used herein, the term "downstream" refers to a point that is distal from a point of reference in a 3' direction of a nucleotide sequence. As used herein, the term "upstream" refers to a point that is distal from a point of reference in a 5' direction of a nucleotide sequence.

A polynucleotide of the present disclosure, e.g., crD(R)NA, tracrD(R)NA, or single guide D(R)NA, may also comprise a mixture of DNA and other nucleic acids, e.g., peptide nucleic acid (PNA), or other nucleic acid analogues.

The disclosure provides for the use of any length of single guide D(R)NAs, crD(R)NAs, tracrD(R)NAs and/or tracrRNAs and combinations of polynucleotides as disclosed herein that support programmable cleavage and/or modification of a target nucleic acid by a site-directed polypeptide.

FIG. 1A shows polynucleotides for use in a Type II CRISPR system. In this embodiment, 101 can be a crD(R)NA and 102 can be a tracrD(R)NA or a tracrRNA.

Figure 1B:
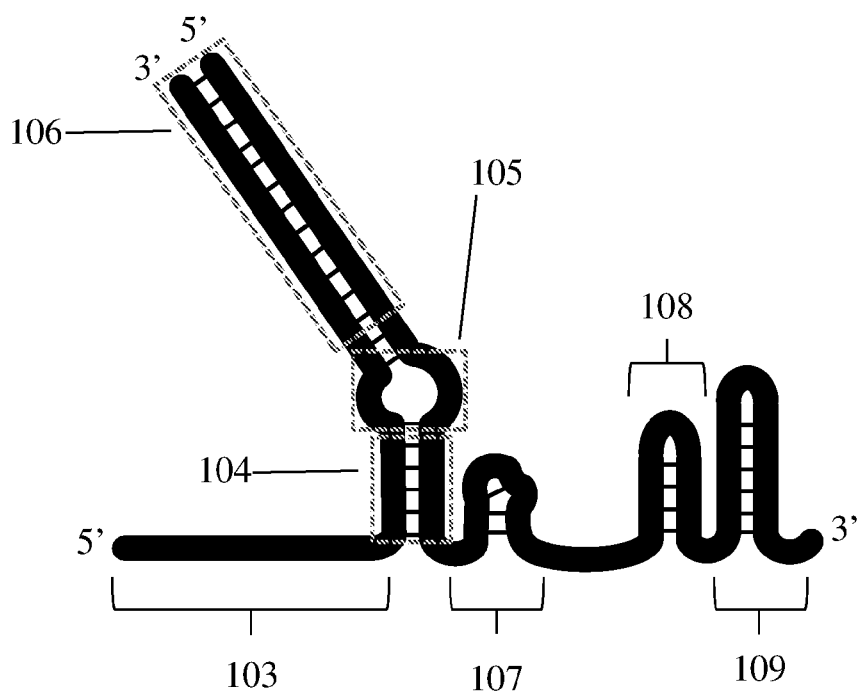
FIG. 1B shows two polynucleotides (a crD(R)NA and a tracrRNA or a tracrD(R)NA) of the present disclosure hybridized to each other (also referred to as a "dual guide" system).

FIG. 1B shows the polynucleotides of FIG. 1A hybridized to each other along regions of complementarity. The hybridization may generate secondary structures such as a bulge 105, a targeting region 103, a nexus 107, and hairpins 108 and 109. FIG. 1B also shows an embodiment comprising an upper duplex region 106 and a lower duplex region 104. An upper duplex region may comprise an upper stem. A lower duplex region may comprise a lower stem. In certain embodiments, the polynucleotides that hybridize to form region 104 may comprise a mixture of DNA and RNA on the same polynucleotide strand, e.g., 102, in a region downstream of a targeting region 103. In certain embodiments, region 104 as shown in FIG. 1B, may comprise a mixture of DNA and RNA on the same polynucleotide strand, e.g., 102. A nucleotide sequence immediately downstream of a targeting region may comprise various proportions of DNA and RNA. In certain embodiments, this apportionment may be 5%, 10%, 15%, 20%, 25%, 30%, 35%, 40%, 45%, 50%, 55%, 60%, 65%, 70%, 75%, 80%, 85%, 90%, 95%, or 100% RNA and ranges there between. As described herein, a nucleotide sequence downstream (e.g., a region between a targeting region 103 and a bulge 105 as shown in FIG. 1B) of a targeting region 103, may comprise a mixture of DNA and RNA as shown in SEQ ID NOs. 19-26.

FIG. 2 shows an example of a single guide D(R)NA for use with a Type II CRISPR system. Referring to FIG. 2, the embodiment comprises a targeting region 201, a lower duplex region 202, an upper duplex region 203, a fusion region 204, a secondary structure (e.g., a bulge) 205, a nexus 206, and hairpins 207 and 208. An upper duplex region may comprise an upper stem. A lower duplex region may comprise a lower stem. Some embodiments may comprise an activating region comprising an upper duplex region and a lower duplex region. In some embodiments, region 202 may comprise a mixture of DNA and RNA, which is immediately downstream of a targeting region 201. A nucleotide sequence immediately downstream of a targeting region may comprise various proportions of DNA and RNA. In certain embodiments, this apportionment may be 5%, 10%, 15%, 20%, 25%, 30%, 35%, 40%, 45%, 50%, 55%, 60%, 65%, 70%, 75%, 80%, 85%, 90%, 95%, or 100% RNA and ranges there between. As described herein, a nucleotide region downstream (e.g., a region between a targeting region 201 and a bulge 205 as shown in FIG. 2) of a targeting region 201 may comprise a mixture of DNA and RNA as shown in SEQ ID NOs. 127-132. In some embodiments, region 203 may comprise a mixture of DNA and RNA, which is downstream of a targeting region 201. A nucleotide sequence downstream of a targeting region may comprise various proportions of DNA and RNA. In certain embodiments, this apportionment may be 5%, 10%, 15%, 20%, 25%, 30%, 35%, 40%, 45%, 50%, 55%, 60%, 65%, 70%, 75%, 80%, 85%, 90%, 95%, or 100% RNA and ranges there between. As described herein, a nucleotide region downstream of a targeting region 201 may comprise a mixture of DNA and RNA as shown in SEQ ID NOs. 44-47 and 129.

In certain embodiments, an activating region may comprise at least one secondary structure. A secondary structure may be a lower stem, an upper stem, a bulge, a nexus, a hairpin, one or more of these, and combinations thereof. In certain embodiments, an activating region comprises a bulge. FIG. 1B shows secondary structures created by a dual guide system, i.e., a crD(R)NA hybridizing to a tracrD(R)NA or a crD(R)NA hybridizing to a tracrRNA, including a lower stem 104, a bulge 105, an upper stem 106, a nexus 107, and a hairpin, e.g., 108. Secondary structures may also include additional types of structures. The positioning of and number of secondary structures is not particularly limited and may be altered depending upon which site-directed polypeptide is used in a CRISPR system.

In certain embodiments, an activating region may comprise a nucleotide region comprising a lower stem, an upper stem, and a bulge. In certain embodiments, there may only be a bulge. In certain embodiments, a bulge may be between a lower stem and an upper stem. Certain embodiments may omit an upper stem. The terms "upper stem" and "lower stem" may be used herein only to reference an illustrated location of an activating region and are not necessarily intended to limit these regions to any particular structure, secondary structure, or positioning. For example, FIG. 1B shows a lower stem, 104, positioned between a bulge and a spacer. In certain embodiments, the targeting region may comprise a spacer.

In some embodiments, a nucleotide sequence downstream from a targeting region in a lower stem can have a sequence that is 5'GYYYUR, wherein Y is C or U/T and R is A or G. In some embodiments, a nucleotide sequence downstream from a targeting region in a lower stem can have a sequence that is 5'GUUUUUGU. In some embodiments, a nucleotide sequence downstream from a targeting region in a lower stem can have a sequence that is 5'GUUUUA. In some embodiments, the nucleotides in the lower stem may be RNA or DNA or a mixture of DNA and RNA.

In certain embodiments, a secondary structure may comprise a bulge. A bulge can refer to an unpaired region of nucleotides within a duplex. In certain embodiments, a single guide D(R)NA may comprise a bulge. Certain embodiments of polynucleotides for use in a CRISPR system may comprise a secondary structure and said secondary structure is a tetraloop. A single guide D(R)NA comprising a bulge may comprise a 5' side and a 3' side of a duplex. Referring to FIG. 2, for example, a 5' side of a duplex can refer to a region that is upstream (i.e., in the 5' direction) of 204 and a 3' side of a duplex can refer to a region that is downstream (i.e., in the 3' direction) of 204. In certain embodiments, an activating region comprises a bulge. In some embodiments, a bulge can be involved in binding to, or interacting with, a site-directed polypeptide. A bulge can comprise, on one side of a duplex, an unpaired 5'-RRRZ-3' wherein R is any purine and Z can be a nucleotide that can form a wobble pair with a nucleotide on the opposite strand, and an unpaired nucleotide region on the other side of the duplex. A bulge may comprise DNA, RNA, and mixtures thereof. A bulge may comprise DNA, RNA, or a mixture thereof on a 5' side of a bulge duplex and may comprise DNA, RNA, or a mixture thereof on a 3' side of a bulge. In certain embodiments a polynucleotide for use in a CRISPR system may comprise a targeting region and an activating region, and a targeting region side of a bulge duplex may comprise DNA, RNA, and mixtures thereof, and an activating region side of a bulge duplex may contain DNA, RNA, and mixtures thereof. For example, in one embodiment, a side of a bulge that is closer to a 5' end of a polynucleotide may comprise RNA and a side of a bulge that is closer to a 3' end of a polynucleotide may comprise RNA. In certain embodiments, a side of a bulge may comprise fewer nucleotides than another side of a bulge. In certain embodiments, a polynucleotide for use with a CRISPR system comprises a polynucleotide having a 5' direction and a 3' direction and comprises a bulge having a 5' side and a 3' side and a 5' side may comprise DNA and/or RNA and a 3' side may comprise RNA. In certain embodiments, a polynucleotide for use with a CRISPR system comprises a polynucleotide having a 5' direction and a 3' direction and comprises a bulge having a 5' side and a 3' side and a 5' side may comprise DNA and/or RNA and a 3' side may comprise RNA and a 3' side may have more nucleotides than a 5' side of said bulge. In some embodiments, polynucleotides for use in a CRISPR system may comprise a crD(R)NA and a tracrD(R)NA, and a crD(R)NA side of a bulge duplex may comprise DNA, RNA, and mixtures thereof comprising two nucleotides; and a tracrD(R)NA side of a bulge duplex may contain DNA, RNA, and mixtures thereof. In some embodiments, polynucleotides for use in a CRISPR system may comprise a crD(R)NA and a tracrRNA, and a crD(R)NA side of a bulge duplex may comprise DNA, RNA, and mixtures thereof comprising two nucleotides; and the tracrRNA side of a bulge duplex may contain more than two nucleotides.

For example, a bulge can comprise an unpaired purine (e.g., adenine) on a side of a bulge. In some embodiments, a bulge can comprise an unpaired 5'-AAGZ-3' on a side of the bulge, wherein Z can be a nucleotide that can form a wobble pairing with a nucleotide on another side of the bulge.

A bulge on a first side of a duplex (e.g., a side that is toward the 5' end of a polynucleotide for use in a CRISPR system) can comprise at least 1, 2, 3, 4, or 5 or more unpaired nucleotides. A bulge on a first side of a duplex (e.g., a side that is toward the 5' end of a polynucleotide for use in a CRISPR system) can comprise at most 1, 2, 3, 4, or 5 or more unpaired nucleotides. A bulge on a first side of a duplex (e.g., a side that is toward the 5' end of a polynucleotide for use in a CRISPR system) can comprise 1 unpaired nucleotide.

A bulge on a second side of the duplex (e.g., a tracrRNA or a tracrD(R)NA side of the duplex) can comprise at least 1, 2, 3, 4, 5, 6, 7, 8, 9, or 10 or more unpaired nucleotides. A bulge on a second side of a duplex (e.g., a tracrRNA or tracrD(R)NA side of the duplex) can comprise 1, 2, 3, 4, 5, 6, 7, 8, 9, or 10 or more unpaired nucleotides. A bulge on a second side of a duplex (e.g., a tracrRNA or tracrD(R)NA side of a duplex) can comprise 4 unpaired nucleotides.

Regions of different numbers of unpaired nucleotides on each strand of a duplex can be paired together. Certain embodiments may comprise a secondary structure comprising a bulge wherein said bulge is not forming a duplex. A bulge can comprise 5 unpaired nucleotides from a first strand and 1 unpaired nucleotide from a second strand. A bulge can comprise 4 unpaired nucleotides from a first strand and 1 unpaired nucleotide from a second strand. A bulge can comprise 3 unpaired nucleotides from a first strand and 1 unpaired nucleotide from a second strand. A bulge can comprise 2 unpaired nucleotides from a first strand and 1 unpaired nucleotide from a second strand. A bulge can comprise 1 unpaired nucleotide from a first strand and 1 unpaired nucleotide from a second strand. A bulge can comprise 1 unpaired nucleotide from a first strand and 2 unpaired nucleotides from a second strand. A bulge can comprise 1 unpaired nucleotide from a first strand and 3 unpaired nucleotides from a second strand. A bulge can comprise 1 unpaired nucleotide from a first strand and 4 unpaired nucleotides from a second strand. A bulge can comprise 1 unpaired nucleotide from a first strand and 5 unpaired nucleotides from a second strand.

In certain embodiments, an unpaired secondary structure may be formed on a crD(R)NA side of a polynucleotide. In certain embodiments, an unpaired secondary structure may be formed on a crD(R)NA side of a polynucleotide and may further comprise an unpaired secondary structure on a tracrRNA or tracrD(R)NA side. In such an embodiment, these secondary structures may be bulges. In certain embodiments, the term "unpaired" when referring to a secondary structure, can mean that the secondary structure is not in the form of a duplex.

In some instances a bulge can comprise at least one wobble pairing. In some instances, a bulge can comprise at most one wobble pairing. A bulge sequence can comprise at least one purine nucleotide. A bulge sequence can comprise at least 3 purine nucleotides. A bulge sequence can comprise at least 5 purine nucleotides. A bulge sequence can comprise at least one guanine nucleotide. A bulge sequence can comprise at least one adenine nucleotide. A bulge sequence can comprise uracil. A secondary structure may comprise DNA, RNA, and combinations thereof. In certain embodiments, a secondary structure may form a duplex structure and said duplex structure may comprise a bulge comprising DNA and RNA.

A tracrD(R)NA sequence can have a length of from about 6 nucleotides to about 150 nucleotides. For example, a tracrD(R)NA sequence can have a length of from about 6 nucleotides (nt) to about 50 nt, from about 6 nt to about 40 nt, from about 6 nt to about 30 nt, from about 6 nt to about 25 nt, from about 6 nt to about 20 nt, from about 6 nt to about 15 nt, from about 8 nt to about 40 nt, from about 8 nt to about 30 nt, from about 8 nt to about 25 nt, from about 8 nt to about 20 nt or from about 8 nt to about 15 nt, from about 15 nt to about 150 nt, from about 15 nt to about 130 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt. In some embodiments, a tracrD(R)NA sequence has a length of approximately 14 nucleotides. In certain embodiments a tracrD(R)NA is comprised solely of DNA. A tracrD(R)NA sequence can be at least about 60% identical to a reference tracrRNA sequence (e.g., wild type tracrRNA sequence from S. pyogenes) over a stretch of at least 6, 7, or 8 contiguous nucleotides. For example, a tracrD(R)NA sequence can be at least about 60% identical, at least about 65% identical, at least about 70% identical, at least about 75% identical, at least about 80% identical, at least about 85% identical, at least about 90%) identical, at least about 95% identical, at least about 98% identical, at least about 99% identical, or 100% identical, to a reference tracrRNA sequence (e.g., wild type tracrRNA sequence from S. pyogenes) over a stretch of at least 6, 7, or 8 contiguous nucleotides.

A tracrD(R)NA sequence can comprise more than one duplexed region (e.g., hairpin, hybridized region). A tracrD(R)NA sequence can comprise two duplexed regions. A tracrD(R)NA may comprise a secondary structure. A tracrD(R)NA may contain more than one secondary structure. In certain embodiments, a tracrD(R)NA sequence may comprise a first secondary structure and a second secondary structure and a first secondary structure comprises more nucleotides than a second secondary structure. In certain embodiments, a tracrD(R)NA may comprise a first secondary structure, a second secondary structure, and a third secondary structure and said first secondary structure comprises less nucleotides than said second secondary structure and said second secondary structure comprises more nucleotides than said third secondary structure. The number of secondary structures and corresponding nucleotide lengths is not particularly limited.

A tracrRNA sequence can have a length of from about 6 nucleotides to about 150 nucleotides. For example, a tracrRNA sequence can have a length of from about 6 nt to about 50 nt, from about 6 nt to about 40 nt, from about 6 nt to about 30 nt, from about 6 nt to about 25 nt, from about 6 nt to about 20 nt, from about 6 nt to about 15 nt, from about 8 nt to about 40 nt, from about 8 nt to about 30 nt, from about 8 nt to about 25 nt, from about 8 nt to about 20 nt or from about 8 nt to about 15 nt, from about 15 nt to about 150 nt, from about 15 nt to about 130 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt. In some embodiments, a tracrRNA sequence has a length of approximately 14 nucleotides. A tracrRNA sequence can be at least about 60% identical to a reference tracrRNA sequence (e.g., wild type tracrRNA sequence from S. pyogenes) over a stretch of at least 6, 7, or 8 contiguous nucleotides. For example, a tracrRNA sequence can be at least about 60% identical, at least about 65% identical, at least about 70% identical, at least about 75% identical, at least about 80% identical, at least about 85% identical, at least about 90%) identical, at least about 95% identical, at least about 98% identical, at least about 99% identical, or 100% identical, to a reference tracrRNA sequence (e.g., wild type tracrRNA sequence from S. pyogenes) over a stretch of at least 6, 7, or 8 contiguous nucleotides.

A tracrRNA sequence can comprise more than one duplexed region (e.g., hairpin, hybridized region). A tracrRNA sequence can comprise two duplexed regions. A tracrRNA may comprise a secondary structure. A tracrRNA may contain more than one secondary structure. In certain embodiments, a tracrRNA sequence may comprise a first secondary structure and a second secondary structure and a first secondary structure comprises more nucleotides than a second secondary structure. In certain embodiments, a tracrRNA may comprise a first secondary structure, a second secondary structure, and a third secondary structure and said first secondary structure comprises less nucleotides than said second secondary structure and said second secondary structure comprises more nucleotides than said third secondary structure. The number of secondary structures and corresponding nucleotide lengths is not particularly limited.

Figure 9:
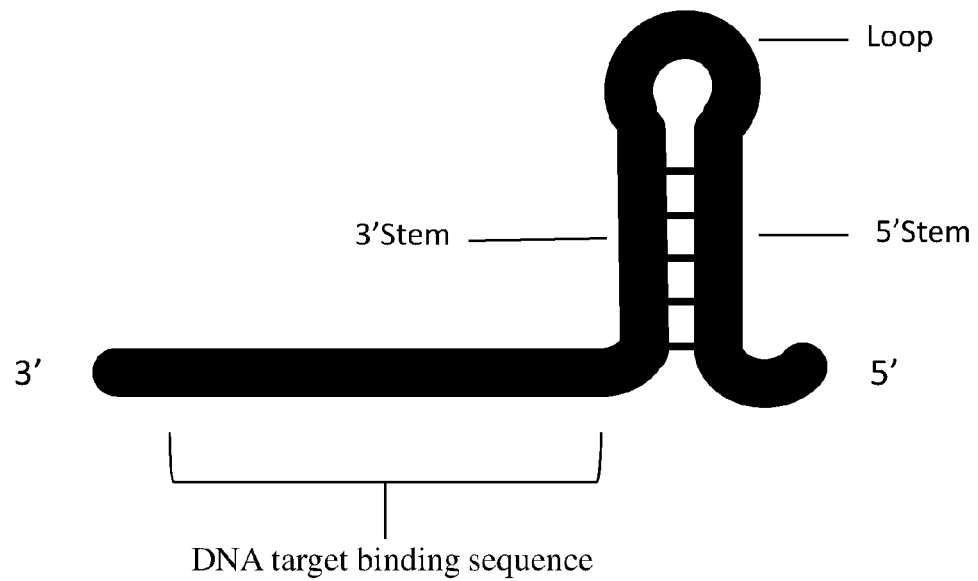
FIG. 9 shows a typical structure of a crRNA from a Type V CRISPR system.

Naturally occurring Type V CRISPR systems, unlike Type II CRISPR systems, do not require a tracrRNA for crRNA maturation and cleavage of a target nucleic acid. FIG. 9 shows a typical structure of a crRNA from a Type V CRISPR system, wherein the DNA target-binding sequence is downstream of a stem loop structure that interacts with the Cpf1 protein. Alterations of the nucleotides in the loop region do not affect Cpf1 cleavage activity.

FIGS. 10A-C show possible structures of a single guide D(R)NA of the present disclosure for use with a Type V CRISPR system. In these configurations, the solid black regions represent RNA, whereas the checkered regions represent DNA. FIG. 10A shows a single guide D(R)NA wherein the targeting region comprises RNA, the 3' stem comprises DNA, and the loop and 5' stem comprise RNA. FIG. 10B shows a single guide D(R)NA wherein the targeting region comprises RNA, the 5' stem comprises DNA, and the loop and 3' stem comprise RNA. FIG. 10C shows a single guide D(R)NA wherein the targeting region and loop comprise RNA, and the 5' and 3' stems comprise DNA. The 3' stem and 5' stem in FIGS. 10A-C collectively, or individually, may be referred to herein as the "activating region" of a polynucleotide for use with a Type V system.

Figure 11E:
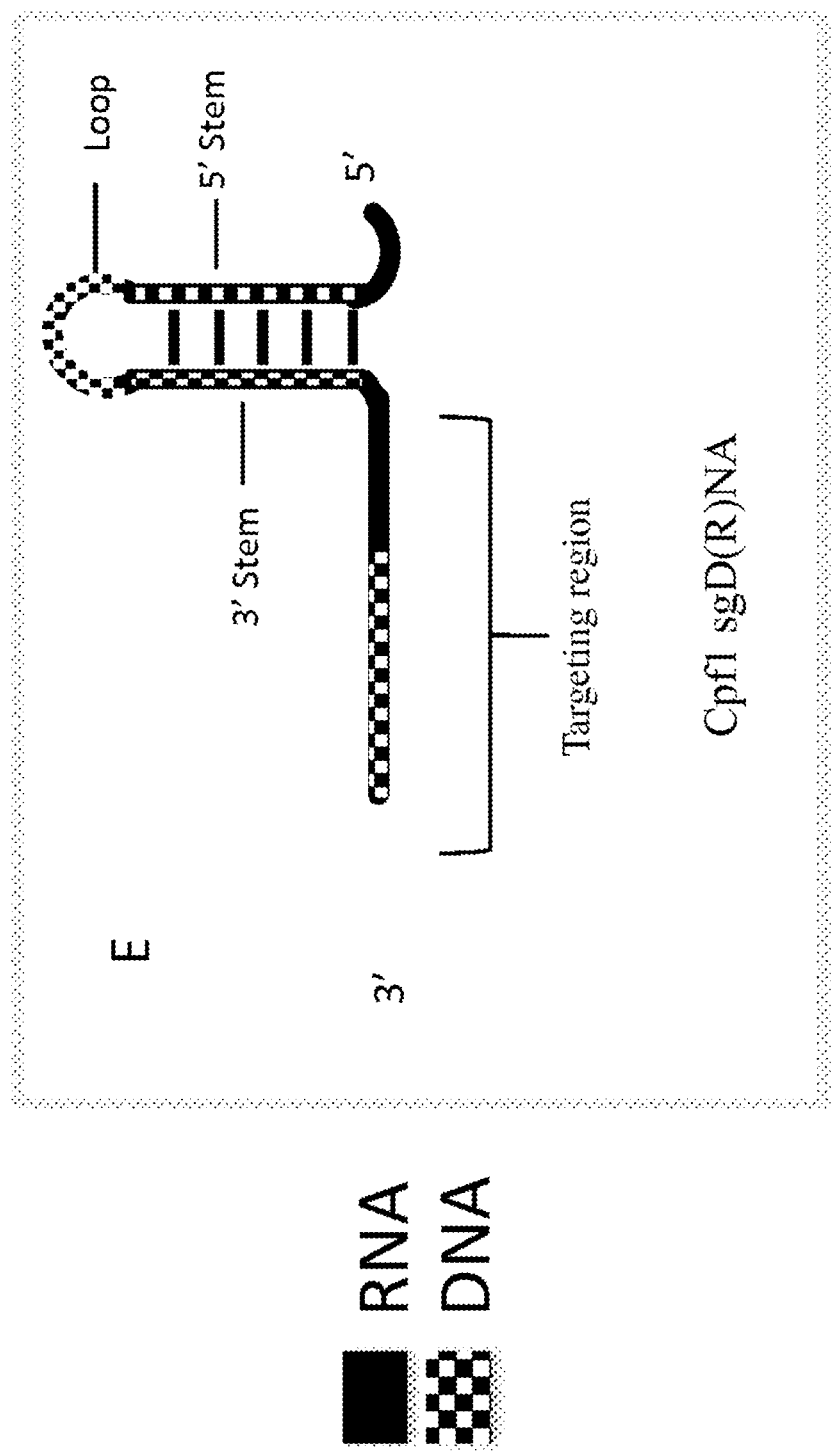

FIGS. 11A-E show possible structures of a single guide D(R)NA of the present disclosure for use with a Type V CRISPR system. In these configurations, the solid black regions represent DNA, whereas the checkered regions represent RNA. FIG. 11A shows a single guide D(R)NA wherein the targeting region comprises DNA, the 3' stem comprises DNA, and the loop and 5' stem comprise RNA. FIG. 11B shows a single guide D(R)NA wherein the targeting region comprises DNA, the 5' stem comprises DNA, and the loop and 3' stem comprise RNA. FIG. 11C shows a single guide D(R)NA wherein the targeting region, the 5' stem and 3' stem comprise DNA and the loop comprises RNA. FIG. 11D shows a single guide D(R)NA wherein the targeting region comprises DNA and the 5' stem, the 3' stem, and the loop comprise DNA. FIG. 11E shows a single guide D(R)NA wherein the targeting region comprises a mixture of DNA and RNA and the 5' stem, the 3' stem, and the loop comprise DNA. The 3' stem and 5' stem in FIGS. 11A-E collectively, or individually, may be referred to herein as the "activating region" of a polynucleotide for use with a Type V system.

FIGS. 12A-I show possible configurations of the crRNA and crD(R)NA of the present disclosure for use with a Type V CRISPR system wherein the 3' element and 5' element are on separate polynucleotides and associate through hydrogen base pair interactions to form a duplex or stem structure. FIG. 12A shows a dual guide system for use in a Type V CRISPR system, wherein the targeting region is linked to a 3' element. A second polynucleotide is also shown in FIG. 12A as a 5' element. The 5' element is configured to hybridize to the 3' element that is linked to the targeting region to form a duplex, or stem. In FIG. 12A the targeting region, 3' element, and 5' element comprise RNA. FIG. 12B shows a 5' element that comprises RNA. FIG. 12C shows a 5' element that comprises DNA. FIG. 12D shows a targeting region that comprises RNA and a 3' element that comprises RNA. FIG. 12E shows a targeting region that comprises RNA and a 3' element that comprises DNA. FIG. 12F shows a targeting region that comprises DNA and a 3' element that comprises RNA. FIG. 12G shows a targeting region that comprises DNA and a 3' element that comprises DNA. FIG. 12H shows a targeting region that comprises RNA and DNA and a 3' element that comprises DNA. FIG. 12I shows a targeting region that comprises an alternative mixture of RNA and DNA and a 3' element that comprises DNA. The 3' element in FIGS. 12A-I may be referred to herein as the "activating region" of a polynucleotide for use with a Type V system.

FIGS. 13A-H show possible configurations of the crRNA and crD(R)NA of the present disclosure for use with a Type V CRISPR system wherein the 3' element and 5' element are on separate polynucleotides and associate through hydrogen base pair interaction interactions to form a duplex or stem structure. In some embodiments of the polynucleotides shown in FIGS. 10A-13H, the regions of DNA may also comprise RNA. In some embodiments, the regions of RNA may also comprise DNA. In some embodiments, the regions of DNA may also comprise RNA and the regions of RNA may also comprise DNA. The 3' element in FIGS. 13A-H may be referred to herein as the "activating region" of a polynucleotide for use with a Type V system. The proportions of DNA and RNA in the various regions of the polynucleotides shown in FIGS. 10A-13H may vary. In certain embodiments, this apportionment may be 5%, 10%, 15%, 20%, 25%, 30%, 35%, 40%, 45%, 50%, 55%, 60%, 65%, 70%, 75%, 80%, 85%, 90%, 95%, or 100% RNA and ranges there between. Examples of polynucleotides that can be used with a Type V CRISPR system are provided in SEQ ID NOs: 168-203.

An activating region of a nucleic acid-targeting polynucleotide can interact with a region of a site-directed polypeptide. An activating region can interact with a plurality of regions of a site-directed polypeptide. An activating region can interact with a plurality of regions of a site-directed polypeptide wherein at least one of the regions interacts with a PAM of a target nucleic acid. Examples of these regions can include amino acids 1096-1225, and 1105-1138 of Cas9 in *S. pyogenes*.

Nucleotides adjacent to an unpaired nucleotide can be a nucleotide that forms a wobble base pairing interaction. Wobble base pairing interactions can include guanine-uracil, hypoxanthine-uracil, hypoxanthine-adenine, and hypoxanthine-cytosine. Wobble base pairing interactions may lead to reduced target and/or cleavage specificity. At least 1, 2, 3, 4, or 5 or more nucleotides adjacent to an unpaired nucleotide can form a wobble pairing. At most 1, 2, 3, 4, or 5 or more nucleotides adjacent to an unpaired nucleotide can form a wobble pairing. In certain embodiments, a targeting region may comprise a deoxyribonucleotide thymine ("dT") as a substitute to a ribonucleotide uracil. Using dT in place of U reduces wobble pairing and reduces off-target base-pairing, thus leading to increased target specify in certain embodiments.

A target nucleic acid can be comprised of DNA, RNA, or combinations thereof and can be a double-stranded nucleic acid or a single-stranded nucleic acid. A targeting region sequence can hybridize to a target nucleic acid that is located 5' or 3' of a protospacer adjacent motif (PAM), depending upon the particular site-directed polypeptide to be used. A PAM can vary depending upon the site-directed polypeptide to be used. For example, when using the Cas9 from *S. pyogenes*, the PAM can be a sequence in the target nucleic acid that comprises the sequence 5'-NRR-3', wherein R can be either A or G, wherein N is any nucleotide, and N is immediately 3' of the target nucleic acid sequence targeted by the targeting region sequence. A site-directed polypeptide may be modified such that a PAM may be different compared to a PAM for an unmodified site-directed polypeptide. For example, when using Cas9 from *S. pyogenes*, the Cas9 may be modified such that the PAM no longer comprises the sequence 5'-NRR-3', but instead comprises the sequence 5'-NNR-3', wherein R can be either A or G, wherein N is any nucleotide, and N is immediately 3' of the target nucleic acid sequence targeted by the targeting region sequence. Other site-directed polypeptides may recognize other PAMs and one of skill in the art is able to determine the PAM for any particular site-directed polypeptide. For example, Cpf1 from *Francisella novicida* was identified as having a 5'-TTN-3' PAM (Zetsche et al. (Cell; 163 (3):759-71 (2015))), but this was unable to support site specific cleavage of a target nucleic acid in vivo. Given the similarity in the guide sequence between *Francisella novicida* and other Cpf1 proteins, such as the Cpf1 from *Acidaminocccus* sp BV3L6, which utilize a 5'-TTN-3' PAM, it is more likely that the *Francisella novicida* Cpf1 protein recognizes and cleaves a site on a target nucleic acid proximal to a 5'-TTTN-3' PAM with greater specificity and activity than a site on a target nucleic acid proximal to the truncated 5'-TTN-3' PAM misidentified by Zetsche et al. The polynucleotides and CRISPR systems described in the present application may be used with a Cpf1 protein (e.g., from *Francisella novicida*) directed to a site on a target nucleic acid proximal to a 5'-TTTN-3' PAM.

A target nucleic acid sequence can be 20 nucleotides. A target nucleic acid can be less than 20 nucleotides. A target nucleic acid can be at least 5, 10, 15, 16, 17, 18, 19, 20, 21, 22, 23, 24, 25, 30 or more nucleotides. A target nucleotide can comprise ranges of nucleotides between about 5-30, and ranges between. For example, in a sequence comprising 5'-NNNNNNNNNNNNNNNNNNNNXRR-3', a target nucleic acid can be a sequence that corresponds to the N's, wherein N is any nucleotide and wherein X is the first nucleotide of the PAM recognized by *S. pyogenes*. The selection of a specific PAMs is within the knowledge of those of skill in the art based on the particular site-directed polypeptide to be used in a given instance.

The polynucleotides of the present disclosure comprising DNA and RNA on the same strand cannot be made in vivo using expression vectors, but can be chemically synthesized in vitro. Chemical synthesis of polynucleotides is well understood by one of ordinary skill in the art. Chemical synthesis of polynucleotides of the present disclosure can be conducted in solution or on a solid support. Synthesis in solution is preferred for large quantities and for higher purity polynucleotides, as the intermediates are purified following each step. For smaller quantities, where sequence purity is not as critical, solid phase synthesis is the preferred method. Polynucleotides of the present disclosure can also be obtained from commercial sources that provide automated chemical synthesis of polynucleotides.

Chemical synthesis of DNA may be easier, quicker and cheaper than the chemical synthesis of RNA. The generation and testing of polynucleotides comprising DNA can be more rapid and cost effective compared with RNA-comprising sequences. Sequences containing DNA may provide the advantage of increased specificity of targeting target nucleic acids such as DNA. Polynucleotides comprising DNA in specific regions as discussed herein may further present the advantage of reducing off-target binding because of the reduction in propensity for wobble base pairing associated with deoxyribonucleic acid bases compared to ribonucleic acid bases (e.g., thymidine bases in DNA compared to uracil bases in RNA).

In some embodiments, the polynucleotides of the present disclosure may also comprise modifications that, for example, increase stability of the polynucleotide. Such modifications may include phosphorothioates, chiral phosphorothioates, phosphorodithioates, phosphotriesters, aminoalkylphosphotriesters, methyl and other alkyl phosphonates such as 3'-alkylene phosphonates, 5'-alkylene phosphonates, chiral phosphonates, phosphinates, phosphoramidates including 3'-amino phosphoramidate and amino alkylphosphoramidates, phosphorodiamidates, thionophosphoramidates, thionoalkylphosphonates, thionoalkylphosphotriesters, selenophosphates, and boranophosphates having normal 3'-5' linkages, 2-5' linked analogs, and those having inverted polarity wherein one or more internucleotide linkages is a 3' to 3', a 5' to 5' or a 2' to 2' linkage. Suitable nucleic acid-targeting polynucleotides having inverted polarity can comprise a single 3' to 3' linkage at the 3'-most internucleotide linkage (i.e. a single inverted nucleoside residue in which the nucleobase is missing or has a hydroxyl group in place thereof). Various salts (e.g., potassium chloride or sodium chloride), mixed salts, and free acid forms can also be included.

In some embodiments, the polynucleotides of the present disclosure may also contain other nucleic acids, or nucleic acid analogues. An example of a nucleic acid analogue is peptide nucleic acid (PNA).

Delivery of polynucleotides of the present disclosure to cells, in vitro, or in vivo, may be achieved by a number of methods known to one of skill in the art. These methods include lipofection, electroporation, nucleofection, microinjection, biolistics, liposomes, immunoliposomes, polycation or lipid:nucleic acid conjugates. Lipofection is well known and described in e.g., U.S. Pat. Nos. 5,049,386, 4,946,787; and 4,897,355; and lipofection reagents are sold commercially. Cationic and neutral lipids that are suitable for efficient receptor-recognition lipofection of polynucleotides are described in International Publication Nos. WO 91/17424 and WO 91/16024.

Lipid:nucleic acid complexes, including targeted liposomes such as immunolipid complexes, and the preparation of such complexes is well known to one of skill in the art (see, e.g., Crystal, Science 270:404-410 (1995); Blaese et al., Cancer Gene Ther. 2:291-297 (1995): Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183; 4,217,344; 4,235,871; 4,261,975; 4,485,054; 4,501,728; 4,774,085; 4,837,028; and 4,946,787).

Electroporation can be used to deliver the polynucleotides of the present disclosure. Electroporation may also be used to deliver complexes of the site-directed polypeptide and polynucleotides of the present disclosure. In these methods, the polynucleotides, or the complexes of site-directed polypeptides and polynucleotides are mixed in an electroporation buffer with the target cells to form a suspension. This suspension is then subjected to an electrical pulse at an optimized voltage, which creates temporary pores in the phospholipid bilayer of the cell membrane, permitting charged molecules like DNA and proteins to be driven through the pores and into the cell. Reagents and equipment to perform electroporation are sold commercially.

Biolistic, or microprojectile delivery, can be used to deliver the polynucleotides of the present disclosure. In these methods, microprojectiles, such as gold or tungsten, are coated with the polynucleotide by precipitation with calcium chloride, spermidine or polyethylene glycol. The microprojectile particles are accelerated at high speed into a cell using a device such as the BIOLISTIC® PDS-1000/He Particle Delivery System (Bio-Rad; Hercules, Calif.).

In some embodiments, the present disclosure provides for methods of modifying a target gene in cell. The cell can be from any organism (e.g., a bacterial cell, an archaeal cell, a cell of a single-cell eukaryotic organism, a plant cell, an algal cell, a fungal cell (e.g., a yeast cell), a cell from an invertebrate animal, a cell from a vertebrate animal, or a cell from a mammal, including a cell from a human.

In some embodiments, the present disclosure provides for methods of modifying a target gene in a plant. As used herein, the term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to roots, stems, shoots, leaves, pollens, seeds, tumor tissue and various forms of cells and culture (e.g., single cells, protoplasts, embryos, and callus tissue).

The following examples are not intended to limit the scope of what the inventors regard as various aspects of the present invention.

EXAMPLE 1

Production of Guide RNA Components

Guide RNAs (e.g., sgRNAs and tracrRNAs) were produced by in vitro transcription (e.g., T7 Quick High Yield RNA Synthesis Kit, New England Biolabs, Ipswich, Mass.) from double-stranded DNA template incorporating a T7 promoter at the 5' end of the DNA sequences.

The double-stranded DNA template for the RNA components was assembled by PCR using 3' overlapping primers containing the corresponding DNA sequences to RNA components. The oligonucleotides used in the assembly are presented in Table 1.

TABLE 1

| Overlapping Primers for Generation of Guide RNA Templates | | |
|---|---|---|
| Type of Guide RNA | Target for DNA-binding Sequence | SEQ ID NO |
| sgRNA-AAVS | AAVS-1 (adeno-associated virus integration site 1 - human genome) | SEQ ID NO: 63, 64, 65, 66, 67 |

TABLE 1-continued

| Overlapping Primers for Generation of Guide RNA Templates | | |
|---|---|---|
| Type of Guide RNA | Target for DNA-binding Sequence | SEQ ID NO |
| tracrRNA | n/a | SEQ ID NO: 63, 71, 72, 73, 74 |

Oligonucleotide sequences (e.g., primer sequences shown in SEQ ID NOs 63-122) were provided to commercial manufacturers for synthesis (Integrated DNA Technologies, Coralville, Iowa; or Eurofins, Luxembourg).

The DNA primers were present at a concentration of 2 nM each. Two outer DNA primers corresponding to the T7 promoter (forward primer: SEQ ID NO. 63, Table 1), and the 3'end of the RNA sequence (reverse primers: SEQ ID NO 67 and 74, Table 1) were used at 640 nM to drive the amplification reaction. PCR reactions were performed using Q5 Hot Start High-Fidelity 2× Master Mix (New England Biolabs, Ipswich, Mass.) following the manufacturer's instructions. PCR assembly reactions were carried out using the following thermal cycling conditions: 98° C. for 2 minutes, 35 cycles of 15 seconds at 98° C., 15 seconds at 62° C., 15 seconds at 72° C., and a final extension at 72° C. for 2 min. DNA quality was evaluated by agarose gel electrophoresis (1.5%, SYBR® Safe, Life Technologies, Grand Island, N.Y.).

Between 0.25-0.5 µg of the DNA template for the guide RNA components were transcribed using T7 High Yield RNA synthesis Kit (New England Biolabs, Ipswich, Mass.) for ~16 hours at 37° C. Transcription reactions were treated with DNase I (New England Biolabs, Ipswich, Mass.) and purified using GeneJet RNA cleanup and concentration kit (Life Technologies, Grand Island, N.Y.). RNA yield was quantified using the Nanodrop™ 2000 system (Thermo Scientific, Wilmington, Del.). The quality of the transcribed RNA was checked by agarose gel electrophoresis (2%, SYBR® Safe, Life Technologies, Grand Island, N.Y.). The guide RNA components sequences are shown in Table 2.

TABLE 2

| Guide RNA Sequences | | | |
|---|---|---|---|
| Name | Sequence (RNA bases are bracketed) | | SEQ ID NO. |
| AAVS1 sgRNA | 5'-[G][G][G][G][C][C][A][C][U][A][G][G][G][A][C][A][G][G][A][U][G][U][C][U][C][A][G][A][G][C][U][A][U][G][C][U][G][U][C][C][U][G][G][A][A][A][C][A][G][G][A][C][A][G][C][A][U][A][G][C][A][A][G][U][U][G][A][G][A][U][A][A][G][G][C][U][A][G][U][C][C][G][U][U][A][U][C][A][A][C][U][U][G][A][A][A][A][A][G][U][G][G][C][A][C][C][G][A][G][U][C][G][G][U][G][C][U][U][U][U][U]-3' | | SEQ ID NO: 1 |
| tracrRNA | 5'-[G][C][A][G][G][A][C][A][G][C][A][U][A][G][C][A][A][G][U][U][G][A][G][A][U][A][A][G][G][C][U][A][G][U][C][C][G][U][U][A][U][C][A][A][C][U][U][G][A][A][A][A][A][G][U][G][G][C][A][C][C][G][A][G][U][C][G][G][U][G][C][U][U]-3' | | SEQ ID NO: 2 |

The method described above for production of guide RNA components can be applied to the production of other RNA components as described herein.

EXAMPLE 2

Production of Double-Stranded DNA Target Regions for Use in Cas9 Cleavage Assays Target double stranded DNA for use in an in vitro Cas cleavage assays were produced using PCR amplification of the target region from genomic DNA.

Double-stranded DNA target regions (e.g., AAVS-1) for biochemical assays were amplified by PCR from phenol-chloroform prepared human cell line K562 (ATCC, Manassas, Va.) genomic DNA (gDNA). PCR reactions were carried out with Q5 Hot Start High-Fidelity 2× Master Mix (New England Biolabs, Ipswich, Mass.) following the manufacturer's instructions. 20 ng/µL gDNA in a final volume of 25 µl were used to amplify the selected target region under the following conditions: 98° C. for 2 minutes, 35 cycles of 20 s at 98° C., 20 s at 60° C., 20 s at 72° C., and a final extension at 72° C. for 2 min. PCR products were purified using Spin Smart™ PCR purification tubes (Denville Scientific, South Plainfield, N.J.) and quantified using Nanodrop™ 2000 UV-Vis spectrophotometer (Thermo Scientific, Wilmington, Del.).

The forward and reverse primers used for amplification of selected targeted sequences from gDNA were as follows. The primers, amplicon size, and sizes of fragments generated from Cas9 mediated cleavage are shown in Table 3.

TABLE 3

Double-stranded DNA Targets

| Double-stranded Target | Amplicon Size | Cleavage Fragment Sizes | SEQ ID NO: |
|---|---|---|---|
| AAVS-1 target 1 | 495 bp | 316 bp/179 bp | SEQ ID NO: 75, 76 |
| EMX1 target 1 | 282 bp | 153 bp/129 bp | SEQ ID NO: 77, 78 |
| VEGFA target 1 | 276 bp | 112 bp/164 bp | SEQ ID NO: 79, 80 |
| CD34 target 1 | 282 bp | 111 bp/171 bp | SEQ ID NO: 81, 82 |
| CD34 target 2 | 268 bp | 108 bp/160 bp | SEQ ID NO: 83, 84 |
| STAT5a target 1 | 288 bp | 152 bp/136 bp | SEQ ID NO: 85, 86 |
| STAT5a target 2 | 242 bp | 103 bp/139 bp | SEQ ID NO: 87, 88 |
| JAK1 target 1 | 310 bp | 179 bp/131 bp | SEQ ID NO: 89, 90 |
| JAK1 target 2 | 310 bp | 178 bp/132 bp | SEQ ID NO: 91, 92 |

Other suitable double-stranded DNA target regions are obtained using essentially the same method. For non-human target regions, genomic DNA from the selected organism (e.g., plant, bacteria, yeast, algae) is used instead of DNA derived from human cells. Furthermore, polynucleotide sources other than genomic DNA can be used (e.g., vectors and gel isolated DNA fragments).

EXAMPLE 3

Cas9 Cleavage Assays

This example illustrates the use of a crD(R)NA of the present disclosure in in vitro Cas9 cleavage assays to evaluate and compare the percent cleavage of selected crD(R)NA/tracrRNA/Cas9 protein complexes relative to selected double-stranded DNA target sequences.

The cleavage activity was determined for a collection of crD(R)NAs variants (SEQ ID NOs: 38-62) against a double-stranded DNA target (AAVS-1; Example 2, Table 3).

Each sgRNA, crDNA or crD(R)NA was mixed with tracrRNA (if appropriate) in equimolar amounts in an annealing buffer (1.25 mM HEPES, 0.625 mM $MgCl_2$, 9.375 mM KCl at pH7.5), incubated for 2 minutes at 95° C., removed from thermocycler and allowed to equilibrate to room temperature.

The sgRNA, crDNA/tracrRNA, and crD(R)NA/tracrRNA were added to a Cas9 reaction mix. The Cas9 reaction mix comprised Cas9 protein diluted to a final concentration of 200 µM in reaction buffer (20 mM HEPES, 100 mM KCl, 5 mM $MgCl_2$, 1 mM DTT, and 5% glycerol at pH 7.4). In the reaction mix, the final concentration of each crD(R)NA/tracrRNA was 500 nM in each reaction mix. Each reaction mix was incubated at 37° C. for 10 minutes. The cleavage reaction was initiated by the addition of target DNA to a final concentration of 15 nM. Samples were mixed and centrifuged briefly before being incubated for 15 minutes at 37° C. Cleavage reactions were terminated by the addition of Proteinase K (Denville Scientific, South Plainfield, N.J.) at a final concentration of 0.2 µg/µL and 0.44 mg/µl RNase A Solution (SigmaAldrich, St. Louis, Mo.).

Samples were incubated for 25 minutes at 37° C. and 25 minutes at 55° C. 12 µL of the total reaction were evaluated for cleavage activity by agarose gel electrophoresis (2%, SYBR® Gold, Life Technologies, Grand Island, N.Y.). For the AAVS-1 double-stranded DNA target, the appearance of DNA bands at ~316 bp and ~179 bp indicated that cleavage of the target DNA had occurred. Cleavage percentages were calculated using area under the curve values as calculated by FIJI (ImageJ; an open source Java image processing program) for each cleavage fragment and the target DNA, and dividing the sum of the cleavage fragments by the sum of both the cleavage fragments and the target DNA.

Figure 3:
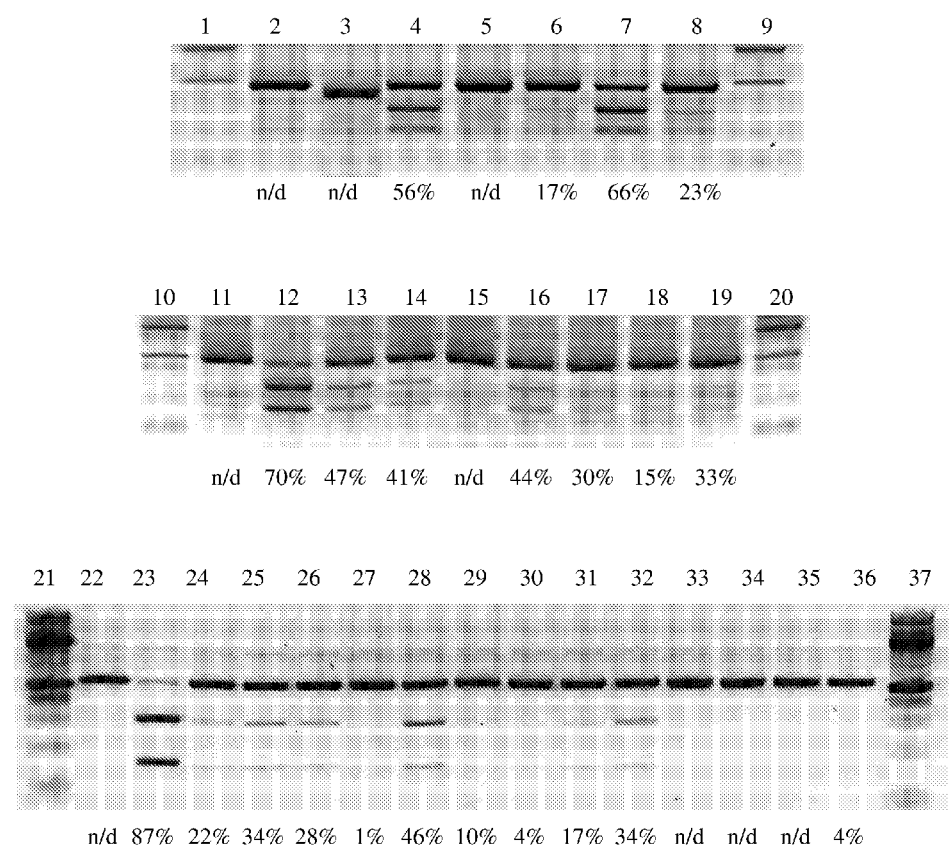
FIG. 3 shows cleavage of a target DNA sequence with a Type II CRISPR/Cas system using nucleic acid targeting polynucleotides of the present disclosure.

FIG. 3 presents the results of the Cas9 cleavage assay using the AAVS-1 target double-stranded DNA of sgRNA, crDNA/tracrRNA, and the crD(R)NA/tracrRNA. At the top of each panel is a lane number corresponding to the guide RNA component used, SEQ ID NOs corresponding to each component are shown in Table 4.

TABEL 4

| AAVS-1 crD(R)NA | |
|---|---|
| Lane | SEQ ID NO: |
| 1 | DNA Marker |
| 2 | No guide control |
| 3 | SEQ ID NO: 37 |
| 4 | SEQ ID NO: 38 |
| 5 | SEQ ID NO: 39 |
| 6 | SEQ ID NO: 40 |
| 7 | SEQ ID NO: 41 |
| 8 | SEQ ID NO: 42 |
| 9 | DNA Marker |
| 10 | DNA Marker |
| 11 | No guide control |
| 12 | SEQ ID NO: 1 |
| 13 | SEQ ID NO: 43 |
| 14 | SEQ ID NO: 44 |
| 15 | SEQ ID NO: 45 |
| 16 | SEQ ID NO: 46 |
| 17 | SEQ ID NO: 47 |
| 18 | SEQ ID NO: 48 |
| 19 | SEQ ID NO: 49 |
| 20 | DNA Marker |
| 21 | DNA Marker |
| 22 | No guide control |
| 23 | SEQ ID NO: 1 |
| 24 | SEQ ID NO: 50 |
| 25 | SEQ ID NO: 51 |
| 26 | SEQ ID NO: 52 |

TABEL 4-continued

AAVS-1 crD(R)NA

| Lane | SEQ ID NO: |
|---|---|
| 27 | SEQ ID NO: 53 |
| 28 | SEQ ID NO: 54 |
| 29 | SEQ ID NO: 55 |
| 30 | SEQ ID NO: 56 |
| 31 | SEQ ID NO: 57 |
| 32 | SEQ ID NO: 58 |
| 33 | SEQ ID NO: 59 |
| 34 | SEQ ID NO: 60 |
| 35 | SEQ ID NO: 61 |
| 36 | SEQ ID NO: 62 |
| 37 | DNA Marker |

Cleavage percentages are shown at the bottom of each lane. For crDNA or crD(R)NAs where no cleavage activity was observed (e.g., FIG. 3, 3; FIG. 3, 5; FIG. 3, 15; FIG. 3, 33; FIG. 3, 34; FIG. 3, 35) cleavage activity is expressed as n/d (indicating that cleavage activity was not detected).

The data presented in FIG. 3 demonstrate that the crD(R) NAs of the present disclosure facilitate Cas9 mediated site-specific cleavage of a target double-stranded DNA.

EXAMPLE 4 crD(R)NA Activity Against Multiple Targets

This example demonstrates the in vitro biochemical activity of crD(R)NAs comprising different spaces programmed to target specific sequences.

The sequences of the crDNA, crRNA and crD(R)NA (shown in Table 5) were provided to a commercial manufacturer for synthesis.

TABLE 5 crDNA, crRNA, and crD(R)NA sequences

| Target | Guide RNA type | Sequences (RNA bases are bracketed) | SEQ ID NO |
|---|---|---|---|
| EMX1 target 1 | crDNA | 5'-GAGTCCGAGC AGAAGAAGAA GTCTCAGAGC TATGCTGTCC TG-3' | SEQ ID NO: 3 |
| VEGFA target 1 | crDNA | 5'-GGGTGGGGGG AGTTTGCTCC GTCTCAGAGC TATGCTGTCC TG-3' | SEQ ID NO: 4 |
| CD34 target 1 | crDNA | 5'-GTTTGTGTTT CCATAAACTG GTCTCAGAGC TATGCTGTCC TG-3' | SEQ ID NO: 5 |
| CD34 target 2 | crDNA | 5'-TCTGTGATAA CCTCAGTTTA GTCTCAGAGC TATGCTGTCC TG-3' | SEQ ID NO: 6 |
| STAT5a target 1 | crDNA | 5'-GGCCACTGTA GTCCTCCAGG GTCTCAGAGC TATGCTGTCC TG-3' | SEQ ID NO: 7 |
| STAT5a target 2 | crDNA | 5'-GTCCCCCAGC CGGTCAGCCA GTCTCAGAGC TATGCTGTCC TG-3' | SEQ ID NO: 8 |
| JAK1 target 1 | crDNA | 5'-GGCAGCCAGC ATGATGAGAC GTCTCAGAGC TATGCTGTCC TG-3' | SEQ ID NO: 9 |
| JAK1 target 2 | crDNA | 5'-GAGGAGCTCC AAGAAGACTG GTCTCAGAGC TATGCTGTCC TG-3' | SEQ ID NO: 10 |
| EMX1 target 1 | crRNA | 5'-[G][A][G][U][C][C][G][A][G][C] [A][G][A][A][G][A][A][G][A][A] [G][U][C][U][C][A][G][A][G][C] [U][A][U][G][C][U][G][U][C][C][U][G]-3' | SEQ ID NO: 11 |
| VEGFA target 1 | crRNA | 5'-[G][G][G][U][G][G][G][G][G][G] [A][G][U][U][U][G][C][U][C][C] [G][U][C][U][C][A][G][A][G][C] [U][A][U][G][C][U][G][U][C][C][U][G]-3' | SEQ ID NO: 12 |
| CD34 target 1 | crRNA | 5'-[G][U][U][U][G][U][G][U][U][U] [C][C][A][U][A][A][A][C][U][G] [G][U][C][U][C][A][G][A][G][C] [U][A][U][G][C][U][G][U][C][C][U][G]-3' | SEQ ID NO: 13 |
| CD34 target 2 | crRNA | 5'-[U][C][U][G][U][G][A][U][A][A] [C][C][U][C][A][G][U][U][U][A] [G][U][C][U][C][A][G][A][G][C] [U][A][U][G][C][U][G][U][C][C][U][G]-3' | SEQ ID NO: 14 |
| STAT5a target 1 | crRNA | 5'-[G][G][C][C][A][C][U][G][U][A] [G][U][C][C][U][C][C][A][G][G] [G][U][C][U][C][A][G][A][G][C] [U][A][U][G][C][U][G][U][C][C][U][G]-3' | SEQ ID NO: 15 |

TABLE 5-continued crDNA, crRNA, and crD(R)NA sequences

| Target | Guide RNA type | Sequences (RNA bases are bracketed) | SEQ ID NO |
|---|---|---|---|
| STAT5a target 2 | crRNA | 5'-[G][U][C][C][C][C][C][A][G][C][C][G][G][U][C][A][G][C][C][A][G][U][C][U][C][A][G][A][G][C][U][A][U][G][C][U][G][U][C][C][U][G]-3' | SEQ ID NO: 16 |
| JAK1 target 1 | crRNA | 5'-[G][G][C][A][G][C][C][A][G][C][A][U][G][A][U][G][A][G][A][C][G][U][C][U][C][A][G][A][G][C][U][A][U][G][C][U][G][U][C][C][U][G]-3' | SEQ ID NO: 17 |
| JAK1 target 2 | crRNA | 5'-[G][A][G][G][A][G][C][U][C][C][A][A][G][A][A][G][A][C][U][G][G][U][C][U][C][A][G][A][G][C][U][A][U][G][C][U][G][U][C][C][U][G]-3' | SEQ ID NO: 18 |
| EMX1 target 1 | crD(R)NA | 5'-GAGTCCGAGC AGAA[G][A][A][G][A][A][G][U][C][U][C][A]GAGC TATGCTGTCC TG-3' | SEQ ID NO: 19 |
| VEGFA target 1 | crD(R)NA | 5'-GGGTGGGGGG AGTT[U][G][C][U][C][C][G][U][C][U][C][A]GAGC TATGCTGTCC TG-3' | SEQ ID NO: 20 |
| CD34 target 1 | crD(R)NA | 5'-GTTTGTGTTT CCAT[A][A][A][C][U][G][G][U][C][U][C][A]GAGC TATGCTGTCC TG-3' | SEQ ID NO: 21 |
| CD34 target 2 | crD(R)NA | 5'-TCTGTGATAA CCTC[A][G][U][U][U][A][G][U][C][U][C][A]GAGC TATGCTGTCC TG-3' | SEQ ID NO: 22 |
| STAT5a target 1 | crD(R)NA | 5'-GGCCACTGTA GTCC[U][C][C][A][G][G][G][U][C][U][C][A]GAGC TATGCTGTCC TG-3' | SEQ ID NO: 23 |
| STAT5a target 2 | crD(R)NA | 5'-GTCCCCCAGC CGGT]C][A][G][C][C][A][G][U][C][U][C][A]GAGC TATGCTGTCC TG-3' | SEQ ID NO: 24 |
| JAK1 target 1 | crD(R)NA | 5'-GGCAGCCAGC ATGA[U][G][A][G][A][C][G][U][C][U][C][A]GAGC TATGCTGTCC TG-3' | SEQ ID NO: 25 |
| JAK1 target 2 | crD(R)NA | 5'-GAGGAGCTCC AAGA[A][G][A][C][U][G][G][U][C][U][C][A]GAGC TATGCTGTCC TG-3' | SEQ ID NO: 26 | tracrRNA was constructed as described in Example 1.

Double stranded DNA targets were generated as described in Example 2 using the oligonucleotides shown in Table 3 corresponding to the appropriate target sequence.

crDNA/tracrRNA, crRNA/tracrRNA, and crD(R)NA/tracrRNA were hybridized and biochemical cleavage is carried out as described in Example 3.

Figures 4A, 4B:
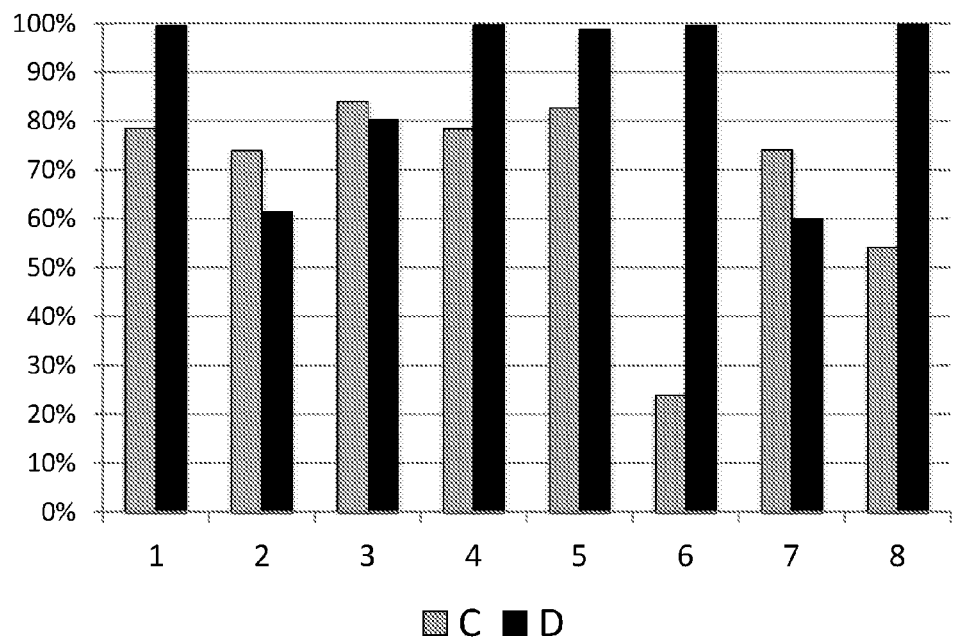
FIGS. 4A and B show results of in vitro biochemical assays to determine the amount of cleavage of various target sequences by a TYPE II CRISPR/Cas system using nucleic acid targeting polynucleotides of the present disclosure.

FIG. 4A and FIG. 4B show the results for the biochemical cleavage of various spacers. FIG. 4A shows biochemical cleavage percentages. Activity for EMX target 1 is shown in group 1: where 'A' is a Cas9 only control, 'B' is the crDNA/tracrRNA/Cas9, 'C' is the crRNA/tracrRNA/Cas9, and 'D' is the crD(R)NA/tracrRNA/Cas9. Activity for VEGFA target 1 is shown in group 2: where 'A' is a Cas9 only control, 'B' is the crDNA/tracrRNA/Cas9, 'C' is the crRNA/tracrRNA/Cas9, and 'D' is the crD(R)NA/tracrRNA/Cas9. Activity for CD34 target 1 is shown in group 3: where 'A' is a Cas9 only control, 'B' is the crDNA/tracrRNA/Cas9, 'C' is the crRNA/tracrRNA/Cas9, and 'D' is the crD(R)NA/tracrRNA/Cas9. Activity for CD34 target 2 is shown in group 4: where 'A' is a Cas9 only control, 'B' is the crDNA/tracrRNA/Cas9, 'C' is the crRNA/tracrRNA/Cas9, and 'D' is the crD(R)NA/tracrRNA/Cas9. Activity for STAT5a target 1 is shown in group 5: where 'A' is a Cas9 only control, 'B' is the crDNA/tracrRNA/Cas9, 'C' is the crRNA/tracrRNA/Cas9, and 'D' is the crD(R)NA/tracrRNA/Cas9. Activity for STAT5a target 2 is shown in group 6: where 'A' is a Cas9 only control, 'B' is the crDNA/tracrRNA/Cas9, 'C' is the crRNA/tracrRNA/Cas9, and 'D' is the crD(R)NA/tracrRNA/Cas9. Activity for JAK1 target 1 is shown in group 7; where 'A' is a Cas9 only control, 'B' is the crDNA/tracrRNA/Cas9, 'C' is the crRNA/tracrRNA/Cas9, and 'D' is the crD(R)NA/tracrRNA/Cas9. Activity for JAK1 target 2 is shown in group 8; where 'A' is a Cas9 only control, 'B' is the crDNA/tracrRNA/Cas9, 'C' is the crRNA/tracrRNA/Cas9, and 'D' is the crD(R)NA/tracrRNA/Cas9. For all Cas9 only samples (FIG. 4A, 'A') and crDNA/tracrRNA/cas9 samples (FIG. 4B, 'B'), no cleavage activity was detected (FIG. 4A, 'n/d').

In FIG. 4B, the percent cleavage is shown on the y-axis of the graph and the target is shown on the x-axis. Activity for EMX target 1 is shown in the bars of group 1. Activity for VEGFA target 1 is shown in the bars of group 2. Activity for CD34 target 1 is shown in the bars of group 3. Activity for CD34 target 2 is shown in the bars of group 4. Activity for STAT5a target 1 is shown in the bars of group 5. Activity for STAT5a target 2 is shown in the bars of group 6. Activity for JAK1 target 1 is shown in the bars of group 7. Activity for JAK1 target 2 is shown in the bars of group 8. 'C' and 'D' refer to the same reactions as in FIG. 4A.

FIG. 4 demonstrates that the Cas9 mediated biochemical cleavage of a double stranded DNA target using the crD(R)NA of the present disclosure is transferable across different target sequences.

EXAMPLE 5

T7E1 Assay for Detection of Target Modifications in Eukaryotic Cells

This example illustrates the use of T7E1 assays to evaluate the percent cleavage in vivo of crD(R)NA relative to selected double-stranded DNA target sequences.

A. Cell Transfections Using Cas Polynucleotide Components sgRNA and crD(R)NA/tracrRNAs comprising an AAVS-1 targeting sequence were transfected into HEK293 cells constitutively expressing SpyCas9-GFP fusion (HEK293-Cas9-GFP), using the Nucleofector® 96-well Shuttle System (Lonza, Allendale, N.J.) and the following protocol. Equal molar amounts of guide RNA components were prepared in an annealing buffer (1.25 mM HEPES, 0.625 mM MgCl$_2$, 9.375 mM KCl at pH 7.5), were incubated for 2 minutes at 95° C., were removed from thermocycler, allowed to equilibrate to room temperature, and dispensed in a 10 µL final volume in triplicate in a 96-well plate. Culture medium was aspirated from HEK293-Cas9-GFP cells, and the cells were washed once with calcium and magnesium-free PBS then were trypsinized by the addition of TrypLE (Life Technologies, Grand Island, N.Y.) followed by incubation at 37° C. for 3-5 minutes. Trypsinized cells were gently pipetted up and down to form a single cell suspension and added to DMEM complete culture medium composed of DMEM culture medium (Life Technologies, Grand Island, N.Y.) containing 10% FBS (Fisher Scientific, Pittsburgh, Pa.) and supplemented with penicillin and streptomycin (Life Technologies, Grand Island, N.Y.).

The cells were then pelleted by centrifugation for 3 minutes at 200×g, the culture medium aspirated and cells were resuspended in PBS. The cells were counted using the Countess® II Automated Cell Counter (Life Technologies, Grand Island, N.Y.). 2.2×10$^7$ cells were transferred to a 50 ml tube and pelleted. The PBS was aspirated and the cells were resuspended in Nucleofector™ SF (Lonza, Allendale, N.J.) solution to a density of 1×10$^7$ cells/mL. 20 µL of the cell suspension were then added to individual wells containing 10 uL of Cas polynucleotide components and the entire volume was transferred to the wells of a 96-well Nucleocuvette™ Plate (Lonza, Allendale, N.J.). The plate was loaded onto the Nucleofector™ 96-well Shuttle™ (Lonza, Allendale, N.J.) and cells were nucleofected using the 96-CM-130 Nucleofector™ program (Lonza, Allendale, N.J.). Post-nucleofection, 70 µL DMEM complete culture medium was added to each well and 50 µL of the cell suspension were transferred to a collagen coated 96-well cell culture plate containing 150 µL pre-warmed DMEM complete culture medium. The plate was then transferred to a tissue culture incubator and maintained at 37° C. in 5% CO$_2$ for 48 hours.

B. Target Double-Stranded DNA Generation for T7E1 Assay gDNA was isolated from HEK-293-SpyCas9 cells 48 hours after Cas polynucleotide component transfection using 50 µL QuickExtract DNA Extraction solution (Epicentre, Madison, Wis.) per well followed by incubation at 37° C. for 10 minutes, 65° C. for 6 minutes and 95° C. for 3 minutes to stop the reaction. gDNA was then diluted with 150 µL water and samples were stored at −80° C.

DNA for T7E1 was generated by PCR amplification of a target double-stranded DNA sequence (e.g., AAVS-1) from isolated gDNA. PCR reactions were set up using 8 µL gDNA as template with KAPA HiFi Hot Start polymerase and containing 0.5 U of polymerase, 1× reaction buffer, 0.4 mM dNTPs and 300 nM forward and reverse primers directed to the target double-stranded DNA (e.g., AAVS-1, SEQ ID NOs: 75, 76 (Table 3)) in a total volume of 25 uL. Target DNA was amplified using the following conditions: 95° C. for 5 minutes, 4 cycles of 20 s at 98° C., 20 s at 70° C., minus 2° C./cycle, 30 s at 72° C., followed by 30 cycles of 15 s at 98° C., 20 s at 62° C., 20 s at 72° C., and a final extension at 72° C. for 1 minute.

C. T7E1 Assay

PCR amplified target double-stranded DNA for T7E1 assays was denatured at 95° C. for 10 minutes and then allowed to re-anneal by cooling to 25° C. at −0.5° C./s in a thermal cycler. The re-annealed DNA was incubated with 0.5 mL T7 Endonuclease I in 1× NEBuffer 2 buffer (New England Biolabs, Ipswich, Mass.) in a total volume of 15 mL for 25 minutes at 37° C. T7E1 reactions were analyzed using the Fragment Analyzer™ system (Advanced Analytical Technologies, Inc., Ames, Iowa) and the DNF-910 double-stranded DNA Reagent Kit (Advanced Analytical Technologies, Inc., Ames, Iowa). The Fragment Analyzer™ system provides the concentration of each cleavage fragment and of the target double-stranded DNA that remains after cleavage.

Cleavage percentages of the target double-stranded DNA were calculated from the concentration of each cleavage fragment and the target double-stranded DNA, which remains after cleavage has taken place, using the following formula:

$$\% \text{ cleavage} = \left(1 - \sqrt{\left(1 - \frac{(frag1 + frag2)}{(frag1 + frag2 + parent)}\right)}\right) \quad \text{EQUATION 1}$$

In Equation 1, "frag1" and "frag2" concentrations correspond to the concentration of Cas cleavage fragments of the double-stranded DNA target and "parent" corresponds to the target double-stranded DNA that remains after cleavage has taken place.

Figure 5:
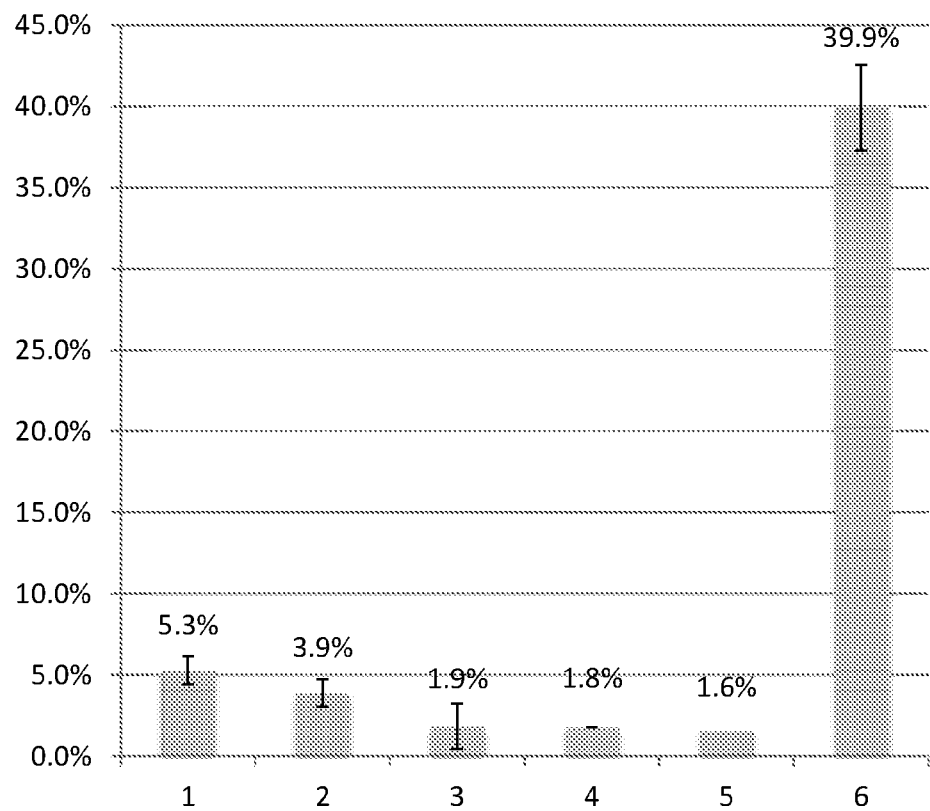
FIG. 5 shows results of in vivo assays to determine the amount of cleavage of a target sequence by a TYPE II CRISPR/Cas system using nucleic acid targeting polynucleotides of the present disclosure.

FIG. 5 shows the results of a T7E1 assay of gDNA prepped from cells transfected with crD(R)NAs at various concentrations. The average percent indels frequency detected was shown above each bar graph (calculated using Equation 1). The percent are the average of three samples, except for FIG. 5, bar 4, in which activity was only detected in two samples and FIG. 5, bar 5, in which activity was only detected in one sample. The concentration of either crD(R)NA/tracrRNA or sgRNA nucleofected into cells are shown in Table 6.

TABLE 6

Transfected Guide RNA Component Concentrations

| # | SEQ ID NO. | pmol |
|---|---|---|
| 1 | SEQ ID NO: 43 | 500 |
| 2 | SEQ ID NO: 43 | 750 |
| 3 | SEQ ID NO: 43 | 1000 |
| 4 | SEQ ID NO: 43 | 2000 |
| 5 | SEQ ID NO: 43 | 3000 |
| 6 | SEQ ID NO: 1 | 500 |

The T7E1 assay for detection of target modifications in eukaryotic cells provides data to demonstrate that the crD(R)NA/tracrRNA/Cas9 systems as described herein facilitate Cas-mediated site-specific in vivo cleavage of target double-stranded DNA.

Following the guidance describe herein, the T7E1 assay described in this example can be practiced by one of ordinary skill in the art to measure activity from cells modified with other CRISPR-Cas systems, including, but not limited to Cas9, Cas9-like, Cas1, Csn2, Cas4, Cpf1, C2c1, C2c2, C2c3, proteins encoded by Cas9 orthologs, Cas9-like synthetic proteins, Cas9 fusions, and variants and modifications thereof, combined with their cognate polynucleotide components modified as described herein to comprise a crD(R)NA.

EXAMPLE 6

On/Off-Target crD(R)NA Cleavage Activity

This example illustrates the use of crD(R)NAs to evaluate the cleavage activity of a target at the intended target site ("on-target") and predicted nearest neighbor ("off-target") sites. Target sequences of on/off-target sites are shown in Table 7:

TABLE 7

On/Off-Target Site Sequences

| Target | Site | Target Sequence | SEQ ID NO: |
|---|---|---|---|
| EMX-1 | ON | 5'-GAGTCCGAGCAGAAGAAGAA-3' | SEQ ID NO: 27 |
| EMX-1 | OFF1 | 5'-GAGTTAGAGCAGAAGAAGAA-3' | SEQ ID NO: 28 |
| EMX-1 | OFF2 | 5'-AGGTACTAGCAGAAGAAGAA-3' | SEQ ID NO: 29 |
| EMX-1 | OFF3 | 5'-ACGTCTGAGCAGAAGAAGAA-3' | SEQ ID NO: 30 |
| EMX-1 | OFF4 | 5'-AGGTGCTAGCAGAAGAAGAA-3' | SEQ ID NO: 31 |
| VEGFA-1 | ON | 5'-GGGTGGGGGGAGTTTGCTCC-3' | SEQ ID NO: 32 |

TABLE 7-continued

On/Off-Target Site Sequences

| Target | Site | Target Sequence | SEQ ID NO: |
|---|---|---|---|
| VEGFA-1 | OFF1 | 5'-GGATGGAGGGAGTTTGCTCC-3' | SEQ ID NO: 33 |
| VEGFA-1 | OFF2 | 5'-GGGGAGGGGAAGTTTGCTCC-3' | SEQ ID NO: 34 |
| VEGFA-1 | OFF3 | 5'-GGGAGGGTGGAGTTTGCTCC-3' | SEQ ID NO: 35 |
| VEGFA-1 | OFF4 | 5'-CGGGGGAGGGAGTTTGCTCC-3' | SEQ ID NO: 36 | crRNA and crD(R)NA sequences were provided to a commercial manufacturer for synthesis. tracrRNA were constructed as described in Example 1.

Double stranded DNA targets were generated as described in Example 2 using the oligonucleotides shown in Table 8 corresponding to the appropriate target sequence.

TABLE 8

On/Off-Target DNA

| Target | Site | Target Sequence |
|---|---|---|
| EMX-1 | on | SEQ ID Nos. 107, 108 |
| EMX-1 | OFF1 | SEQ ID Nos. 111, 112 |
| EMX-1 | OFF2 | SEQ ID Nos. 113, 114 |
| EMX-1 | OFF3 | SEQ ID Nos. 115, 116 |
| EMX-1 | OFF4 | SEQ ID Nos. 117, 118 |
| VEGFA-1 | on | SEQ ID Nos. 119, 120 |
| VEGFA-1 | OFF1 | SEQ ID Nos. 121, 122 |
| VEGFA-1 | OFF2 | SEQ ID Nos. 123, 124 |
| VEGFA-1 | OFF3 | SEQ ID Nos. 125, 126 |
| VEGFA-1 | OFF4 | SEQ ID Nos. 107, 108 | crRNA/tracrRNA and crD(R)NA/tracrRNA were hybridized and biochemical cleavage was carried out as described in Example 3.

Figure 6:
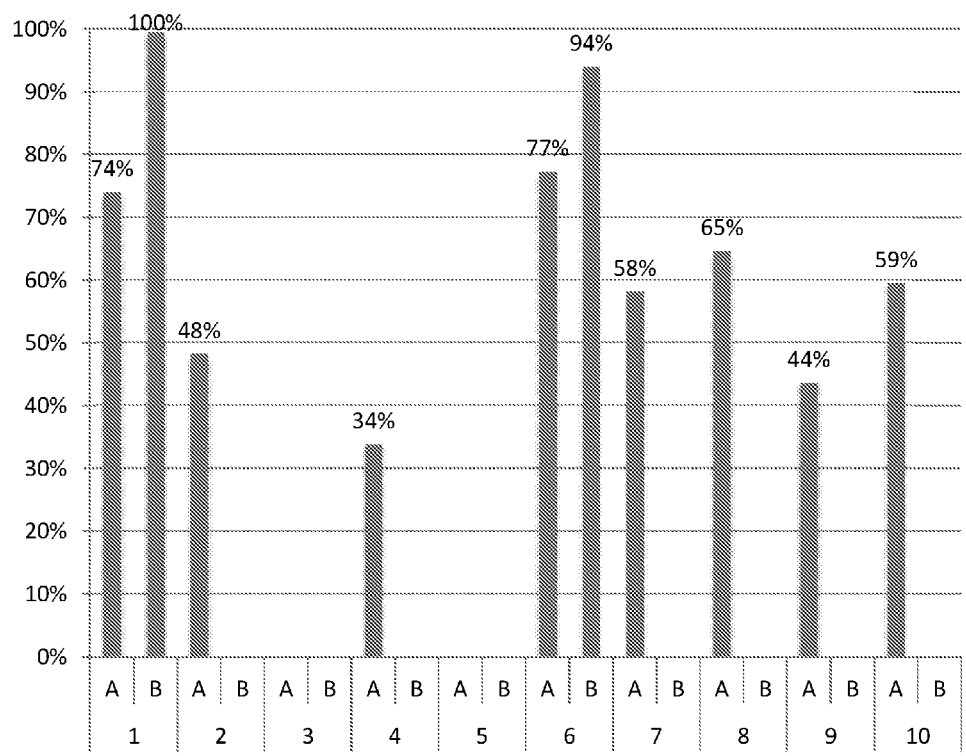
FIG. 6 shows results of in vitro biochemical assays to determine the amount of off-target cleavage of a target sequence by a TYPE II CRISPR/Cas system using nucleic acid targeting polynucleotides of the present disclosure.

FIG. 6 shows the comparison of biochemical activity of a crRNA/tracrRNA and crD(R)NA/tracrRNA at intended on-target sites and four computationally predicted off-target sites. Percent cleavage is shown on the y-axis and samples are shown on the x-axis. Table 9 lists the samples:

TABLE 9 crRNA and tracrRNA On/Off-target Activity

| ID | Target Site | Guide RNA Component |
|---|---|---|
| 1A | EMX-1 ON | crRNA |
| 1B | EMX-1 ON | crD(R)NA |
| 2A | EMX-1 OFF-1 | crRNA |
| 2B | EMX-1 OFF-1 | crD(R)NA |
| 3A | EMX-1 OFF-2 | crRNA |
| 3B | EMX-1 OFF-2 | crD(R)NA |
| 4A | EMX-1 OFF-3 | crRNA |
| 4B | EMX-1 OFF-3 | crD(R)NA |
| 5A | EMX-1 OFF-4 | crRNA |

TABLE 9-continued crRNA and tracrRNA On/Off-target Activity

| ID | Target Site | Guide RNA Component |
|---|---|---|
| 5B | EMX-1 OFF-4 | crD(R)NA |
| 6A | VEGFA-1 ON | crRNA |
| 6B | VEGFA-1 ON | crD(R)NA |
| 7A | VEGFA-1 OFF-1 | crRNA |
| 7B | VEGFA-1 OFF-1 | crD(R)NA |
| 8A | VEGFA-1 OFF-2 | crRNA |
| 8B | VEGFA-1 OFF-2 | crD(R)NA |
| 9A | VEGFA-1 OFF-3 | crRNA |
| 9B | VEGFA-1 OFF-3 | crD(R)NA |
| 10A | VEGFA-1 OFF-4 | crRNA |
| 10B | VEGFA-1 OFF-4 | crD(R)NA |

Figure 7:
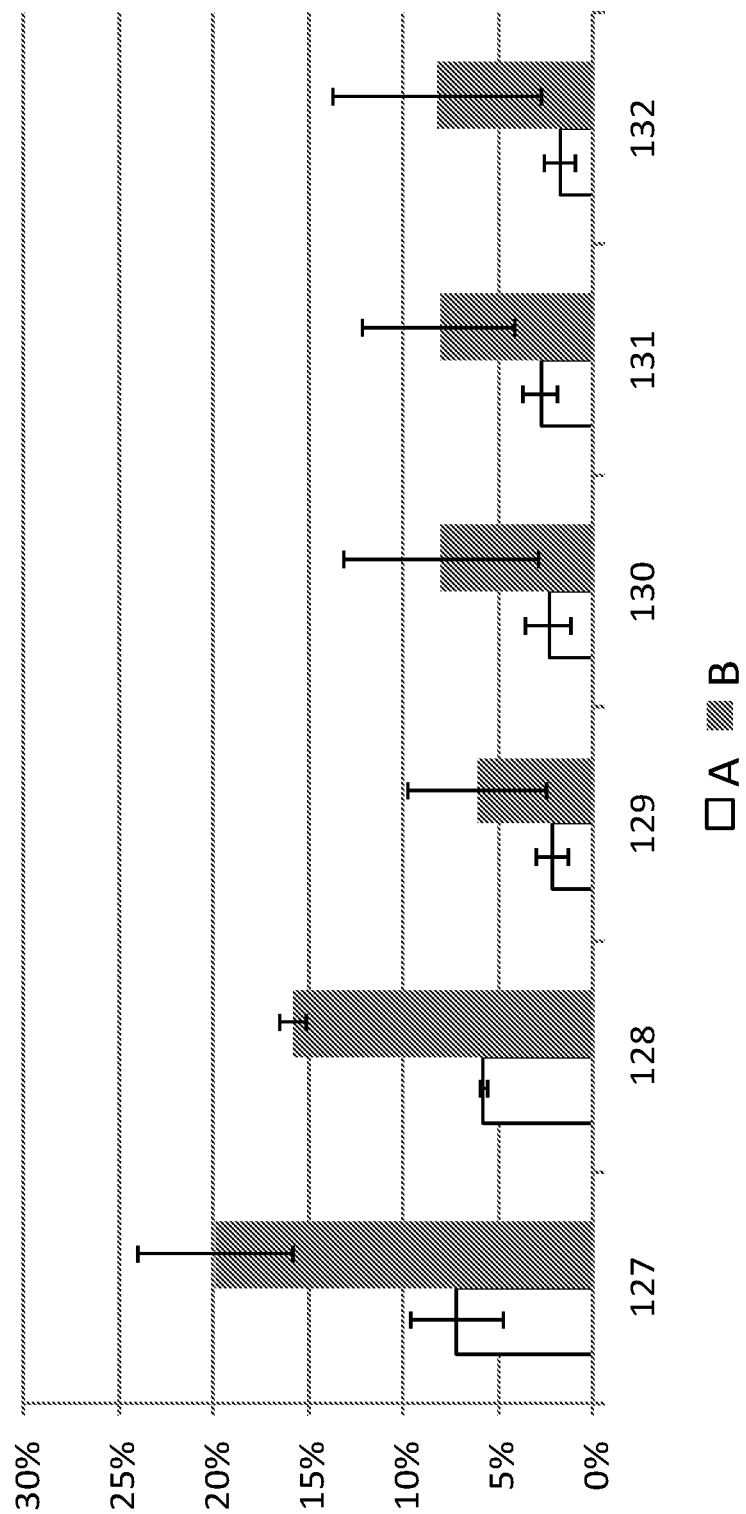
FIG. 7 shows results of an in vivo assay to determine the amount of cleavage of a target sequence by a TYPE II CRISPR/Cas system using nucleic acid targeting polynucleotides of the present disclosure.

The data presented in FIG. 7 show crD(R)NAs maintain high on-target activity when compared to crRNA. crD(R) NAs do not support off-target activity whereas the crRNAs have undesirable off-target activity.

EXAMPLE 7

Deep Sequencing Analysis for Detection of Target Modifications in Eukaryotic Cells This example illustrates the use of deep sequencing analysis to evaluate and compare the percent cleavage in vivo of selected sgD(R)NA/Cas9 protein complexes relative to selected double-stranded DNA target sequences.

A. Synthesis of sgD(R)NA

Six sgD(R)NA sequences targeting the human AAVS-1 locus and comprising different DNA/RNA compositions and phosphorothioate protected bonds were provided to a commercial manufacturer for synthesis. These sequences are shown in Table 10.

TABLE 10 sgD(R)NA Sequences

| Name | Sequence (RNA bases are bracketed, phosphorothioate bonds are shown with an *) | SEQ ID NO: |
|---|---|---|
| sgD(R)NA-01 | 5'-GGGGCCACTA GGGA[C][A][G][G][A][U] [G][U][U][U][U][A][G][A][G][C] [U][A][G][A][A][A][U][A][G][C] [A][A][G][U][U][A][A][A][A][U] [A][A][G][G][C][U][A][G][U][C] [C][G][U][U][A][U][C][A][A][C] [U][U][G][A][A][A][A][A][G][U] [G][G][C][A][C][C][G][A][G][U] [C][G][G][U][G][C][U]-3' | SEQ ID NO: 127 |
| sgD(R)NA-02 | 5'-G*G*GGCCACTA GGGA[C][A][G][G][A][U] [G][U][U][U][U][A][G][A][G][C] [U][A][G][A][A][A][U][A][G][C] [A][A][G][U][U][A][A][A][A][U] [A][A][G][G][C][U][A][G][U][C] [C][G][U][U][A][U][C][A][A][C] [U][U][G][A][A][A][A][A][G][U] [G][G][C][A][C][C][G][A][G][U] [C][G][G][U][G][C][U]-3' | SEQ ID NO: 128 |
| sgD(R)NA-03 | 5'-GGGGCCACTA GGGA[C][A][G][G][A][U] [G][U][U][U][U][A][G][A]GC TGCT[G][A][A][A]AGC AUAGC[A][A][G][U][U] [A][A][A][U][A][A][G][G][C] [U][A][G][U][C][C][G][U][U][A] [U][C][A][A][C][U][U][G][A][A] [A][A][A][G][U][G][G][C][A][C] [C][G][A][G][U][C][G][G][U][G][C][U]-3' | SEQ ID NO: 129 |
| sgD(R)NA-04 | 5'-G*G*GGCCACTA GGGA[C][A][G][G][A][U] [G][U][U][U][U][A][G][A]GC TATGCT[G][A][A][A]AGC ATAGC[A][A][G][U][U] [A][A][A][U][A][A][G][G][C] [U][A][G][U][C][C][G][U][U][A] [U][C][A][A][C][U][U][G][A][A] [A][A][A][G][U][G][G][C][A][C] [C][G][A][G][U][C][G][G][U][G][C][U]-3' | SEQ ID NO: 130 |
| sgD(R)NA-05 | 5'-GGGGCCACTA GGGA[C][A][G][G][A][U] [G][U][U][U][U][A][G][A]GC TATGCT[G][A][A][A]AGC ATAGC[A][A][G][U][U] [A][A][A][A][U][A][A][G][G][C] [U][A][G][U][C][C][G][U][U][A] | SEQ ID NO: 131 |

TABLE 10-continued sqD(R)NA Sequences

| Name | Sequence (RNA bases are bracketed, phosphorothioate bonds are shown with an *) | SEQ ID NO: |
|---|---|---|
| | [U][C][A][A][C][U][U][G][A][A]<br>[A][A][A][G][U][G][G]CAC<br>CG[A][G][U]CGGTG[C][U]-3' | |
| sgD(R)NA-06 | 5'-G*G*GGCCACTA<br>GGGA[C][A][G][G][A][U]<br>[G][U][U][U][U][A][G][A]GC<br>TATGCT[G][A][A][A]AGC<br>ATAGC[A][A][G][U][U]<br>[A][A][A][A][U][A][A][G][G][C]<br>[U][A][G][U][C][C][G][U][U][A]<br>[U][C][A][A][C][U][U][G][A][A]<br>[A][A][A][G][U][G][G]CAC<br>CG[A][G][U]CGGTG[C][U]-3' | SEQ ID NO: 132 |

B. Formation of RNP Complexes of sgD(R)NA/Cas9 Protein

Cas9 protein was expressed from a bacterial expression vector in E. coli (BL21 (DE3)) and purified using affinity ion exchange and size exclusion chromatography according to methods described in Jinek et al. (Science; 337 (6096):816-21 (2012)). The coding sequence for Streptococcus pyogenes Cas9 included two nuclear localization sequences (NLS) at the C-terminus. Ribonucleoprotein (RNP) complexes were assembled, in triplicate, at two concentrations, 20 pmol Cas9:60 pmols sgD(R)NA and 200 pmols Cas9:600 pmols sgD(R)NA. The sgD(R)NA components were mixed in equimolar amounts in an annealing buffer (1.25 mM HEPES, 0.625 mM $MgCl_2$, 9.375 mM KCl at pH7.5) to the desired concentration (60 pmols or 600 pmols) in a final volume of 5 µL, incubated for 2 minutes at 95° C., removed from the thermocycler and allowed to equilibrate to room temperature. Cas9 protein was diluted to an appropriate concentration in binding buffer (20 mM HEPES, 100 mM KCl, 5 mM $MgCl_2$, 1 mM DTT, and 5% glycerol at pH 7.4) to a final volume of 5 µL and mixed with the 5 µL of heat-denatured crD(R)NAs followed by incubation at 37° C. for 30 minutes.

C. Cell Transfections Using sgD(R)NA/Cas9 Protein RNPs

RNP complexes were transfected into K562 cells (ATCC, Manassas, Va.), using the Nucleofector® 96-well Shuttle System (Lonza, Allendale, N.J.) and the following protocol. RNP complexes were dispensed in a 10 µL final volume into individual wells of a 96-well plate. K562 cells suspended in media were transferred from a culture flask to a 50 mL conical tube. Cells were pelleted by centrifugation for 3 minutes at 200×g, the culture medium aspirated, and the cells were washed once with calcium and magnesium-free PBS. K562 cells were then pelleted by centrifugation for 3 minutes at 200×g, the PBS aspirated and cell pellet were resuspended in 10 mL of calcium and magnesium-free PBS.

The cells were counted using the Countess® II Automated Cell Counter (Life Technologies, Grand Island, N.Y.). 2.2× $10^7$ cells were transferred to a 50 ml tube and pelleted. The PBS was aspirated and the cells were resuspended in Nucleofector™ SF (Lonza, Allendale, N.J.) solution to a density of 1×$10^7$ cells/mL. 20 µL of the cell suspension were added to individual wells containing 10 µL of RNP complexes and the entire volume was transferred to the wells of a 96-well Nucleocuvette™ Plate (Lonza, Allendale, N.J.).

The plate was loaded onto the Nucleofector™ 96-well Shuttle™ (Lonza, Allendale, N.J.) and cells were nucleofected using the 96-FF-120 Nucleofector™ program (Lonza, Allendale, N.J.). Post-nucleofection, 70 µL Iscove's Modified Dulbecco's Media (IMDM; Life Technologies, Grand Island, N.Y.), supplemented with 10% FBS (Fisher Scientific, Pittsburgh, Pa.), penicillin and streptomycin (Life Technologies, Grand Island, N.Y.) was added to each well and 50 µL of the cell suspension were transferred to a 96-well cell culture plate containing 150 µL pre-warmed IMDM complete culture medium. The plate was then transferred to a tissue culture incubator and maintained at 37° C. in 5% $CO_2$ for 48 hours.

D. Target Double-Stranded DNA Generation for Deep Sequencing gDNA was isolated from K562 cells 48 hours after RNP transfection using 50 µL QuickExtract DNA Extraction solution (Epicentre, Madison, Wis.) per well followed by incubation at 37° C. for 10 minutes, 65° C. for 6 minutes and 95° C. for 3 minutes to stop the reaction. The isolated gDNAs were diluted with 50 µL water and samples stored at −80° C.

Using the isolated gDNA, a first PCR was performed using Q5 Hot Start High-Fidelity 2× Master Mix (New England Biolabs, Ipswich, Mass.) at 1× concentration, primers at 0.5 µM each (SEQ ID NOs: 93, 94), 3.75 µL of gDNA in a final volume of 10 uL and amplified 98° C. for 1 minute, 35 cycles of 10 s at 98° C., 20 s at 60° C., 30 s at 72° C., and a final extension at 72° C. for 2 min. PCR reaction were diluted 1:100 in water.

A "barcoding" PCR was set up using unique primers for each sample to facilitate multiplex sequencing. The samples and corresponding primer pairs are shown in Table 11.

TABLE 11

Barcoding Primers

| ID | Sample | SEQ ID NO: |
|---|---|---|
| BARCODING PRIMER set-1 | sgD(R)NA-01 60 pmol rep1 | SEQ ID NO: 95, 101 |
| BARCODING PRIMER set-2 | sgD(R)NA-02 60 pmol rep1 | SEQ ID NO: 95, 102 |
| BARCODING PRIMER set-3 | sgD(R)NA-03 60 pmol rep1 | SEQ ID NO: 95, 103 |
| BARCODING PRIMER set-4 | sgD(R)NA-04 60 pmol rep1 | SEQ ID NO: 95, 104 |

TABLE 11-continued

Barcoding Primers

| ID | Sample | SEQ ID NO: |
|---|---|---|
| BARCODING PRIMER set-5 | sgD(R)NA-05 60 pmol rep1 | SEQ ID NO: 95, 105 |
| BARCODING PRIMER set-6 | sgD(R)NA-06 60 pmol rep2 | SEQ ID NO: 95, 106 |
| BARCODING PRIMER set-7 | sgD(R)NA-01 60 pmol rep2 | SEQ ID NO: 96, 101 |
| BARCODING PRIMER set-8 | sgD(R)NA-02 60 pmol rep2 | SEQ ID NO: 96, 102 |
| BARCODING PRIMER set-9 | sgD(R)NA-03 60 pmol rep2 | SEQ ID NO: 96, 103 |
| BARCODING PRIMER set-10 | sgD(R)NA-04 60 pmol rep2 | SEQ ID NO: 96, 104 |
| BARCODING PRIMER set-11 | sgD(R)NA-05 60 pmol rep2 | SEQ ID NO: 96, 105 |
| BARCODING PRIMER set-12 | sgD(R)NA-06 60 pmol rep2 | SEQ ID NO: 96, 106 |
| BARCODING PRIMER set-13 | sgD(R)NA-01 60 pmol rep3 | SEQ ID NO: 97, 101 |
| BARCODING PRIMER set-14 | sgD(R)NA-02 60 pmol rep3 | SEQ ID NO: 97, 102 |
| BARCODING PRIMER set-15 | sgD(R)NA-03 60 pmol rep3 | SEQ ID NO: 97, 103 |
| BARCODING PRIMER set-16 | sgD(R)NA-04 60 pmol rep3 | SEQ ID NO: 97, 104 |
| BARCODING PRIMER set-17 | sgD(R)NA-05 60 pmol rep3 | SEQ ID NO: 97, 105 |
| BARCODING PRIMER set-18 | sgD(R)NA-06 60 pmol rep3 | SEQ ID NO: 97, 106 |
| BARCODING PRIMER set-19 | sgD(R)NA-01 600 pmol rep1 | SEQ ID NO: 98, 101 |
| BARCODING PRIMER set-20 | sgD(R)NA-02 600 pmol rep1 | SEQ ID NO: 98, 102 |
| BARCODING PRIMER set-21 | sgD(R)NA-03 600 pmol rep1 | SEQ ID NO: 98, 103 |
| BARCODING PRIMER set-22 | sgD(R)NA-04 600 pmol rep1 | SEQ ID NO: 98, 104 |
| BARCODING PRIMER set-23 | sgD(R)NA-05 600 pmol rep1 | SEQ ID NO: 98, 105 |
| BARCODING PRIMER set-24 | sgD(R)NA-06 600 pmol rep2 | SEQ ID NO: 98, 106 |
| BARCODING PRIMER set-25 | sgD(R)NA-01 600 pmol rep2 | SEQ ID NO: 99, 101 |
| BARCODING PRIMER set-26 | sgD(R)NA-02 600 pmol rep2 | SEQ ID NO: 99, 102 |
| BARCODING PRIMER set-27 | sgD(R)NA-03 600 pmol rep2 | SEQ ID NO: 99, 103 |
| BARCODING PRIMER set-28 | sgD(R)NA-04 600 pmol rep2 | SEQ ID NO: 99, 104 |
| BARCODING PRIMER set-29 | sgD(R)NA-05 600 pmol rep2 | SEQ ID NO: 99, 105 |
| BARCODING PRIMER set-30 | sgD(R)NA-06 600 pmol rep2 | SEQ ID NO: 99, 106 |
| BARCODING PRIMER set-31 | sgD(R)NA-01 600 pmol rep3 | SEQ ID NO: 100, 101 |
| BARCODING PRIMER set-32 | sgD(R)NA-02 600 pmol rep3 | SEQ ID NO: 100, 102 |
| BARCODING PRIMER set-33 | sgD(R)NA-03 600 pmol rep3 | SEQ ID NO: 100, 103 |
| BARCODING PRIMER set-34 | sgD(R)NA-04 600 pmol rep3 | SEQ ID NO: 100, 104 |
| BARCODING PRIMER set-35 | sgD(R)NA-05 600 pmol rep3 | SEQ ID NO: 100, 105 |
| BARCODING PRIMER set-36 | sgD(R)NA-06 600 pmol rep3 | SEQ ID NO: 100, 106 |

The barcoding PCR was performed using Q5 Hot Start High-Fidelity 2× Master Mix (New England Biolabs, Ipswich, Mass.) at 1× concentration, primers at 0.5 µM each, 1 µL of 1:100 diluted first PCR, in a final volume of 10 µL and amplified 98° C. for 1 minutes, 12 cycles of 10 s at 98° C., 20 s at 60° C., 30 s at 72° C., and a final extension at 72° C. for 2 min.

E. SPRIselect Clean-Up

PCR reactions were pooled into a single microfuge tube for SPRIselect (Beckman Coulter, Pasadena, Calif.) bead-based clean-up of amplicons for sequencing.

To the pooled amplicons, 0.9× volumes of SPRIselect beads were added, and mixed and incubated at room temperature (RT) for 10 minutes. The microfuge tube was placed on a magnetic tube stand (Beckman Coulter, Pasadena, Calif.) until solution had cleared. Supernatant was removed and discarded, and the residual beads were washed with 1 volume of 85% ethanol, and incubated at RT for 30 seconds. After incubation, ethanol was aspirated and beads are air dried at RT for 10 min. The microfuge tube was then removed from the magnetic stand and 0.25× volumes of Qiagen EB buffer (Qiagen, Venlo, Limburg) was added to the beads, mixed vigorously, and incubated for 2 minutes at room temperature. The microfuge tube was returned to the magnet, incubated until solution had cleared, and supernatant containing the purified amplicons was dispensed into a clean microfuge tube. The purified amplicon library was quantified using the Nanodrop™ 2000 system (Thermo Scientific, Wilmington, Del.) and library-quality analyzed using the Fragment Analyzer™ system (Advanced Analytical Technologies, Inc., Ames, Iowa) and the DNF-910 double-stranded DNA Reagent Kit (Advanced Analytical Technologies, Inc. Ames, Iowa).

F. Deep Sequencing Set-Up

The amplicon library was normalized to a 4 nmolar concentration as calculated from Nanodrop values and size of the amplicons. The library were analyzed on MiSeq Sequencer (Illumina, San Diego, Calif.) with MiSeq Reagent Kit v2 (Illumina, San Diego, Calif.) for 300 cycles with two 151-cycle paired-end run plus two eight-cycle index reads.

G. Deep Sequencing Data Analysis

The identity of products in the sequencing data were determined based on the index barcode sequences adapted onto the amplicons in the barcoding round of PCR. A computational script was used to process the MiSeq data by executing the following tasks:

Reads were aligned to the human genome (build GRCh38/38) using Bowtie (http://bowtie-bio.sourceforge.net/index.shtml) software.

Aligned reads were compared to the expected wild-type AAVS-1 locus sequence, reads not aligning to any part of the AAVS-1 locus were discarded.

Reads matching wild-type AAVS-1 sequence were tallied.

Reads with indels (insertion or the deletion of bases) were categorized by indel type and tallied.

Total indel reads were divided by the sum of wild-type reads and indel reads give the percent indels detected.

FIG. 7 shows the results of an analysis of the AAVS-1 target locus from human K562 cells nucleofected with sgD(R)NA/Cas9 targeting a region in the AAVS-1 locus. The x-axis shows the SEQ ID NO. For the sgD(R)NA used, the y-axis shows the percent indel detected from MiSeq data. Series A shows the average percent indels detected for three independent replicates for a given sgD(R)NA at 20 pmols Cas9:120 pmols sgD(R)NA, and Series B shows the average percent indels detected for three independent replicates for a given sgD(R)NA at 100 pmols Cas9:600 pmols sgD(R)NA. Standard deviation of the average percent of the three replicates is represented by vertical black lines. The numbers below the bars correspond to the SEQ ID NO. of the sgD(R)NA used in the transfection, sequences of the sgD(R)NA are provided in Table 10. This data shows the ability of various types of sgD(R)NA to induce modifications at a target region in human cells in a sequence specific and dose dependent manner.

The methods described herein were practiced by one of ordinary skill in the art to demonstrate in vivo activity of a sgD(R)NA/Cas9 through analysis of deep sequencing.

EXAMPLE 8

Screening of Multiple crD(R)NAs Comprising DNA Target-Binding Sequences

This example illustrates the use of crD(R)NAs of the present disclosure to modify targets present in human genomic DNA and measure the level of cleavage activity at those sites. Target sites can first be selected from genomic DNA and then crD(R)NAs can then be designed to target those selected sequences. Measurements can then be carried out to determine the level of target cleavage that has taken place. Not all of the following steps are required for every screening nor must the order of the steps be as presented, and the screening can be coupled to other experiments, or form part of a larger experiment.

A. Select a DNA Target Region from Genomic DNA

Identify all PAM sequences (e.g., 'NGG') within the selected genomic region.

Identify and select one or more 20 nucleotide sequence long sequences (target DNA sequence) that are 5' adjacent to PAM sequences.

Selection criteria can include but are not limited to: homology to other regions in the genome; percent G-C content; melting temperature; presences of homopolymer within the spacer; and other criteria known to one skilled in the art.

Append an appropriate crD(R)NA sequence to the 3' end of the identified target DNA sequence. A crD(R)NA construct is typically synthesized by a commercial manufacturer and the cognate tracrRNA is produced as described in Example 1 by in vitro transcription.

A crD(R)NA as described herein can be used with cognate tracrRNA to complete a crD(R)NA/tracrRNA system for use with a cognate Cas protein.

B. Determination of Cleavage Percentages and Specificity

In vitro cleavage percentages and specificity associated with a crD(R)NA/tracrRNA system are compared, for example, using the Cas cleavage assays of Example 3, as follows:

(a) If only a single target DNA sequence is identified or selected, the cleavage percentage and specificity for the DNA target region can be determined. If so desired, cleavage percentage and/or specificity can be altered in further experiments using methods of the present disclosure including but not limited to modifying the crD(R)NA, introducing effector proteins/effector protein-binding sequences or ligand/ligand binding moieties.

(b) The percentage cleavage data and site-specificity data obtained from the cleavage assays can be compared between different DNAs comprising the target binding sequence to identify the target DNA sequences having the best cleavage percentage and highest specificity. Cleavage percentage data and specificity data provide criteria on which to base choices for a variety of applications. For example, in some situations the activity of the crD(R)NA may be the most important factor. In other situations, the specificity of the cleavage site may be relatively more important than the cleavage percentage. If so desired, cleavage percentage and/or specificity are altered in further experiments using methods of the present disclosure including but not limited to modifying the crD(R)NA, introducing effector proteins/effector protein-binding sequences or ligand/ligand binding moieties.

Optionally, or instead of, the in vitro analysis, in vivo cleavage percentages and specificity associated with a crD(R)NA system are compared, for example, using the T7E1 assay described in Example 5, as follows:

(a) If only a target DNA sequence is identified the cleavage percentage and specificity for the DNA target region can be determined. If so desired, cleavage percentage and/or specificity are altered in further experiments using methods of the present disclosure including but not limited to modifying the crD(R)NA, introducing effector proteins/effector protein-binding sequences or ligand/ligand binding moieties.

(b) The percentage cleavage data and site-specificity data obtained from the cleavage assays can be compared between different target DNAs to identify a crD(R)NA sequence that results in the highest percentage cleavage of target DNA and the highest specificity for the target DNA. Cleavage percentage data and specificity data provide criteria on which to base choices for a variety of applications. For example, certain embodiments may rely on the activity of a crD(R)NA and may be the most important factor. In certain embodiments, the specificity of the cleavage site may be relatively more important than the cleavage percentage. In certain embodiments, cleavage percentage and/or specificity can be altered using methods of the present disclosure including but not limited to modifying the RNA, introducing effector proteins/effector protein-binding sequences or ligand/ligand binding moieties.

Following the guidance of the present specification and examples, the screening described in this example can be practiced by one of ordinary skill in the art with other Class II CRISPR Cas proteins, including, but not limited to Cas9, Cas9-like, Cas, Cas3, Csn2, Cas4, proteins encoded by Cas9 orthologs, Cas9-like synthetic proteins, Cas9 fusions, Cpf1, Cpf1-like, C2c1, C2c2, C2c3, and variants and modifications thereof, combined with their cognate polynucleotide components modified as described herein to comprise a crD(R)NA.

EXAMPLE 9 crD(R)NA:tracrRNA and sgD(R)NA Mediated Nicking

This example illustrates the method through which a crD(R)NA:tracrRNA complex or sgD(R)NA of the present disclosure might be used to induced nicks in a double stranded DNA (dsDNA) plasmid target in conjunction with *S. pyogenes* Cas9 containing a D10A mutation (Cas9-D10A) rendering the RuvC nuclease lobe inactive. Not all of the following steps are required, nor must the order of the steps be as presented.

The *S. pyogenes* Cas9 has two active nuclease domains, the RuvC and the HNH domains. A mutation of the aspartic acid at the 10th amino acid position of the *S. pyogenes* Cas9, converting it to an alanine, reduces the nuclease capability of the RuvC domain. The HNH domain remains active but the Cas9-D10A site-directed polypeptide can only cause nicks in the phosphodiester backbone of the DNA target strand complementary to the spacer sequence.

Examples of suitable vectors, media, culture conditions, etc. are described. Modifications of these components and conditions will be understood by one of ordinary skill in the art in view of the teachings of the present specification.

Guide reagents were generated according to Example 1 of the present specification.

The dsDNA target was generated as described in Example 2 using SEQ ID NOs 133 and 134. The amplified fragment was then cloned into suitable LIC compatible vector. One such suitable vector is the commercially available pET His6 LIC cloning vector (Addgene, Cambridge, Mass.). The plasmid was transformed into bacterial strain for plasmid expression, using commercially available XL1-Blu bacterial cells (Agilent, Santa Clara, Calif.).

Bacterial cells containing the LIC vectors were grown in LB media supplemented with 100 ug/mL ampicillin (Sigma-Aldrich, St. Louis, Mo.) for 18 hours at 37° C. Cells were centrifuged at 5,000 rpm for 15 minutes, after which the plasmid was extracted using Qiagen Plasmid Kit (Qiagen, Venlo, Netherlands).

Biochemical cleavage of purified plasmid was performed as detailed in Example 3 of the present specification, with the modification that DNA target was replaced with the purified plasmid at a final concentration of 1 nM in the reaction. crD(R)NA were hybridized with tracrRNA (SEQ ID NO: 2) in the manner described in Example 3.

Biochemical reactions were analyzed by running on a 1% agarose gel stained with SYBR gold (Life Technologies, Grand Island, N.Y.). Nicking efficiency was calculated based upon the disappearances of supercoiled plasmid form and the appearance of the nicked-open circular form of the plasmid (nicked plasmid), which was distinguishable by the shift in the migration rate of the plasmid on the gel.

Percentages of the nicked plasmid were calculated from the intensities of stained bands on the gel containing the nicked plasmid and the supercoiled plasmid. Intensities were measured using area under the curve values as calculated by FIJI (ImageJ; an open source Java image processing program). Percentages of nicking were calculated by dividing the staining intensity of the nicked plasmid by the sum of both the staining intensities of the nicked plasmid species and the supercoiled plasmid species.

SEQ ID NOs for the crD(R)NA and sgD(R)NA used in this experiment are shown in Table 12.

TABLE 12

Nicking crD(R)NA and sgD(R)NA

| Sample ID | Description | SEQ ID NO: |
|---|---|---|
| A | crD(R)NA | SEQ ID NO: 38 |
| B | crD(R)NA w/18 nt spacer | SEQ ID NO: 135 |

TABLE 12-continued

Nicking crD(R)NA and sgD(R)NA

| Sample ID | Description | SEQ ID NO: |
|---|---|---|
| C | crD(R)NA | SEQ ID NO: 41 |
| D | crD(R)NA w/17 nt spacer | SEQ ID NO: 136 |
| E | crD(R)NA | SEQ ID NO: 43 |
| F | crD(R)NA w/18 nt spacer | SEQ ID NO: 137 |
| H | sgD(R)NA | SEQ ID NO: 127 |
| I | sgRNA control | SEQ ID NO: 1 |
| H | target plasmid only | — |

Figure 8:
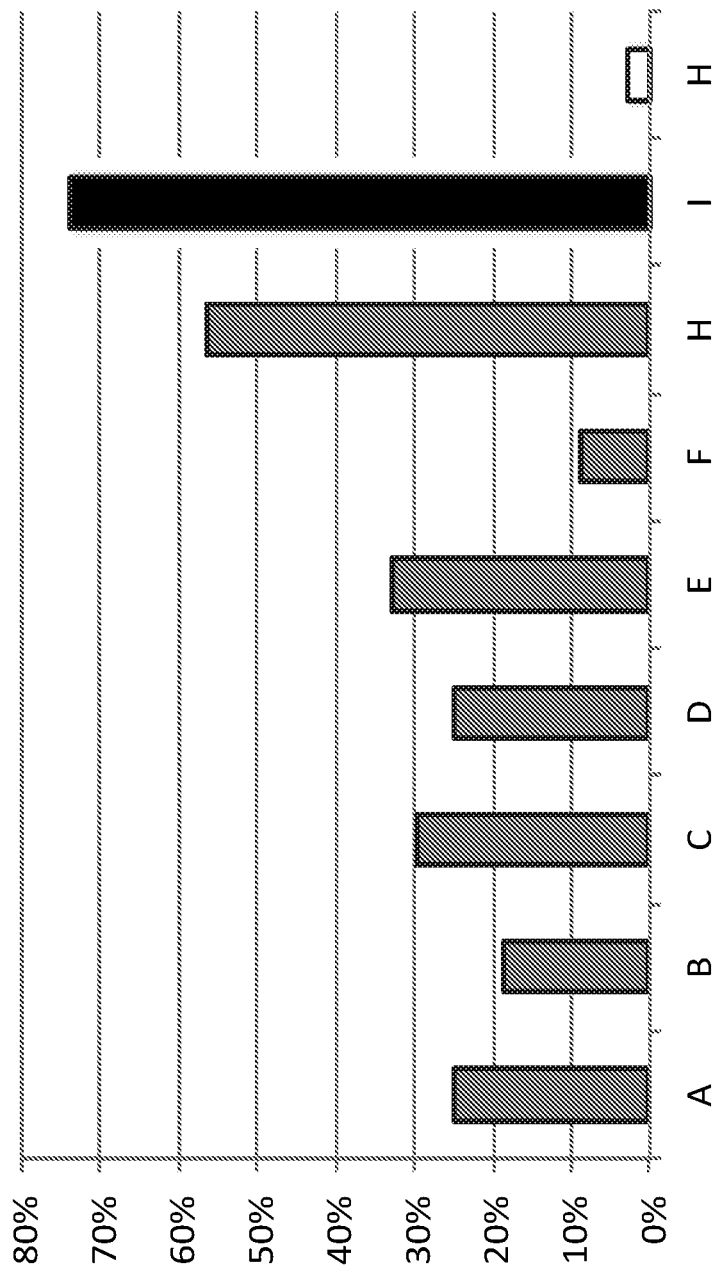
FIG. 8 shows the results of nicking activity of a crD(R) NA or sgD(R)NA with a Cas9-D10A protein against a plasmid target in vitro.

FIG. 8 shows the results of the biochemical nicking activity of a crD(R)NA or sgD(R)NA with a Cas9-D10A protein against a plasmid target. Nicking percentages are shown on the y-axis. crD(R)NA and sgD(R)NA samples are shown on the x-axis and correspond to the sample IDs shown in Table 12. The data show the ability of crD(R)NA and sgD(R)NA to support nicking activity of the Cas9-D10A protein against a target plasmid. The data also show that truncation of the spacer sequence from the 5' end of the spacer (SEQ ID NOs: 135, 136, and 137) is capable of nicking activity.

Following the guidance of the present specification and the examples herein, the design and validation of the nicking activity of crD(R)NA:tracrRNA and sgD(R)NA can be practiced by one of ordinary skill in the art.

EXAMPLE 10

Identification and Screening of CRISPR RNA and Trans-Activating CRISPR RNA

This example illustrates the method through which CRISPR RNAs (crRNAs) and trans-activating CRISPR RNAs (tracrRNAs) of a CRISPR-Cas Type II system may be identified. The method presented here is adapted from Chylinski, et. al., (RNA Biol; 10 (5):726-37 (2013)). Not all of the following steps are required for screening nor must the order of the steps be as presented.

A. Identify a Bacterial Species Containing a CRISPR-Cas9 Type-II System

Using the Basic Local Alignment Search Tool (BLAST, blast.ncbi.nlm.nih.gov/Blast.cgi), a search of various species' genomes is conducted to identify Cas9 or Cas9-like proteins. Type II CRISPR-Cas9 systems exhibit a high diversity in sequence across bacterial species, however Cas9 orthologs exhibit conserved domain architecture of central HNH endonuclease domain and a split RuvC/RNase H domain. Primary BLAST results are filtered for identified domains; incomplete or truncated sequences are discarded and Cas9 orthologs identified.

When a Cas9 ortholog is identified in a species, sequences adjacent to the Cas9 ortholog's coding sequence are probed for other Cas proteins and an associated repeat-spacer array in order to identify all sequences belonging to the CRISPR-Cas locus. This may be done by alignment to other CRISPR-Cas Type-II loci already known in the public domain, with the knowledge that closely related species exhibit similar CRISPR-Cas9 locus architecture (i.e., Cas protein composition, size, orientation, location of array, location of tracrRNA, etc.).

B. Identification of Putative crRNA and tracrRNA

Within the locus, the crRNAs are readily identifiable by the nature of their repeat sequences interspaced by fragments of foreign DNA and make up the repeat-spacer array. If the repeat sequence is from a known species, it is identified in and retrieved from the CRISPRdb database (crispr.u-psud.fr/crispr/). If the repeat sequence is not known to be associated with a species, repeat sequences are predicted using CRISPRfinder software (crispr.u-psud.fr/Server/) using the sequence identified as a CRISPR-Cas Type-II locus for the species as described above.

Once the sequence of the repeat sequence is identified for the species, the tracrRNA is identified by its sequence complementarity to the repeat sequence in the repeat-spacer array (tracr anti-repeat sequence). In silico predictive screening is used to extract the anti-repeat sequence to identify the associated tracrRNA. Putative anti-repeats are screened, for example, as follows.

The identified repeat sequence for a given species is used to probe the CRISPR-Cas9 locus for the anti-repeat sequence (e.g., using the BLASTp algorithm or the like). The search is typically restricted to intronic regions of the CRISPR-Cas9 locus.

An identified anti-repeat region is validated for complementarity to the identified repeat sequence.

A putative anti-repeat region is probed both 5' and 3' of the putative anti-repeat for a Rho-independent transcriptional terminator (TransTerm HP, transterm.cbcb.umd.edu/).

Thus, the identified sequence comprising the anti-repeat element and the Rho-independent transcriptional terminator is determined to be the putative tracrRNA of the given species.

C. Preparation of RNA-Seq Library

The putative crRNA and tracrRNA that were identified in silico are further validated using RNA sequencing (RNAseq).

Cells from species from which the putative crRNA and tracrRNA were identified are procured from a commercial repository (e.g., ATCC, Manassas, Va.; DSMZ, Braunschweig, Germany).

Cells are grown to mid-log phase and total RNA prepped using Trizol reagent (Sigma-Aldrich, St. Louis, Mo.) and treated with DNaseI (Fermentas, Vilnius, Lithuania).

10 ug of the total RNA is treated with Ribo-Zero rRNA Removal Kit (Illumina, San Diego, Calif.) and the remaining RNA purified using RNA Clean and Concentrators (Zymo Research, Irvine, Calif.).

A library is then prepared using TruSeq Small RNA Library Preparation Kit (Illumina, San Diego, Calif.) following the manufacturer's instructions, which results in the presence of adapter sequences associated with the cDNA.

The resulting cDNA library is sequenced using MiSeq Sequencer (Illumina, San Diego, Calif.).

D. Processing of Sequencing Data

Sequencing reads of the cDNA library can be processed using the following method.

Adapter sequences are removed using cutadapt 1.1 (pypi.python.org/pypi/cutadapt/1.1) and 15 nt are trimmed from the 3'end of the read to improve read quality.

Reads are aligned back to each respective species' genome (from which the putative tracrRNA was identified) with a mismatch allowance of 2 nucleotides.

Read coverage is calculated using BedTools (bedtools.readthedocs.org/en/latest/).

Integrative Genomics Viewer (IGV, www.broadinstitute.org/igv/) is used to map the starting (5') and ending (3') position of reads. Total reads retrieved for the putative tracrRNA are calculated from the SAM file of alignments.

The RNA-seq data is used to validate that a putative crRNA and tracrRNA element is actively transcribed in vivo. Confirmed hits from the composite of the in silico and RNA-seq screens are validated for functional ability of the identified crRNA and tracrRNA sequences to support Cas9 mediated cleavage of a double-stranded DNA target using methods outline herein (see Examples 1, 2, and 3).

Following the guidance of the present specification and the examples herein, the identification of novel crRNA and tracrRNA sequences can be practiced by one of ordinary skill in the art.

EXAMPLE 11

Design of crD(R)NA and sgD(R)NA

This example illustrates the method through which crD(R)NA and sgD(R)NA are designed from crRNA and tracrRNA, respectively. Not all of the following steps are required for screening nor must the order of the steps be as presented.

Identification of the crRNA and tracrRNA guide sequences for a given species are performed as described in Example 10.

Identified crRNA and tracrRNA sequences are reverse-transcribed in silico to DNA. Upper stem, lower stem and bulge elements are identified from the sequences of the crRNA and tracrRNA. RNA bases are introduced into the DNA sequence of the crDNA and tracrDNA sequences creating crD(R)NA and sgD(R)NA, respectively. The placement, number and distribution of RNA bases within the crDNA and tracrRNA can be chosen using either computational or experimental screening methods. A collection of crD(R)NAs are designed with ribonucleotides placed in a number of different locations within the molecule. Preferably, deoxyriboucleotides within the lower stem are substituted for ribonucleotides in some crD(R)NA sequences. Ribonucleotides are substituted at the 3' end of the spacer sequence in some crD(R)NA sequences. Additional crD(R)NA and sgD(R)NA sequences are designed, for example, as follows.

Repositories of 3-dimensional protein structures (e.g., RCSB PDB; rcsb.org) in the public domain are searched to identify Cas endonuclease structures. The repository is searched for high resolution coordinate files of Cas endonucleases bound to their cognate crRNA and tracrRNA. Structural neighbors, defined by sequence or tertiary structural similarities to the Cas endonuclease of interest are used if there is no solved structure for the Cas endonuclease of interest. Deposited coordinate files are downloaded. Using visualization software, such as PyMOL (PyMOL Molecular Graphics System, Version 1.7.4 Schrödinger, LLC), the coordinates are analyzed to identify ribose-specific interactions between the Cas endonuclease protein and the nucleotides of the crRNA and tracrRNA. Positions where the protein makes direct or indirect contact (i.e., through a water or metal intermediate) with the nucleotides of the crRNA and tracrRNA are used to identify favored positions within the guide sequences for replacing deoxyribonucleotides with ribonucleotides or other nucleotide variants.

crRNA and tracrRNA sequences are conserved when compared with Cas9 proteins from related species. Alignment of a guide sequence with the other known guide sequences from similar species provides additional information on conserved bases that would confer a preference for ribonucleotides. Multiple sequence alignments of crRNA or tracrRNA are performed using the web-based software MUSCLE (ebi.ac.uk/Tools/mas/muscle/). Alignments are then assessed for conserved nucleotide sequence positions along the backbone.

Nucleic acid secondary structure prediction software (e.g RNAfold; rna.tbi.univie.ac.at/cgi-bin/RNAfold.cgi) is used to analyze the folding of the guide backbone. Regions where RNA specific torsion angles would be favored are used to inform placement of ribonucleotide locations in both the crDNA and/or tracrDNA.

Combinations of secondary structure, protein-nucleic acid interaction, and sequence conservation are used to inform the positioning of ribonucleotides within crD(R)NA, tracrD(R)NA and sgD(R)NA sequence. Multiple designs of crD(R)NA and tracrD(R)NA are tested with the understanding that different configurations may support different desired properties (i.e., activity, specificity, stability, etc.). The crD(R)NA and tracrD(R)NA can be joined into a single molecule by a linker to form a sgD(R)NA. The combining of the crD(R)NA and tracrD(R)NA may be accompanied by a reduction in the total number of nucleotides at the 3' end of the crD(R)NA and 5' end of the tracrD(R)NA that together would form the upper stem. SEQ ID NOs 138-142, 147-150, 154-157, and 161-164 show designs for crD(R)NAs and tracrD(R)NAs. SEQ ID NOs 143-146, 151-153, 158-160, and 165-167 show designs for sgD(R)NAs. Table 13 gives the identity of sequences.

TABLE 13 crD(R)NA, tracrD(R)NA, and sgD(R)NA

| ID | Genus/Species | Guide Description |
|---|---|---|
| SEQ ID NO: 138 | *Staphylococcus aureus* | crD(R)NA |
| SEQ ID NO: 139 | *Staphylococcus aureus* | crD(R)NA |
| SEQ ID NO: 140 | *Staphylococcus aureus* | crD(R)NA |
| SEQ ID NO: 141 | *Staphylococcus aureus* | crD(R)NA |
| SEQ ID NO: 142 | *Staphylococcus aureus* | tracrRNA |
| SEQ ID NO: 143 | *Staphylococcus aureus* | sgD(R)NA |
| SEQ ID NO: 144 | *Staphylococcus aureus* | sgD(R)NA |
| SEQ ID NO: 145 | *Staphylococcus aureus* | sgD(R)NA |
| SEQ ID NO: 146 | *Staphylococcus aureus* | sgD(R)NA |
| SEQ ID NO: 147 | *Streptococcus thermophilus* CRISPR-I | crD(R)NA |
| SEQ ID NO: 148 | *Streptococcus thermophilus* CRISPR-I | crD(R)NA |
| SEQ ID NO: 149 | *Streptococcus thermophilus* CRISPR-I | crD(R)NA |
| SEQ ID NO: 150 | *Streptococcus thermophilus* CRISPR-I | tracrRNA |
| SEQ ID NO: 151 | *Streptococcus thermophilus* CRISPR-I | sgD(R)NA |
| SEQ ID NO: 152 | *Streptococcus thermophilus* CRISPR-I | sgD(R)NA |
| SEQ ID NO: 153 | *Streptococcus thermophilus* CRISPR-I | sgD(R)NA |
| SEQ ID NO: 154 | *Neisseria meningitidis* | crD(R)NA |
| SEQ ID NO: 155 | *Neisseria meningitidis* | crD(R)NA |
| SEQ ID NO: 156 | *Neisseria meningitidis* | crD(R)NA |
| SEQ ID NO: 157 | *Neisseria meningitidis* | tracrRNA |
| SEQ ID NO: 158 | *Neisseria meningitidis* | sgD(R)NA |
| SEQ ID NO: 159 | *Neisseria meningitidis* | sgD(R)NA |
| SEQ ID NO: 160 | *Neisseria meningitidis* | sgD(R)NA |
| SEQ ID NO: 161 | *Streptococcus pasteurianus* | crD(R)NA |
| SEQ ID NO: 162 | *Streptococcus pasteurianus* | crD(R)NA |
| SEQ ID NO: 163 | *Streptococcus pasteurianus* | crD(R)NA |
| SEQ ID NO: 164 | *Streptococcus pasteurianus* | tracrRNA |
| SEQ ID NO: 165 | *Streptococcus pasteurianus* | sgD(R)NA |
| SEQ ID NO: 166 | *Streptococcus pasteurianus* | sgD(R)NA |
| SEQ ID NO: 167 | *Streptococcus pasteurianus* | sgD(R)NA |

Sequences are provided to a commercial manufacturer (e.g., Integrated DNA Technologies, Coralville, Iowa) for synthesis.

crD(R)NA, tracrD(R)NA, and sgD(R)NA are tested experimentally to determine the activity of different sequences to support Cas9 mediated cleavage of a double-stranded DNA target using methods set forth herein (see Examples 1, 2, and 3).

Following the guidance of the present specification and the examples herein, the design and validation of novel crD(R)NA, tracrD(R)NA, and sgD(R)NA sequences can be practiced by one of ordinary skill in the art.

EXAMPLE 12

Design of Type V Cpf1 crD(R)NA and sgD(R)NA Elements and Use with Cpf1 to Modify DNA Tables 14 and 15 below provide exemplary dual guide crD(R)NAs and sgD(R)NAs for use with Type V CRISPR systems. The reference to exemplary figures and SEQ ID NOs is not intended to be limiting in anyway and it is understood by one of skill in the art that, based on the disclosure in Tables 14, 15, and the associated SEQ ID Nos and exemplary figures, dual guide crD(R)NAs and sgD(R)NAs for use with Type V CRISPR systems can be designed to target any desired sequence within a target nucleic acid.

TABLE 14

Description of Type V crD(R)NA 5' and 3' Elements and Combinations Used to Form Dual Guide crD(R)NAs and to Direct Cpf1 Activity to DNA Sequence of Interest

| Description of Sequence | Exemplary FIG. | SEQ ID NO: |
|---|---|---|
| Type V Cpf1 crRNA 5' element | 12B, 13D, 13E, 13H | SEQ ID NO: 168 |
| Type V Cpf1 crD(R)NA 5' element | 12C, 13B, 13C, 13F, 13G | SEQ ID NO: 169 |
| Phosphorothioate-protected Type V Cpf1 crRNA 5' element | 12B, 13D, 13E, 13H | SEQ ID NO: 170 |
| Phosphorothioate-protected Type V Cpf1 crD(R)NA 5' element | 12C, 13B, 13C, 13F, 13G | SEQ ID NO: 171 |
| Type V Cpf1 crRNA 3' element with 25 nucleotide RNA targeting region | 12D | SEQ ID NO: 172 |
| Type V Cpf1 crRNA 3' element with 20 nucleotide RNA targeting region | 12D | SEQ ID NO: 173 |
| Phosphorothioate-protected Type V Cpf1 crRNA 3' element with 25 nucleotide RNA targeting region | 12D | SEQ ID NO: 174 |
| Phosphorothioate-protected Type V Cpf1 crRNA 3' element with 20 nucleotide RNA targeting region | 12D | SEQ ID NO: 175 |
| Type V Cpf1 crD(R)NA 3' element with 25 nucleotide DNA targeting region | 12F, 13E, 13F | SEQ ID NO: 176 |
| Type V Cpf1 crD(R)NA 3' element with 25 nucleotide DNA/RNA targeting region | 12H, 12I | SEQ ID NO: 177 |
| Type V Cpf1 crD(R)NA 3' element with 25 nucleotide DNA/RNA targeting region | 12H, 12I | SEQ ID NO: 178 |
| Type V Cpf1 crD(R)NA 3' element with 25 nucleotide DNA/RNA targeting region | 12H, 12I | SEQ ID NO: 179 |
| Type V Cpf1 crD(R)NA 3' element with 25 nucleotide RNA targeting region | 12E, 13C, 13D | SEQ ID NO: 180 |
| Phosphorothioate-protected Type V Cpf1 crD(R)NA 3' element with 25 nucleotide RNA targeting region | 12E, 13C, 13D | SEQ ID NO: 181 |
| Type V Cpf1 crD(R)NA 3' element with 20 nucleotide RNA targeting region | 12E, 13C, 13D | SEQ ID NO: 182 |
| Phosphorothioate-protected Type V Cpf1 crD(R)NA 3' element with 20 nucleotide RNA targeting region | 12E, 13C, 13D | SEQ ID NO: 183 |
| Type V Cpf1 crD(R)NA 3' element with 25 nucleotide DNA targeting region | 12G, 13G, 13H | SEQ ID NO: 184 |
| Type V Cpf1 crD(R)NA 3' element with 25 nucleotide DNA/RNA targeting region | 12H, 12I | SEQ ID NO: 185 |
| Type V Cpf1 crD(R)NA 3' element with 25 nucleotide DNA/RNA targeting region | 12H, 12I | SEQ ID NO: 186 |

TABLE 14-continued

Description of Type V crD(R)NA 5' and 3' Elements and Combinations Used to Form Dual Guide crD(R)NAs and to Direct Cpf1 Activity to DNA Sequence of Interest

| Description of Sequence | Exemplary FIG. | SEQ ID NO: |
|---|---|---|
| Type V Cpf1 crD(R)NA 3' element with 25 nucleotide DNA/RNA targeting region | 12H, 12I | SEQ ID NO: 187 |
| Dual guide Type V Cpf1 crRNA containing 3' and 5' elements | 13A | SEQ ID NO: 168; SEQ ID NO: 172 |
| Dual guide Type V Cpf1 crRNA containing phosphorothioate protected 3' and 5' elements | 13A | SEQ ID NO: 170; SEQ ID NO: 173 |
| Dual guide Type V Cpf1 cr(D)RNA containing 3' and 5' elements | 13B | SEQ ID NO: 169; SEQ ID NO: 172 |
| Dual guide Type V Cpf1 cr(D)RNA containing 3' and 5' elements | 13C | SEQ ID NO: 169; SEQ ID NO: 180 |
| Dual guide Type V Cpf1 cr(D)RNA containing 3' and 5' elements | 13D | SEQ ID NO: 168; SEQ ID NO: 180 |
| Dual guide Type V Cpf1 cr(D)RNA containing 3' and 5' elements | 13E | SEQ ID NO: 168; SEQ ID NO: 176 |
| Dual guide Type V Cpf1 cr(D)RNA containing 3' and 5' elements | 13F | SEQ ID NO: 169; SEQ ID NO: 176 |
| Dual guide Type V Cpf1 cr(D)RNA containing 3' and 5' elements | 13G | SEQ ID NO: 169; SEQ ID NO: 184 |
| Dual guide Type V Cpf1 cr(D)RNA containing 3' and 5' elements | 13H | SEQ ID NO: 168; SEQ ID NO: 184 |

TABLE 15

Description of Type V sgD(R)NA Designs

| Description of Sequence | Exemplary FIG. | SEQ ID NO: |
|---|---|---|
| Type V Cpf1 sgD(R)NA with 25 nucleotide RNA targeting region | 10A | SEQ ID NO: 188 |
| Type V Cpf1 sgD(R)NA with 25 nucleotide RNA targeting region | 10B | SEQ ID NO: 189 |
| Type V Cpf1 sgD(R)NA with 25 nucleotide RNA targeting region | 10C | SEQ ID NO: 190 |
| Type V Cpf1 sgD(R)NA with 25 nucleotide DNA targeting region | 11D | SEQ ID NO: 191 |
| Type V Cpf1 sgD(R)NA with 25 nucleotide DNA targeting region | 11B | SEQ ID NO: 192 |
| Type V Cpf1 sgD(R)NA with 25 nucleotide DNA/RNA targeting region | 11E | SEQ ID NO: 193 |
| Type V Cpf1 sgD(R)NA with 25 nucleotide DNA/RNA targeting region | 11E | SEQ ID NO: 194 |
| Type V Cpf1 sgD(R)NA with 25 nucleotide DNA/RNA targeting region | 11E | SEQ ID NO: 195 |
| Type V Cpf1 sgD(R)NA with 25 nucleotide DNA targeting region | 11A | SEQ ID NO: 196 |
| Type V Cpf1 sgD(R)NA with 25 nucleotide DNA/RNA targeting region | 11E | SEQ ID NO: 197 |
| Type V Cpf1 sgD(R)NA with 25 nucleotide DNA/RNA targeting region | 11E | SEQ ID NO: 198 |
| Type V Cpf1 sgD(R)NA with 25 nucleotide DNA/RNA targeting region | 11E | SEQ ID NO: 199 |
| Type V Cpf1 sgD(R)NA with 25 nucleotide DNA targeting region | 11C | SEQ ID NO: 200 |
| Type V Cpf1 sgD(R)NA with 25 nucleotide DNA/RNA targeting region | 11E | SEQ ID NO: 201 |
| Type V Cpf1 sgD(R)NA with 25 nucleotide DNA/RNA targeting region | 11E | SEQ ID NO: 202 |
| Type V Cpf1 sgD(R)NA with 25 nucleotide DNA/RNA targeting region | 11E | SEQ ID NO: 203 |

A. Design of Type V Cpf1 crD(R)NA and sgD(R)NA Elements

Cpf1 orthologs are identified using sequence analysis programs such as PSI-BLAST, PHI-BLAST and HMMer. Once a Cpf1 ortholog is identified, nearby sequences are searched to identify the associated CRISPR array. crRNA sequences are identified as repeat sequences located within the CRISPR array as described in Zetsche et al. (Cell; 163 (3):759-71 (2015)). Type V crRNA sequences contain a stem loop within the repeat sequence, located 5' to the targeting region sequence. The stem loop comprises a 5' element and a 3' element. The sequences of both the 5' element, the 3' element, and the loop of the crRNA are identified. The sequence of these crRNA elements are reverse-transcribed in silico to DNA. 5' elements are designed containing mixtures of ribonucleotides and deoxyribonucleotides. Examples of 5' elements are shown in FIG. 12, FIG. 13 and Table 14. 3' elements are designed containing mixtures of ribonucleotides and deoxyribonucleotides. Examples of 3' elements are shown in FIG. 12, FIG. 13 and Table 14. Targeting region sequences are selected to be adjacent to PAM sequences in the DNA of interest and are appended to the 3' end of 3' crRNA elements. Targeting region sequences are designed containing DNA, DNA and RNA, or RNA nucleotides. By combining crD(R)NA 3' elements and crD(R)NA 5' elements together (Table 14, FIG. 12, FIG. 13) to form dual guide TypeV crD(R)NAs, Cpf1 is directed to cut target nucleic acid sequences in the target nucleic acid of interest. A collection of crD(R)NAs for testing are designed with ribonucleotides placed in a number of different locations within the crD(R)NA sequences. Preferably, deoxyriboucleotides within the 3'stem and 5'stem are substituted for ribonucleotides in some crD(R)NA sequences. Ribonucleotides are substituted at the 5' end of the targeting region sequence in some crD(R)NA sequences.

Using combinations of targeting region, 3' elements, and 5' elements connected by a loop sequence, different versions of sgD(R)NA are designed. The placement, number, and distribution of RNA bases within the sgD(R)NA can be chosen using either computational or experimental screening methods. A collection of sgD(R)NAs are designed with ribonucleotides placed in a number of different locations within the sgD(R)NAs. Preferably, deoxyriboucleotides within the 3'stem and 5'stem are substituted for ribonucleotides in some sgD(R)NA sequences. Ribonucleotides are substituted at the 5' end of the targeting region sequence in some sgD(R)NA sequences. Examples of designed sgD(R)NAs are listed in Table 15, and shown in FIGS. 10A-C and FIGS. 11A-E.

In the following, sgD(R)NA sequences are used, but it is understood that pairs of 3' and 5' crD(R)NA elements (examples of which are shown in Table 14) can be used in place of the sgD(R)NA.

B. Digestion of Nucleic Acid Sequences with Cpf1 and sgD(R)NA

Cpf1 sgD(R)NA can be used together with Cpf1 to target and cut nucleic acid sequences. Target nucleic acid is either RNA, genomic DNA, plasmid DNA, or amplified DNA. Amplified target DNA can be prepared as described in Example 2. sgD(R)NA sequences are synthesized containing spacer sequences targeting sequences of interest in the target DNA. Cleavage assays are carried out as described in Zetsche et al. (2015) and analyzed using methods described in Example 3. In summary, target nucleic acid is incubated with Cpf1 and the sgD(R)NA sequence or sequences in an appropriate buffer chosen to support Cpf1 activity. Nucleic acid is analyzed to determine whether digestion has taken place as described in Example 3. Two or more Cpf1/sgD(R)NA complexes can be used to cut sections of DNA from a target DNA. The section of DNA has overhanging ends and can be ligated to complementary sequence adaptors or vectors after it has been separated from the parent DNA.

C. Genome Editing with Cpf1 sgD(R)NA Ribonucleoprotein Complexes

An *E. coli* expression vector is constructed by synthesizing a codon-optimized open-reading frame encoding Cpf1 and cloning the open-reading frame into an expression plasmid (e.g., pET27b). The coding sequence can include an affinity tag for purification of the protein, and a NLS sequence at the C-terminus to drive nuclear localization in eukaryotic cells. Cpf1 protein can be expressed in *E. coli* from the expression vector and purified using a combination of affinity, ion exchange and size exclusion chromatography. The purified protein is concentrated to 10 mg/ml and combined with the sgD(R)NA to make a ribonucleoprotein complex. 200 pmol of Cpf1 is combined in separate reaction tubes with 50 pmol, 100 pmol, 200 pmol, 400 pmol, 600 pmol, 800 pmol, 1000 pmol of sgD(R)NA and a reaction buffer. Cpf1-sgD(R)NA complexes are electroporated in replicate into HEK293 cells according to the methods described in Example 7. Cells are grown at 37° C. and genomic DNA is harvested from each reaction after 4, 8, 16, 24, 48, and 72 hours. Genomic DNA is analyzed using PCR and Illumina sequencing to determine that the genome has been edited according to the methods described in Example 7.

D. Genome Editing Using Cpf1 Expression Vectors and sgD(R)NA in Eukaryotic Cells A mammalian expression vector can be constructed by synthesizing a codon-optimized open-reading frame encoding Cpf1 and cloning the open-reading frame into a suitable mammalian expression plasmid (e.g., pcDNA3.1). The coding sequence can include a HA affinity tag for purification or detection of the protein, and a NLS sequence at the C-terminus to drive nuclear localization in eukaryotic cells. The coding sequence can be operably linked to the CMV promoter in the plasmid. Cpf1-expressing plasmids are combined in separate reaction tubes with 50 pmol, 100 pmol, 200 pmol, 400 pmol, 600 pmol, 800 pmol, 1000 pmol of sgD(R)NA and a reaction buffer. Reaction mixtures are electroporated in replicate into HEK293 cells according to methods described in Example 7. Cells are grown at 37° C. and genomic DNA is harvested from each reaction after 4, 8, 16, 24, 48, and 72 hours. Genomic DNA is analyzed using PCR and Illumina sequencing to determine that the genome has been edited according to the methods described in Example 7.

EXAMPLE 13

In Planta Modification of Maize Embryos

This example illustrates the method by which single guide D(R)NA can be used to modify maize embryos. The method presented here is adapted from Svitashev, et. al. (Plant Physiol; 169 (2):931-945 (2015)). Not all of the following steps are required for screening nor must the order of the steps be as presented.

This example illustrates the use of single guide D(R)NAs to guide a Cas endonucleases to cleave chromosomal DNA in maize embryos. Six single guide D(R)NAs (sgD(R)NAs) were designed targeting a region near the liguleless 1 gene and the fertility gene Ms45 (Table 16), and were delivered into a maize line containing a pre-integrated constitutively expressing *S. pyogenes* Cas9 gene. The maize liguleless 1 and Ms45 genomic loci were examined by deep sequencing for the presence of mutations induced by sgD(R)NAs/Cas9 mediated cleavage.

TABLE 16

Maize Liguleless 1 and Ms45 Targeting sgD(R)NA

| Locus | Location | Sequence (RNA bases are bracketed, phosphorothioate bonds are shown with an *) | SEQ ID NO: |
|---|---|---|---|
| liguleless 1 | Chr. 2: 28.45 cM | 5'-T*A*CGCGTACG CGTA[C][G][U][G][U][G] [G][U][U][U][U][A][G][A][G][C] [U][A][G][A][A][A][U][A][G][C] [A][A][G][U][U][A][A][A][A][U] [A][A][G][G][C][U][A][G][U][C] [C][G][U][U][A][U][C][A][A][C] [U][U][G][A][A][A][A][G][U] [G][G][C][A][C][C][G][A][G][U] [C][G][G][U][G][C][U]-3' | 204 |
| liguleless 1 | Chr. 2: 28.45 cM | 5'-T*A*CGCGTACG CGTA[C][G][U][G][U][G] [G][U][U][U][U][A][G][A]GC TATGCT[G][A][A][A] AGCATAGC[A][A][G][U][U][A][A][A][A][U][A][A] [G][G][C][U][A][G][U][C][C][G] [U][U][A][U][C][A][A][C][U][U] [G][A][A][A][A][G][U][G][G] [C][A][C][C][G][A][G][U][C][G][G][U][G][C][U]-3' | 205 |

TABLE 16-continued

Maize Liguleless 1 and Ms45 Targeting sgD(R)NA

| Locus | Location | Sequence (RNA bases are bracketed, phosphorothioate bonds are shown with an *) | SEQ ID NO: |
|---|---|---|---|
| liguleless 1 | Chr. 2: 28.45 cM | 5'-T*A*CGCGTACG CGTA[C][G][U][G][U][G] [G][U][U][U][U][A][G][A]GC TATGCT[G][A][A][A] AGCATAGC[A][A][G][U][U][A][A][A][A][U][A][A] [G][G][C][U][A][G][U][C][C][G] [U][U][A][U][C][A][A][C][U][U] [G][A][A][A][A][A][G][U][G][G] CACCG[A][G][U]CG GTG[C][U]-3' | 206 |
| Ms45 | Chr. 9: 119.15 cM | 5'-G*G*CCGAGGTC GACT[A][C][C][G][G][C] [G][U][U][U][U][A][G][A][G][C] [U][A][G][A][A][A][U][A][G][C] [A][A][G][U][U][A][A][A][A][U] [A][A][G][G][C][U][A][G][U][C] [C][G][U][U][A][U][C][A][A][C] [U][U][G][A][A][A][A][A][G][U] [G][G][C][A][C][C][G][A][G][U] [C][G][G][U][G][C][U]-3' | 224 |
| Ms45 | Chr. 9: 119.15 cM | 5'-G*G*CCGAGGTC GACT[A][C][C][G][G][C] [G][U][U][U][U][A][G][A]GC TATGCT[G][A][A][A] AGCATAGC[A][A][G][U][U][A][A][A][A][U][A][A] [G][G][C][U][A][G][U][C][C][G] [U][U][A][U][C][A][A][C][U][U] [G][A][A][A][A][A][G][U][G][G] [C][A][C][C][G][A][G][U][C][G][G][U][G][C][U]-3' | 225 |
| Ms45 | Chr. 9: 119.15 cM | 5'-G*G*CCGAGGTC GACT[A][C][C][G][G][C] [G][U][U][U][U][A][G][A]GC TATGCT[G][A][A][A] AGCATAGC[A][A][G][U][U][A][A][A][A][U][A][A] [G][G][C][U][A][G][U][C][C][G] [U][U][A][U][C][A][A][C][U][U] [G][A][A][A][A][A][G][U][G][G] CACCG[A][G][U]CG GTG[C][U]-3' | 226 |

A pre-integrated constitutively expressing *S. pyogenes* Cas9 maize line was generated as described in Svitashev et al. (2015).

sgD(R)NAs designs were provided to a commercial manufacturer for synthesis (Eurofins Scientific, Huntsville, Ala.).

sgRNAs (SEQ ID NOS: 207 and 227) were constructed as described in Example 1.

Biolistic-mediated transformation of immature maize embryos (IMEs) derived from the constitutively expressing *S. pyogenes* Cas9 line with the sgD(R)NAs was carried-out as described in Svitashev et. al. (2015). Briefly, 100 ng of each sgD(R)NA was delivered to 60-90 IMEs in the presence of cell-division stimulating genes, ZmODP2 (US Publ. No. 20050257289) and ZmWUS2 (U.S. Pat. No. 7,256,322), as described in Ananiev et. al. (Chromosoma; 118 (2): 157-77 (2009)). Since particle gun transformation can be highly variable, a visual selectable marker DNA expression cassette, MoPAT-DsRED, was also co-delivered with the cell-division promoting genes as described in Svitashev et. al. (2015). Embryos transformed with 100 ng of T7 transcribed single guide RNA (sgRNA) targeting the same region for cleavage (SEQ ID NOS: 207 and 227) served as a positive control and embryos transformed with only the ZmODP2, ZmWUS2 and Mo-PAT-DsRED expression cassettes served as a negative control. After 3 days, the 20-30 most uniformly transformed embryos from each treatment were selected based on DsRED fluorescence, pooled and total genomic DNA was extracted. The region surrounding the intended target site was PCR amplified with Phusion® HighFidelity PCR Master Mix (M0531L, New England Biolabs, Ipswich, Mass.) adding on the sequences necessary for amplicon-specific barcodes and Illumina sequencing using "tailed" primers through two rounds of PCR. The primers used in the primary PCR reaction are shown in Table 17 and the primers used in the secondary PCR reaction were SEQ ID NO: 214 and 215.

TABLE 17

PCR Primer Sequences

| ID | Sample | Primers |
|---|---|---|
| BARCODING PRIMER set-37 | SEQ ID NO. 204 | SEQ ID NOs: 208, 209 |
| BARCODING PRIMER set-38 | SEQ ID NO. 205 | SEQ ID NOs: 208, 210 |
| BARCODING PRIMER set-39 | SEQ ID NO. 206 | SEQ ID NOs: 208, 211 |
| BARCODING PRIMER set-40 | SEQ ID NO. 207 | SEQ ID NOs: 208, 212 |
| BARCODING PRIMER set-41 | No guide RNA (negative control) | SEQ ID NOs: 208, 213 |
| BARCODING PRIMER set-42 | SEQ ID NO. 224 | SEQ ID NOs: 228, 229 |
| BARCODING PRIMER set-43 | SEQ ID NO. 225 | SEQ ID NOs: 228, 230 |
| BARCODING PRIMER set-44 | SEQ ID NO. 226 | SEQ ID NOs: 228, 231 |
| BARCODING PRIMER set-45 | SEQ ID NO. 227 | SEQ ID NOs: 228, 232 |
| BARCODING PRIMER set-46 | No guide RNA (negative control) | SEQ ID NOs: 228, 233 |

The resulting PCR amplifications were purified with a Qiagen PCR purification spin column, concentration measured with a Hoechst dye-based fluorometric assay, combined in an equimolar ratio, and single read 100 nucleotide-length deep sequencing was performed on the Illumina MiSeq Personal Sequencer with a 25% (v/v) spike of PhiX control v3 (Illumina, FC-110-3001) to off-set sequence bias. Only those reads with a ≥1 nucleotide indel arising within the 10 nucleotide window centered over the expected site of cleavage and not found in a similar level in the negative control were classified as mutant. Mutant reads with the same mutation were counted and collapsed into a single read and visually confirmed as having a mutation arising within the expected site of cleavage. The total numbers of visually confirmed mutations were then used to calculate the percent mutant reads based on the total number of reads of an appropriate length containing a perfect match to the barcode and forward primer.

As shown in Table 18, mutations were recovered in all treatments indicating that sgD(R)NAs may be used to guide Cas endonucleases to cleave maize cellular chromosomal DNA. Furthermore, certain sgD(R)NA designs (SEQ ID NOS. 205 and 226) exhibited mutation frequencies near that of the T7 transcribed sgRNA (SEQ ID NOS. 207 and 227). Examples of the mutations recovered with the sgD(R)NAs are shown in FIG. 14A (corresponding to SEQ ID NOs: 217-223, wherein SEQ ID NO: 216 is the reference maize sequence comprising the liguleless 1 target locus) and FIG. 14B (corresponding to SEQ ID NOS: 235-254, wherein SEQ ID NO: 234 is the reference maize sequence comprising the Ms45 target locus).

TABLE 18

Mutant Reads at maize liguleless 1 and Ms45 Target Loci Produced by sgD(R)NA/Cas Endonuclease System Compared to the sgRNA/Cas Endonuclease System

| Treatment | Total Number of Reads | Number of Mutant Reads |
|---|---|---|
| Ligueless 1 No Guide RNA (Negative Control) | 2,849,145 | 0 |
| SEQ ID NO. 207 | 3,155,695 | 552 |
| SEQ ID NO. 204 | 2,816,705 | 5 |
| SEQ ID NO. 205 | 3,053,967 | 192 |
| SEQ ID NO. 206 | 2,979,282 | 9 |
| Ms45 No Guide RNA (Negative Control) | 1,248,142 | 16 |
| SEQ ID NO. XX4 | 1,194,050 | 8,784 |
| SEQ ID NO. XX1 | 1,192,758 | 190 |
| SEQ ID NO. XX2 | 1,206,632 | 114 |
| SEQ ID NO. XX3 | 1,192,110 | 878 |

Although the foregoing disclosure provides description and examples of specific embodiments of the present invention, it is not intended to be limiting in any way and it is within the knowledge of one of skill in the art to modify the examples disclosed in order to adapt a particular method, composition or step to achieve the desired result within the scope of the present invention. All such modifications are intended to be within the scope of the present invention.

What is claimed is:

1. A method of modifying a target nucleic acid molecule comprising: contacting the target nucleic acid molecule having a target sequence with (i) a single polynucleotide comprising (a) a targeting region that comprises deoxyribonucleic acid (DNA) or ribonucleic acid (RNA) and configured to hybridize to the target sequence; and (b) an activating region adjacent to the targeting region that comprises DNA and wherein the activating region comprises a stem loop structure; and (ii) a Cpf1, wherein the Cpf1 binds with the activating region of the single polynucleotide, wherein the contacting of the target nucleic acid molecule with the single polynucleotide and the Cpf1 occurs (A) in vitro, (B) in a non-human cell, or (C) in an isolated cell and wherein the target nucleic acid molecule is cleaved.

2. The method of claim 1, wherein the target nucleic acid molecule comprises DNA.

3. The method of claim 1, wherein the target nucleic acid molecule comprises RNA.

4. The method of claim 1, wherein the target nucleic acid molecule comprises a mixture of DNA and RNA.

5. The method of claim 1, wherein the targeting region comprises a mixture of DNA and RNA.

6. The method of claim 1, wherein the activating region comprises a mixture of DNA and RNA.

7. The method of claim 1, wherein the targeting region comprises a mixture of DNA and RNA and the activating region comprises a mixture of DNA and RNA.

8. The method of claim 1, wherein the contacting of the target nucleic acid molecule with the single polynucleotide and the Cpf1 occurs in vitro.

9. The method of claim 1, wherein the contacting of the target nucleic acid molecule with the single polynucleotide and the Cpf1 occurs in a non-human cell.

10. The method of claim 1, wherein the contacting of the target nucleic acid molecule with the single polynucleotide and the Cpf1 occurs in an isolated cell.

11. The method of claim 10, wherein the cell is selected from the group consisting of a bacterial cell, an archaeal cell, a plant cell, an algal cell, a fungal cell, an invertebrate cell, a vertebrate cell, a mammalian cell and a human cell.

12. The method of claim 1, further comprising providing a donor polynucleotide.

13. A method of modulating transcription of at least one gene within a target nucleic acid molecule comprising: contacting the target nucleic acid molecule having a target sequence with (i) a single polynucleotide comprising (a) a targeting region that comprises deoxyribonucleic acid (DNA) or ribonucleic acid (RNA) and configured to hybridize to the target sequence, wherein the target sequence is within the open reading frame sequence of the at least one gene or is within a promoter sequence of the at least one gene; and (b) an activating region adjacent to the targeting region that comprises DNA and wherein the activating region comprises a stem loop structure; and (ii) a Cpf1, wherein the Cpf1 has no nuclease activity, wherein the Cpf1 binds with the activating region of the single polynucleotide, wherein the targeting region of the single polynucleotide hybridizes to the target sequence, wherein the contacting of the target nucleic acid molecule with the single polynucleotide and the Cpf1 occurs (A) in vitro, (B) in a non-human cell, or (C) in an isolated cell and wherein the transcription of at least one gene within the target nucleic acid molecule is modulated.

14. The method of claim 13, wherein the targeting region comprises a mixture of DNA and RNA.

15. The method of claim 13, wherein the activating region comprises a mixture of DNA and RNA.

16. The method of claim 13, wherein the targeting region comprises a mixture of DNA and RNA and the activating region comprises a mixture of DNA and RNA.

17. The method of claim 13, wherein the contacting of the target nucleic acid molecule with the single polynucleotide and the Cpf1 occurs in vitro.

18. The method of claim 13, wherein the contacting of the target nucleic acid molecule with the single polynucleotide and the Cpf1 occurs in a non-human cell.

19. The method of claim 13, wherein the contacting of the target nucleic acid molecule with the single polynucleotide and the Cpf1 occurs in an isolated cell.

20. The method of claim 19, wherein the cell is selected from the group consisting of a bacterial cell, an archaeal cell, a plant cell, an algal cell, a fungal cell, an invertebrate cell, a vertebrate cell, a mammalian cell and a human cell.

* * * * *

SEQUENCE LISTING

```
<160> NUMBER OF SEQ ID NOS: 254

<210> SEQ ID NO 1
<211> LENGTH: 121
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 1
ggggccacua gggacaggau gucucagagc uaugcugucc uggaaacagg acagcauagc        60
aaguugagau aaggcuaguc cguuaucaac uugaaaaagu ggcaccgagu cggugcuuuu       120
u                                                                       121

<210> SEQ ID NO 2
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
gcaggacagc auagcaaguu gagauaaggc uaguccguua ucaacuugaa aaaguggcac        60
cgagucggug cuu                                                           73

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 3
gagtccgagc agaagaagaa gtctcagagc tatgctgtcc tg            42

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gggtgggggg agtttgctcc gtctcagagc tatgctgtcc tg            42

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtttgtgttt ccataaactg gtctcagagc tatgctgtcc tg            42

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tctgtgataa cctcagttta gtctcagagc tatgctgtcc tg            42

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ggccactgta gtcctccagg gtctcagagc tatgctgtcc tg            42

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gtcccccagc cggtcagcca gtctcagagc tatgctgtcc tg            42

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 9
ggcagccagc atgatgagac gtctcagagc tatgctgtcc tg    42

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gaggagctcc aagaagactg gtctcagagc tatgctgtcc tg    42

<210> SEQ ID NO 11
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gaguccgagc agaagaagaa gucucagagc uaugcugucc ug    42

<210> SEQ ID NO 12
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12 ggguggggggg aguuugcucc gucucagagc uaugcugucc ug    42

<210> SEQ ID NO 13
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
guuuguguuu ccauaaacug gucucagagc uaugcugucc ug    42

<210> SEQ ID NO 14
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
ucugugauaa ccucaguuua gucucagagc uaugcugucc ug    42

<210> SEQ ID NO 15
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 15
ggccacugua guccuccagg gucucagagc uaugcugucc ug                             42

<210> SEQ ID NO 16
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16 guccccccagc cggucagcca gucucagagc uaugcugucc ug                            42

<210> SEQ ID NO 17
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
ggcagccagc augaugagac gucucagagc uaugcugucc ug                             42

<210> SEQ ID NO 18
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
gaggagcucc aagaagacug gucucagagc uaugcugucc ug                             42

<210> SEQ ID NO 19
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 19
gagtccgagc agaagaagaa gucucagagc tatgctgtcc tg                             42

<210> SEQ ID NO 20
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 20 gggtggggg agttugcucc gucucagagc tatgctgtcc tg                              42

<210> SEQ ID NO 21
<211> LENGTH: 42
<212> TYPE: DNA
```

<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 21
gtttgtgttt ccataaacug gucucagagc tatgctgtcc tg        42

<210> SEQ ID NO 22
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 22
tctgtgataa cctcaguuua gucucagagc tatgctgtcc tg        42

<210> SEQ ID NO 23
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 23
ggccactgta gtccuccagg gucucagagc tatgctgtcc tg        42

<210> SEQ ID NO 24
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 24
gtcccccagc cggtcagcca gucucagagc tatgctgtcc tg        42

<210> SEQ ID NO 25
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 25
ggcagccagc atgaugagac gucucagagc tatgctgtcc tg        42

<210> SEQ ID NO 26
<211> LENGTH: 42

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
gaggagctcc aagaagacug gucucagagc tatgctgtcc tg                       42

<210> SEQ ID NO 27
<211> LENGTH: 20
<212> TYPE: DNA
<213> ORGANISM: Homo sapiens

<400> SEQUENCE: 27
gagtccgagc agaagaagaa                                                20

<210> SEQ ID NO 28
<211> LENGTH: 20
<212> TYPE: DNA
<213> ORGANISM: Homo sapiens

<400> SEQUENCE: 28
gagttagagc agaagaagaa                                                20

<210> SEQ ID NO 29
<211> LENGTH: 20
<212> TYPE: DNA
<213> ORGANISM: Homo sapiens

<400> SEQUENCE: 29
aggtactagc agaagaagaa                                                20

<210> SEQ ID NO 30
<211> LENGTH: 20
<212> TYPE: DNA
<213> ORGANISM: Homo sapiens

<400> SEQUENCE: 30
acgtctgagc agaagaagaa                                                20

<210> SEQ ID NO 31
<211> LENGTH: 20
<212> TYPE: DNA
<213> ORGANISM: Homo sapiens

<400> SEQUENCE: 31
aggtgctagc agaagaagaa                                                20

<210> SEQ ID NO 32
<211> LENGTH: 20
<212> TYPE: DNA
<213> ORGANISM: Homo sapiens

<400> SEQUENCE: 32 gggtggggggg agtttgctcc                                               20

<210> SEQ ID NO 33
<211> LENGTH: 20
<212> TYPE: DNA
<213> ORGANISM: Homo sapiens
```

```
<400> SEQUENCE: 33
ggatggaggg agtttgctcc                                              20

<210> SEQ ID NO 34
<211> LENGTH: 20
<212> TYPE: DNA
<213> ORGANISM: Homo sapiens

<400> SEQUENCE: 34 ggggaggggga agtttgctcc                                             20

<210> SEQ ID NO 35
<211> LENGTH: 20
<212> TYPE: DNA
<213> ORGANISM: Homo sapiens

<400> SEQUENCE: 35
gggagggtgg agtttgctcc                                              20

<210> SEQ ID NO 36
<211> LENGTH: 20
<212> TYPE: DNA
<213> ORGANISM: Homo sapiens

<400> SEQUENCE: 36
cgggggaggg agtttgctcc                                              20

<210> SEQ ID NO 37
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ggggccacta gggacaggat gtctcagagc tatgctgtcc tg                     42

<210> SEQ ID NO 38
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 38
ggggccacta gggacaggat gucucagagc tatgctgtcc tg                     42

<210> SEQ ID NO 39
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 39
ggggccacta gggacaggat gtctcagagc tatgctgtcc tg                     42
```

<210> SEQ ID NO 40
<211> LENGTH: 42
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 40
ggggccacta gggacaggau gtctcagagc tatgctgtcc tg            42

<210> SEQ ID NO 41
<211> LENGTH: 42
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 41
ggggccacta gggacaggau gucucagagc tatgctgtcc tg            42

<210> SEQ ID NO 42
<211> LENGTH: 42
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 42
ggggccacua gggacaggau gtctcagagc tatgctgtcc tg            42

<210> SEQ ID NO 43
<211> LENGTH: 42
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 43
ggggccacta gggacaggat gucucagagc tatgctgtcc tg            42

<210> SEQ ID NO 44
<211> LENGTH: 42
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 44
ggggccacta gggacaggau gtctcagagc tatgctgtcc tg            42

<210> SEQ ID NO 45
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 45
ggggccacta gggacaggat gucucagagc tatgctgtcc tg        42

<210> SEQ ID NO 46
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 46
ggggccacua gggacaggau gtctcagagc tatgctgtcc tg        42

<210> SEQ ID NO 47
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 47
ggggccacua gggacaggat gucucagagc tatgctgtcc tg        42

<210> SEQ ID NO 48
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 48
ggggccacua gggacaggat gucucagagc tatgctgtcc tg        42

<210> SEQ ID NO 49
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 49

```
ggggccacta gggacaggau gtcucagagc tatgctgtcc tg                              42
```

<210> SEQ ID NO 50
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 50

```
ggggccacta gggacaggau guctcagagc tatgctgtcc tg                              42
```

<210> SEQ ID NO 51
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 51

```
ggggccacta gggacaggat gtctcagagc tatgctgtcc tg                              42
```

<210> SEQ ID NO 52
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 52

```
ggggccacta gggacaggau gtctcagagc tatgctgtcc tg                              42
```

<210> SEQ ID NO 53
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 53

```
ggggccacta gggacaggat guctcagagc tatgctgtcc tg                              42
```

<210> SEQ ID NO 54
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 54
ggggccacta gggacaggat gtcucagagc tatgctgtcc tg            42

<210> SEQ ID NO 55
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 55
ggggccacta gggacaggat gtctcagagc tatgctgtcc tg            42

<210> SEQ ID NO 56
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 56
ggggccacta gggacaggat guctcagagc tatgctgtcc tg            42

<210> SEQ ID NO 57
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 57
ggggccacta gggacaggat gtcucagagc tatgctgtcc tg            42

<210> SEQ ID NO 58
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 58
ggggccacta gggacaggat gtctcagagc tatgctgtcc tg            42

<210> SEQ ID NO 59
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 59
ggggccacta gggacaggat gtctcagagc tatgctgtcc tg                              42

<210> SEQ ID NO 60
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ggggccacta gggacaggat gtctcagagc tatgctgtcc tg                              42

<210> SEQ ID NO 61
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 61
ggggccacta gggacaggat gtctcagagc tatgctgtcc tg                              42

<210> SEQ ID NO 62
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 62
ggggccacta gggacaggat gtctcagagc tatgctgtcc tg                              42

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
agtaataata cgactcacta tag                                                  23

<210> SEQ ID NO 64
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
taatacgact cactataggg ggccactagg gacaggatgt tttagagcta gaaatagc            58

<210> SEQ ID NO 65
<211> LENGTH: 50
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 65
gttttagagc tagaaatagc aagttaaaat aaggctagtc cgttatcaac        50

<210> SEQ ID NO 66
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 66
aaaaaaagca ccgactcggt gccactttt caagttgata acggactagc        50

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 67
aaaaaaagca ccgactcggt gcc        23

<210> SEQ ID NO 68
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 68
agtaataata cgactcacta tagggggcca ctagggacag gat        43

<210> SEQ ID NO 69
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 69
ggggccacta gggacaggat gtctcagagc tatgctgtcc tg        42

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 70
caggatgtct cagagctatg ctgt        24

<210> SEQ ID NO 71
<211> LENGTH: 58
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 71
agtaataata cgactcacta tagcaggaca gcatagcaag ttgagataag gctagtcc         58

<210> SEQ ID NO 72
<211> LENGTH: 42
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 72
gcaggacagc atagcaagtt gagataaggc tagtccgtta tc                         42

<210> SEQ ID NO 73
<211> LENGTH: 50
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 73
aagcaccgac tcggtgccac tttttcaagt tgataacgga ctagccttat                 50

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 74
aagcaccgac tcggtgccac                                                   20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 75
ccccgttctc ctgtggattc                                                   20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 76
atcctctctg gctccatcgt                                                   20

<210> SEQ ID NO 77
<211> LENGTH: 52
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 77
cactctttcc ctacacgacg ctcttccgat ctgtttctca tctgtgcccc tc        52

<210> SEQ ID NO 78
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ggagttcaga cgtgtgctct tccgatctgt tgcccaccct agtcattg              48

<210> SEQ ID NO 79
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
cactctttcc ctacacgacg ctcttccgat ctccagatgg cacattgtca ga        52

<210> SEQ ID NO 80
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ggagttcaga cgtgtgctct tccgatctcc tagtgactgc cgtctgc               47

<210> SEQ ID NO 81
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
cactctttcc ctacacgacg ctcttccgat ctacatgcac acccatgttt tg        52

<210> SEQ ID NO 82
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ggagttcaga cgtgtgctct tccgatctaa catttccagg tgacaggc              48

<210> SEQ ID NO 83
<211> LENGTH: 52
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 83
cactctttcc ctacacgacg ctcttccgat ctacatgcac acccatgttt tg            52

<210> SEQ ID NO 84
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ggagttcaga cgtgtgctct tccgatctaa catttccagg tgacaggc                 48

<210> SEQ ID NO 85
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
cactctttcc ctacacgacg ctcttccgat ctacatgaaa ttcaaggccg aa            52

<210> SEQ ID NO 86
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ggagttcaga cgtgtgctct tccgatctac ctgtctgtga ggtggagg                 48

<210> SEQ ID NO 87
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
cactctttcc ctacacgacg ctcttccgat ctgctggtgg attatgggaa tg            52

<210> SEQ ID NO 88
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ggagttcaga cgtgtgctct tccgatctag aagacctcat ccttgggg                 48

<210> SEQ ID NO 89
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
cactctttcc ctacacgacg ctcttccgat ctaagaaagg caagaagcct gg         52

<210> SEQ ID NO 90
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ggagttcaga cgtgtgctct tccgatctgc tggcctgaga cattccta             48

<210> SEQ ID NO 91
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
cactctttcc ctacacgacg ctcttccgat cttgtgtact ctccactgcc ca         52

<210> SEQ ID NO 92
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ggagttcaga cgtgtgctct tccgatcttc agaacactcc cttttgcc             48

<210> SEQ ID NO 93
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
cactctttcc ctacacgacg ctcttccgat cttctggcaa ggagagagat gg         52

<210> SEQ ID NO 94
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ggagttcaga cgtgtgctct tccgatctta tattcccagg gccggtta             48

<210> SEQ ID NO 95
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
caagcagaag acggcatacg agattacgtg atgtgactgg agttcagacg tgtgctc        57

<210> SEQ ID NO 96
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
caagcagaag acggcatacg agatattgcc gagtgactgg agttcagacg tgtgctc        57

<210> SEQ ID NO 97
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
caagcagaag acggcatacg agatattggt cagtgactgg agttcagacg tgtgctc        57

<210> SEQ ID NO 98
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
caagcagaag acggcatacg agattaaaaa tggtgactgg agttcagacg tgtgctc        57

<210> SEQ ID NO 99
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
caagcagaag acggcatacg agatatcact gtgtgactgg agttcagacg tgtgctc        57

<210> SEQ ID NO 100
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
caagcagaag acggcatacg agattatttc acgtgactgg agttcagacg tgtgctc        57

<210> SEQ ID NO 101
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
aatgatacgg cgaccaccga gatctacacc gtctaataca ctctttccct acacgacg      58

<210> SEQ ID NO 102
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
aatgatacgg cgaccaccga gatctacact ctctccgaca ctctttccct acacgacg      58

<210> SEQ ID NO 103
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
aatgatacgg cgaccaccga gatctacact cgactagaca ctctttccct acacgacg      58

<210> SEQ ID NO 104
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
aatgatacgg cgaccaccga gatctacact tctagctaca ctctttccct acacgacg      58

<210> SEQ ID NO 105
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
aatgatacgg cgaccaccga gatctacacc ctagagtaca ctctttccct acacgacg      58

<210> SEQ ID NO 106
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
aatgatacgg cgaccaccga gatctacacc tattaagaca ctctttccct acacgacg      58

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
aaaaccaccc ttctctctgg c        21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
ggagattgga gacacggaga g        21

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
aaaggtgcct tttgtgggga        20

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
acaatgggaa ggacagcttc t        21

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
tctccgaact tctgctgagc        20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
tgactagcaa agcaggaggc        20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
aagtccttcc catcgctgtg        20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
gggaatggga atgtgaggca                                              20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gagtccctgc tctcctctga                                              20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
agggaatacc aaaacggcgt                                              20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gtcagaggga cacactgtgg                                              20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
aggagggagc aggaaagtga                                              20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ctcctgctcc atgtgaccac                                              20

```
<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gtagtggcac agtcacagct                                               20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
gagttgcaga ctggagctgt                                               20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ttggaggcaa ggcatctctg                                               20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
aggactcctg ctgagaggag                                               20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ggagaactaa agggcgtgct                                               20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
accaccacat gttctgggtg                                               20
```

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gcttcctctt ccaggctctg                                                   20

<210> SEQ ID NO 127
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 127
ggggccacta gggacaggau guuuuagagc uagaaauagc aaguuaaaau aaggcuaguc        60
cguuaucaac uugaaaaagu ggcaccgagu cggugcu                                97

<210> SEQ ID NO 128
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 128
ggggccacta gggacaggau guuuuagagc uagaaauagc aaguuaaaau aaggcuaguc        60
cguuaucaac uugaaaaagu ggcaccgagu cggugcu                                97

<210> SEQ ID NO 129
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide

<400> SEQUENCE: 129
ggggccacta gggacaggau guuuuagagc tgctgaaaag cauagcaagu uaaaauaagg        60
cuaguccguu aucaacuuga aaaguggca ccgagucggu gcu                          103

<210> SEQ ID NO 130
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide

<400> SEQUENCE: 130

```
gggccacta gggacaggau guuuuagagc tatgctgaaa agcatagcaa guuaaaauaa      60
ggcuaguccg uuaucaacuu gaaaaagugg caccgagucg gugcu                    105
```

<210> SEQ ID NO 131
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide

<400> SEQUENCE: 131

```
ggggccacta gggacaggau guuuuagagc tatgctgaaa agcatagcaa guuaaaauaa     60
ggcuaguccg uuaucaacuu gaaaaagugg caccgagucg gtgcu                    105
```

<210> SEQ ID NO 132
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide

<400> SEQUENCE: 132

```
ggggccacta gggacaggau guuuuagagc tatgctgaaa agcatagcaa guuaaaauaa     60
ggcuaguccg uuaucaacuu gaaaaagugg caccgagucg gtgcu                    105
```

<210> SEQ ID NO 133
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133

```
tacttccaat ccaatgcacc ccgttctcct gtggat                              36
```

<210> SEQ ID NO 134
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134

```
ttatccactt ccaatgttat tactccctcc caggatcctc                          40
```

<210> SEQ ID NO 135
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 135
gccactaggg acaggatguc ucagagctat gctgtcctg                    39

<210> SEQ ID NO 136
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 136
gccactaggg acaggauguc ucagagctat gctgtcctg                    39

<210> SEQ ID NO 137
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 137
gccactaggg acaggatguc ucagagctat gctgtcctg                    39

<210> SEQ ID NO 138
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(15)
<223> OTHER INFORMATION: a, c, t, g, unknown or other
<220> FEATURE:
<221> NAME/KEY: modified_base
<222> LOCATION: (16)..(20)
<223> OTHER INFORMATION: a, c, u, g, unknown or other

<400> SEQUENCE: 138
nnnnnnnnnn nnnnnnnnnn guuuuaguac tctgtaattt taggtatgag gtagac      56

<210> SEQ ID NO 139
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 139
nnnnnnnnnn nnnnnnnnnn guuuaguac tctgtaattt taggtatgag gtagac       56

```
<210> SEQ ID NO 140
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 140
nnnnnnnnnn nnnnnnnnnn guuuuaguac ucugtaatttt taggtatgag gtagac        56

<210> SEQ ID NO 141
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (3)..(4)
<223> OTHER INFORMATION: a, c, u, g, unknown or other
<220> FEATURE:
<221> NAME/KEY: modified_base
<222> LOCATION: (5)..(14)
<223> OTHER INFORMATION: a, c, t, g, unknown or other
<220> FEATURE:
<221> NAME/KEY: modified_base
<222> LOCATION: (15)..(17)
<223> OTHER INFORMATION: a, c, u, g, unknown or other
<220> FEATURE:
<221> NAME/KEY: modified_base
<222> LOCATION: (18)..(18)
<223> OTHER INFORMATION: a, c, t, g, unknown or other
<220> FEATURE:
<221> NAME/KEY: modified_base
<222> LOCATION: (19)..(19)
<223> OTHER INFORMATION: a, c, u, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 141
nnnnnnnnnn nnnnnnnnnn guuuuagtac tctgtaattt taggtatgag gtagac        56

<210> SEQ ID NO 142
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
auuguacuua uaccuaaaau uacagaaucu acuaaaacaa ggcaaaaugc cguguuuauc        60
ucgucaacuu guuggcgaga uuuuu                                           85
```

<210> SEQ ID NO 143
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide
<220> FEATURE:
<221> NAME/KEY: modified_base
<222> LOCATION: (1)..(15)
<223> OTHER INFORMATION: a, c, t, g, unknown or other
<220> FEATURE:
<221> NAME/KEY: modified_base
<222> LOCATION: (16)..(20)
<223> OTHER INFORMATION: a, c, u, g, unknown or other

<400> SEQUENCE: 143
nnnnnnnnnn nnnnnnnnnn guuuuaguac tctggaaaca gaaucuacua aaaacaaggc    60
caaaaugccg guguuuaucu ucgucaacuu uguuggcgag gauuuu                  106

<210> SEQ ID NO 144
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 144
nnnnnnnnnn nnnnnnnnnn guuuuaguac tctggaaaca gaaucuacua aaaacaaggc    60
caaaaugccg guguuuaucu ucgucaacuu uguuggcgag gauuuu                  106

<210> SEQ ID NO 145
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 145
nnnnnnnnnn nnnnnnnnnn guuuuaguac ucuggaaaca gaaucuacua aaaacaaggc    60
caaaaugccg guguuuaucu ucgucaacuu uguuggcgag gauuuu                  106

<210> SEQ ID NO 146
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

```
<220> FEATURE:
<223> OTHER INFORMATION: Description of Combined DNA/RNA Molecule:
      Synthetic polynucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (3)..(4)
<223> OTHER INFORMATION: a, c, u, g, unknown or other
<220> FEATURE:
<221> NAME/KEY: modified_base
<222> LOCATION: (5)..(14)
<223> OTHER INFORMATION: a, c, t, g, unknown or other
<220> FEATURE:
<221> NAME/KEY: modified_base
<222> LOCATION: (15)..(17)
<223> OTHER INFORMATION: a, c, u, g, unknown or other
<220> FEATURE:
<221> NAME/KEY: modified_base
<222> LOCATION: (18)..(18)
<223> OTHER INFORMATION: a, c, t, g, unknown or other
<220> FEATURE:
<221> NAME/KEY: modified_base
<222> LOCATION: (19)..(19)
<223> OTHER INFORMATION: a, c, u, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 146
nnnnnnnnnn nnnnnnnnnn guuuuagtac tctggaaaca gaaucuacua aaaacaaggc      60
caaaaugccg guguuuaucu ucgucaacuu uguuggcgag gauuuu                    106

<210> SEQ ID NO 147
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(15)
<223> OTHER INFORMATION: a, c, t, g, unknown or other
<220> FEATURE:
<221> NAME/KEY: modified_base
<222> LOCATION: (16)..(20)
<223> OTHER INFORMATION: a, c, u, g, unknown or other

<400> SEQUENCE: 147
nnnnnnnnnn nnnnnnnnnn guuuuguac tctcaagatt taagtaactg tacaac           56

<210> SEQ ID NO 148
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 148
```

```
nnnnnnnnnn nnnnnnnnnn guuuuugtac tctcaagatt taagtaactg tacaac        56
```

<210> SEQ ID NO 149
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 149

```
nnnnnnnnnn nnnnnnnnnn guuuuuguac uctcaagatt taagtaactg tacaac        56
```

<210> SEQ ID NO 150
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150

```
cuuacacagu acuuaaauc uugcagaagc uacaaagaua aggcuucaug ccgaaaucaa      60
cacccuguca uuuuauggca ggguguuuu                                       89
```

<210> SEQ ID NO 151
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide
<220> FEATURE:
<221> NAME/KEY: modified_base
<222> LOCATION: (1)..(15)
<223> OTHER INFORMATION: a, c, t, g, unknown or other
<220> FEATURE:
<221> NAME/KEY: modified_base
<222> LOCATION: (16)..(20)
<223> OTHER INFORMATION: a, c, u, g, unknown or other

<400> SEQUENCE: 151

```
nnnnnnnnnn nnnnnnnnnn guuuuuguac tcgaaagaag cuacaaagau uaaggcuuca     60
augccgaaau ucaacacccu ugucauuuua auggcagggu uguuuu                   106
```

<210> SEQ ID NO 152
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 152
nnnnnnnnnn nnnnnnnnnn guuuuguac tcgaaagaag cuacaaagau uaaggcuuca    60
augccgaaau ucaacacccu ugucauuuua auggcagggu uguuuu    106

<210> SEQ ID NO 153
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 153
nnnnnnnnnn nnnnnnnnnn guuuuguac ucgaaagaag cuacaaagau uaaggcuuca    60
augccgaaau ucaacacccu ugucauuuua auggcagggu uguuuu    106

<210> SEQ ID NO 154
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(15)
<223> OTHER INFORMATION: a, c, t, g, unknown or other
<220> FEATURE:
<221> NAME/KEY: modified_base
<222> LOCATION: (16)..(20)
<223> OTHER INFORMATION: a, c, u, g, unknown or other

<400> SEQUENCE: 154
nnnnnnnnnn nnnnnnnnnn guuguagcuc ccattctcat ttcgcagtgc tacaat    56

<210> SEQ ID NO 155
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 155
nnnnnnnnnn nnnnnnnnnn guuguagctc ccattctcat ttcgcagtgc tacaat    56

<210> SEQ ID NO 156
<211> LENGTH: 56
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 156
nnnnnnnnnn nnnnnnnnnn guuguagcuc ccattctcat ttcgcagtgc tacaat          56

<210> SEQ ID NO 157
<211> LENGTH: 119
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 157
auugucgcac ugcgaaauga gaaccguugc uacaauaagg ccgucugaaa agaugugccg      60
caacgcucug ccccuuaaag cuucugcuuu aaggggcauc guuuauuucg guuaaaaau     119

<210> SEQ ID NO 158
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide
<220> FEATURE:
<221> NAME/KEY: modified_base
<222> LOCATION: (1)..(15)
<223> OTHER INFORMATION: a, c, t, g, unknown or other
<220> FEATURE:
<221> NAME/KEY: modified_base
<222> LOCATION: (16)..(20)
<223> OTHER INFORMATION: a, c, u, g, unknown or other

<400> SEQUENCE: 158
nnnnnnnnnn nnnnnnnnnn guuguagcuc ccattctcga aagagaaccg guugcuacaa      60
auaaggccgu ucugaaaaga augugccgca acgcucugc ccccuuaaag                 110

<210> SEQ ID NO 159
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 159
nnnnnnnnnn nnnnnnnnnn guuguagcuc ccattctcga aagagaaccg guugcuacaa      60
auaaggccgu ucugaaaaga augugccgca acgcucugc ccccuuaaag                 110

<210> SEQ ID NO 160
```

```
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 160
nnnnnnnnnn nnnnnnnnnn guuguagcuc ccattctcga aagagaaccg guugcuacaa      60
auaaggccgu ucugaaaaga augugccgca aacgcucugc ccccuuaaag                110

<210> SEQ ID NO 161
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(14)
<223> OTHER INFORMATION: a, c, t, g, unknown or other
<220> FEATURE:
<221> NAME/KEY: modified_base
<222> LOCATION: (15)..(20)
<223> OTHER INFORMATION: a, c, u, g, unknown or other

<400> SEQUENCE: 161
nnnnnnnnnn nnnnnnnnnn guuuuuguac tctcaagatt taagtaaccg taaaac          56

<210> SEQ ID NO 162
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 162
nnnnnnnnnn nnnnnnnnnn guuuuugtac tctcaagatt taagtaaccg taaaac          56

<210> SEQ ID NO 163
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(20)
<223> OTHER INFORMATION: a, c, t, g, unknown or other
```

-continued

<400> SEQUENCE: 163
nnnnnnnnnn nnnnnnnnnn guuuuuguac ucucaagauu uaaguaaccg uaaaac      56

<210> SEQ ID NO 164
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
cuugcacggu uacuuaaauc uugcugagcc uacaaagaua aggcuuuaug ccgaauucaa      60
gcaccccaug uuuugacaug aggugcuuuu                                      90

<210> SEQ ID NO 165
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide
<220> FEATURE:
<221> NAME/KEY: modified_base
<222> LOCATION: (1)..(15)
<223> OTHER INFORMATION: a, c, t, g, unknown or other
<220> FEATURE:
<221> NAME/KEY: modified_base
<222> LOCATION: (16)..(20)
<223> OTHER INFORMATION: a, c, u, g, unknown or other

<400> SEQUENCE: 165
nnnnnnnnnn nnnnnnnnnn guuuuuguac ucgaaagagc cuacaaagau uaaggcuuua      60
augccgaauu ucaagcaccc ccauguuuug acaugaggu ugcuuu                    106

<210> SEQ ID NO 166
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 166
nnnnnnnnnn nnnnnnnnnn guuuuuguac ucgaaagagc cuacaaagau uaaggcuuua      60
augccgaauu ucaagcaccc ccauguuuug acaugaggu ugcuuu                    106

<210> SEQ ID NO 167
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide

```
<220> FEATURE:
<221> NAME/KEY: modified_base
<222> LOCATION: (1)..(20)
<223> OTHER INFORMATION: a, c, t, g, unknown or other

<400> SEQUENCE: 167
nnnnnnnnnn nnnnnnnnnn guuuuuguac tcgaaagagc cuacaaagau uaaggcuuua    60
augccgaauu ucaagcaccc ccauguuuug gacaugaggu ugcuuu                  106

<210> SEQ ID NO 168
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
aauuucuacu g                                                         11

<210> SEQ ID NO 169
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 169
aauutctacu g                                                         11

<210> SEQ ID NO 170
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
aauuucuacu g                                                         11

<210> SEQ ID NO 171
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 171
aauutctacu g                                                         11

<210> SEQ ID NO 172
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

<222> LOCATION: (9)..(33)
<223> OTHER INFORMATION: a, c, u, g, unknown or other

<400> SEQUENCE: 172
uuguagaunn nnnnnnnnnn nnnnnnnnnn nnn                                   33

<210> SEQ ID NO 173
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(33)
<223> OTHER INFORMATION: a, c, u, g, unknown or other

<400> SEQUENCE: 173
uuguagaunn nnnnnnnnnn nnnnnnnnnn nnn                                   33

<210> SEQ ID NO 174
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(28)
<223> OTHER INFORMATION: a, c, u, g, unknown or other

<400> SEQUENCE: 174
uuguagaunn nnnnnnnnnn nnnnnnnn                                         28

<210> SEQ ID NO 175
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(28)
<223> OTHER INFORMATION: a, c, u, g, unknown or other

<400> SEQUENCE: 175
uuguagaunn nnnnnnnnnn nnnnnnnn                                         28

<210> SEQ ID NO 176
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(33)
<223> OTHER INFORMATION: a, c, t, g, unknown or other

<400> SEQUENCE: 176
uuguagaunn nnnnnnnnnn nnnnnnnnnn nnn                                   33

```
<210> SEQ ID NO 177
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(10)
<223> OTHER INFORMATION: a, c, u, g, unknown or other
<220> FEATURE:
<221> NAME/KEY: modified_base
<222> LOCATION: (11)..(33)
<223> OTHER INFORMATION: a, c, t, g, unknown or other

<400> SEQUENCE: 177
uuguagaunn nnnnnnnnnn nnnnnnnnnn nnn                              33

<210> SEQ ID NO 178
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(13)
<223> OTHER INFORMATION: a, c, u, g, unknown or other
<220> FEATURE:
<221> NAME/KEY: modified_base
<222> LOCATION: (14)..(33)
<223> OTHER INFORMATION: a, c, t, g, unknown or other

<400> SEQUENCE: 178
uuguagaunn nnnnnnnnnn nnnnnnnnnn nnn                              33

<210> SEQ ID NO 179
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(18)
<223> OTHER INFORMATION: a, c, u, g, unknown or other
<220> FEATURE:
<221> NAME/KEY: modified_base
<222> LOCATION: (19)..(33)
<223> OTHER INFORMATION: a, c, t, g, unknown or other

<400> SEQUENCE: 179
uuguagaunn nnnnnnnnnn nnnnnnnnnn nnn                              33

<210> SEQ ID NO 180
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(33)
<223> OTHER INFORMATION: a, c, u, g, unknown or other

<400> SEQUENCE: 180
uugtagaunn nnnnnnnnnn nnnnnnnnnn nnn                                    33

<210> SEQ ID NO 181
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(33)
<223> OTHER INFORMATION: a, c, u, g, unknown or other

<400> SEQUENCE: 181
uugtagaunn nnnnnnnnnn nnnnnnnnnn nnn                                    33

<210> SEQ ID NO 182
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(28)
<223> OTHER INFORMATION: a, c, u, g, unknown or other

<400> SEQUENCE: 182
uugtagaunn nnnnnnnnnn nnnnnnnn                                          28

<210> SEQ ID NO 183
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(28)
<223> OTHER INFORMATION: a, c, u, g, unknown or other

<400> SEQUENCE: 183
uuguagaunn nnnnnnnnnn nnnnnnnn                                          28

<210> SEQ ID NO 184
<211> LENGTH: 33
<212> TYPE: DNA
<213> ORGANISM: Artificial Sequence
<220> FEATURE:
<223> OTHER INFORMATION: Description of Artificial Sequence: Synthetic
```

-continued

```
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(33)
<223> OTHER INFORMATION: a, c, t, g, unknown or other

<400> SEQUENCE: 184
uugtagaunn nnnnnnnnnn nnnnnnnnnn nnn                                  33

<210> SEQ ID NO 185
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(10)
<223> OTHER INFORMATION: a, c, u, g, unknown or other
<220> FEATURE:
<221> NAME/KEY: modified_base
<222> LOCATION: (11)..(33)
<223> OTHER INFORMATION: a, c, t, g, unknown or other

<400> SEQUENCE: 185
uugtagaunn nnnnnnnnnn nnnnnnnnnn nnn                                  33

<210> SEQ ID NO 186
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(13)
<223> OTHER INFORMATION: a, c, u, g, unknown or other
<220> FEATURE:
<221> NAME/KEY: modified_base
<222> LOCATION: (14)..(33)
<223> OTHER INFORMATION: a, c, t, g, unknown or other

<400> SEQUENCE: 186
uugtagaunn nnnnnnnnnn nnnnnnnnnn nnn                                  33

<210> SEQ ID NO 187
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(18)
<223> OTHER INFORMATION: a, c, u, g, unknown or other
<220> FEATURE:
<221> NAME/KEY: modified_base
<222> LOCATION: (19)..(33)
```

<223> OTHER INFORMATION: a, c, t, g, unknown or other

<400> SEQUENCE: 187
uugtagaunn nnnnnnnnnn nnnnnnnnnn nnn        33

<210> SEQ ID NO 188
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(44)
<223> OTHER INFORMATION: a, c, u, g, unknown or other

<400> SEQUENCE: 188
aauuucuacu guugtagaun nnnnnnnnnn nnnnnnnnnn nnnn        44

<210> SEQ ID NO 189
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(44)
<223> OTHER INFORMATION: a, c, u, g, unknown or other

<400> SEQUENCE: 189
aauutctacu guuguagaun nnnnnnnnnn nnnnnnnnnn nnnn        44

<210> SEQ ID NO 190
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(44)
<223> OTHER INFORMATION: a, c, u, g, unknown or other

<400> SEQUENCE: 190
aauutctacu guugtagaun nnnnnnnnnn nnnnnnnnnn nnnn        44

<210> SEQ ID NO 191
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base

```
<222> LOCATION: (20)..(44)
<223> OTHER INFORMATION: a, c, t, g, unknown or other

<400> SEQUENCE: 191
aauuucuacu guuguagaun nnnnnnnnnn nnnnnnnnnn nnnn          44

<210> SEQ ID NO 192
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(44)
<223> OTHER INFORMATION: a, c, t, g, unknown or other

<400> SEQUENCE: 192
aauutctacu guuguagaun nnnnnnnnnn nnnnnnnnnn nnnn          44

<210> SEQ ID NO 193
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, u, g, unknown or other
<220> FEATURE:
<221> NAME/KEY: modified_base
<222> LOCATION: (22)..(44)
<223> OTHER INFORMATION: a, c, t, g, unknown or other

<400> SEQUENCE: 193
aauutctacu guuguagaun nnnnnnnnnn nnnnnnnnnn nnnn          44

<210> SEQ ID NO 194
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(24)
<223> OTHER INFORMATION: a, c, u, g, unknown or other
<220> FEATURE:
<221> NAME/KEY: modified_base
<222> LOCATION: (25)..(44)
<223> OTHER INFORMATION: a, c, t, g, unknown or other

<400> SEQUENCE: 194
aauutctacu guuguagaun nnnnnnnnnn nnnnnnnnnn nnnn          44

<210> SEQ ID NO 195
<211> LENGTH: 44
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(29)
<223> OTHER INFORMATION: a, c, u, g, unknown or other
<220> FEATURE:
<221> NAME/KEY: modified_base
<222> LOCATION: (30)..(44)
<223> OTHER INFORMATION: a, c, t, g, unknown or other

<400> SEQUENCE: 195
aauutctacu guuguagaun nnnnnnnnnn nnnnnnnnnn nnnn              44

<210> SEQ ID NO 196
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(44)
<223> OTHER INFORMATION: a, c, t, g, unknown or other

<400> SEQUENCE: 196
aauuucuacu guugtagaun nnnnnnnnnn nnnnnnnnnn nnnn              44

<210> SEQ ID NO 197
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, u, g, unknown or other
<220> FEATURE:
<221> NAME/KEY: modified_base
<222> LOCATION: (22)..(44)
<223> OTHER INFORMATION: a, c, t, g, unknown or other

<400> SEQUENCE: 197
aauuucuacu guugtagaun nnnnnnnnnn nnnnnnnnnn nnnn              44

<210> SEQ ID NO 198
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(24)
<223> OTHER INFORMATION: a, c, u, g, unknown or other
```

```
<220> FEATURE:
<221> NAME/KEY: modified_base
<222> LOCATION: (25)..(44)
<223> OTHER INFORMATION: a, c, t, g, unknown or other

<400> SEQUENCE: 198
aauuucuacu guugtagaun nnnnnnnnnn nnnnnnnnnn nnnn            44

<210> SEQ ID NO 199
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(29)
<223> OTHER INFORMATION: a, c, u, g, unknown or other
<220> FEATURE:
<221> NAME/KEY: modified_base
<222> LOCATION: (30)..(44)
<223> OTHER INFORMATION: a, c, t, g, unknown or other

<400> SEQUENCE: 199
aauuucuacu guugtagaun nnnnnnnnnn nnnnnnnnnn nnnn            44

<210> SEQ ID NO 200
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(44)
<223> OTHER INFORMATION: a, c, t, g, unknown or other

<400> SEQUENCE: 200
aauutctacu guugtagaun nnnnnnnnnn nnnnnnnnnn nnnn            44

<210> SEQ ID NO 201
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, u, g, unknown or other
<220> FEATURE:
<221> NAME/KEY: modified_base
<222> LOCATION: (22)..(44)
<223> OTHER INFORMATION: a, c, t, g, unknown or other

<400> SEQUENCE: 201
aauutctacu guugtagaun nnnnnnnnnn nnnnnnnnnn nnnn            44

<210> SEQ ID NO 202
```

<211> LENGTH: 44
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide
<220> FEATURE:
<221> NAME/KEY: modified_base
<222> LOCATION: (20)..(24)
<223> OTHER INFORMATION: a, c, u, g, unknown or other
<220> FEATURE:
<221> NAME/KEY: modified_base
<222> LOCATION: (25)..(44)
<223> OTHER INFORMATION: a, c, t, g, unknown or other

<400> SEQUENCE: 202
aauutctacu guugtagaun nnnnnnnnnn nnnnnnnnnn nnnn             44

<210> SEQ ID NO 203
<211> LENGTH: 44
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide
<220> FEATURE:
<221> NAME/KEY: modified_base
<222> LOCATION: (20)..(29)
<223> OTHER INFORMATION: a, c, u, g, unknown or other
<220> FEATURE:
<221> NAME/KEY: modified_base
<222> LOCATION: (30)..(44)
<223> OTHER INFORMATION: a, c, t, g, unknown or other

<400> SEQUENCE: 203
aauutctacu guugtagaun nnnnnnnnnn nnnnnnnnnn nnnn             44

<210> SEQ ID NO 204
<211> LENGTH: 97
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Description of Combined DNA/RNA Molecule:
Synthetic polynucleotide

<400> SEQUENCE: 204
tacgcgtacg cgtacgugug guuuuagagc uagaaauagc aaguuaaaau aaggcuaguc    60
cguuaucaac uugaaaaagu ggcaccgagu cggugcu                            97

<210> SEQ ID NO 205
<211> LENGTH: 105
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Description of Combined DNA/RNA Molecule:
Synthetic polynucleotide

<400> SEQUENCE: 205
tacgcgtacg cgtacgugug guuuuagagc tatgctgaaa agcatagcaa guuaaaauaa    60
ggcuaguccg uuaucaacuu gaaaaagugg caccgagucg gugcu    105

<210> SEQ ID NO 206
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide

<400> SEQUENCE: 206
tacgcgtacg cgtacgugug guuuuagagc tatgctgaaa agcatagcaa guuaaaauaa    60
ggcuaguccg uuaucaacuu gaaaaagugg caccgagucg gtgcu    105

<210> SEQ ID NO 207
<211> LENGTH: 98
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
ggcguacgcg uacgguggu uuuagagcua gaaauagcaa guuaaaauaa ggcuaguccg    60
uuaucaacuu gaaaaagugg caccgagucg gugcuuuu    98

<210> SEQ ID NO 208
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
ctacactctt tccctacacg acgctcttcc gatctaaggc gcaaatgagt agcagcgcac    60

<210> SEQ ID NO 209
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
caagcagaag acggcatacg agctcttccg atctcacctg ctgggaattg taccgta    57

<210> SEQ ID NO 210
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
ctacactctt tccctacacg acgctcttcc gatctggaac gcaaatgagt agcagcgcac    60

<210> SEQ ID NO 211
<211> LENGTH: 60
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 211
ctacactctt tccctacacg acgctcttcc gatctccttc gcaaatgagt agcagcgcac    60

<210> SEQ ID NO 212
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
ctacactctt tccctacacg acgctcttcc gatctgaagc gcaaatgagt agcagcgcac    60

<210> SEQ ID NO 213
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
ctacactctt tccctacacg acgctcttcc gatctaggac gcaaatgagt agcagcgcac    60

<210> SEQ ID NO 214
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
aatgatacgg cgaccaccga gatctacact ctttccctac acg                     43

<210> SEQ ID NO 215
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
caagcagaag acggcata                                                 18

<210> SEQ ID NO 216
<211> LENGTH: 56
<212> TYPE: DNA
<213> ORGANISM: Zea mays

<400> SEQUENCE: 216
cagcgcacgt atatatacgc gtacgcgtac gtgtgaggta tatatcct ccgccg         56

<210> SEQ ID NO 217
<211> LENGTH: 55
<212> TYPE: DNA
<213> ORGANISM: Zea mays

<400> SEQUENCE: 217

```
cagcgcacgt atatatacgc gtacgcgtac gttgaggtat atatatcctc cgccg         55

<210> SEQ ID NO 218
<211> LENGTH: 57
<212> TYPE: DNA
<213> ORGANISM: Zea mays

<400> SEQUENCE: 218
cagcgcacgt atatatacgc gtacgcgtac gttgtgaggt atatatatcc tccgccg       57

<210> SEQ ID NO 219
<211> LENGTH: 55
<212> TYPE: DNA
<213> ORGANISM: Zea mays

<400> SEQUENCE: 219
cagcgcacgt atatatacgc gtacgcgtac ggtgaggtat atatatcctc cgccg         55

<210> SEQ ID NO 220
<211> LENGTH: 27
<212> TYPE: DNA
<213> ORGANISM: Zea mays

<400> SEQUENCE: 220
cagcgcacgt atatatatcc tccgccg                                        27

<210> SEQ ID NO 221
<211> LENGTH: 55
<212> TYPE: DNA
<213> ORGANISM: Zea mays

<400> SEQUENCE: 221
cagcgcacgt atatatacgc gtacgcgtac gttgaggtat atatatcctc cgccg         55

<210> SEQ ID NO 222
<211> LENGTH: 52
<212> TYPE: DNA
<213> ORGANISM: Zea mays

<400> SEQUENCE: 222
cagcgcacgt atatatacgc gtacgcgtat gaggtatata tatcctccgc cg            52

<210> SEQ ID NO 223
<211> LENGTH: 55
<212> TYPE: DNA
<213> ORGANISM: Zea mays

<400> SEQUENCE: 223
cagcgcacgt atatatacgc gtacgcgtac gttgaggtat atatatcctc cgccg         55

<210> SEQ ID NO 224
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 224
ggccgaggtc gactaccggc guuuuagagc uagaaauagc aaguuaaaau aaggcuaguc    60
cguuaucaac uugaaaaagu ggcaccgagu cggugcu                             97
```

<210> SEQ ID NO 225
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide

<400> SEQUENCE: 225
ggccgaggtc gactaccggc guuuuagagc tatgctgaaa agcatagcaa guuaaaauaa      60
ggcuaguccg uuaucaacuu gaaaaagugg caccgagucg gugcu                    105

<210> SEQ ID NO 226
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide

<400> SEQUENCE: 226
ggccgaggtc gactaccggc guuuuagagc tatgctgaaa agcatagcaa guuaaaauaa      60
ggcuaguccg uuaucaacuu gaaaaagugg caccgagucg gtgcu                    105

<210> SEQ ID NO 227
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 227
gggccgaggu cgacuaccgg cguuuuagag cuaugcuguu uuggaaacaa aacagcauag      60
caaguuaaaa uaaggcuagu ccguuaucaa cuugaaaaag uggcaccgag ucggugcuuu    120
uuuu                                                                 124

<210> SEQ ID NO 228
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
caagcagaag acggcatacg agctcttccg atctgccggc tggcattgtc tctg           54

<210> SEQ ID NO 229
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
ctacactctt tccctacacg acgctcttcc gatctttccg gacccgttcg gcctcagt       58

<210> SEQ ID NO 230
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
ctacactctt tccctacacg acgctcttcc gatctggaag gacccgttcg gcctcagt        58

<210> SEQ ID NO 231
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
ctacactctt tccctacacg acgctcttcc gatctccttg gacccgttcg gcctcagt        58

<210> SEQ ID NO 232
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
ctacactctt tccctacacg acgctcttcc gatcttcctg gacccgttcg gcctcagt        58

<210> SEQ ID NO 233
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
ctacactctt tccctacacg acgctcttcc gatctaaggg gacccgttcg gcctcagt        58

<210> SEQ ID NO 234
<211> LENGTH: 39
<212> TYPE: DNA
<213> ORGANISM: Zea mays

<400> SEQUENCE: 234
agtccgctgg ccgaggtcga ctaccggccg gtgaagcac                             39

<210> SEQ ID NO 235
<211> LENGTH: 40
<212> TYPE: DNA
<213> ORGANISM: Zea mays

<400> SEQUENCE: 235
agtccgctgg ccgaggtcga ctaccaggcc ggtgaagcac                            40

<210> SEQ ID NO 236
<211> LENGTH: 40
<212> TYPE: DNA
<213> ORGANISM: Zea mays

```
<400> SEQUENCE: 236
agtccgctgg ccgaggtcga cttgccggcc ggtgaagcac                    40

<210> SEQ ID NO 237
<211> LENGTH: 22
<212> TYPE: DNA
<213> ORGANISM: Zea mays

<400> SEQUENCE: 237
agtccgctgg ccggtgaagc ac                                       22

<210> SEQ ID NO 238
<211> LENGTH: 37
<212> TYPE: DNA
<213> ORGANISM: Zea mays

<400> SEQUENCE: 238
agtccgctgg ccgaggtcga ccaggccggt gaagcac                       37

<210> SEQ ID NO 239
<211> LENGTH: 40
<212> TYPE: DNA
<213> ORGANISM: Zea mays

<400> SEQUENCE: 239
agtccgctgg ccgaggtcga ctacctggcc ggtgaagcac                    40

<210> SEQ ID NO 240
<211> LENGTH: 18
<212> TYPE: DNA
<213> ORGANISM: Zea mays

<400> SEQUENCE: 240
agtccgccag tgaagcac                                            18

<210> SEQ ID NO 241
<211> LENGTH: 38
<212> TYPE: DNA
<213> ORGANISM: Zea mays

<400> SEQUENCE: 241
agtccgctgg ccgaggtcga ctacggccgg tgaagcac                      38

<210> SEQ ID NO 242
<211> LENGTH: 40
<212> TYPE: DNA
<213> ORGANISM: Zea mays

<400> SEQUENCE: 242
agtccgctgg ccgaggtcga ctacccggcc ggtgaagcac                    40

<210> SEQ ID NO 243
<211> LENGTH: 40
<212> TYPE: DNA
<213> ORGANISM: Zea mays

<400> SEQUENCE: 243
agtccgctgg ccgaggtcga ctaccaggcc ggtgaagcac                    40

<210> SEQ ID NO 244
<211> LENGTH: 22
<212> TYPE: DNA
<213> ORGANISM: Zea mays
```

```
<400> SEQUENCE: 244
agtccgctgg ccggtgaagc ac                                              22

<210> SEQ ID NO 245
<211> LENGTH: 38
<212> TYPE: DNA
<213> ORGANISM: Zea mays

<400> SEQUENCE: 245
agtccgctgg ccgaggtcga ctacggccgg tgaagcac                             38

<210> SEQ ID NO 246
<211> LENGTH: 37
<212> TYPE: DNA
<213> ORGANISM: Zea mays

<400> SEQUENCE: 246
agtccgctgg ccgaggtcga cttggccggt gaagcac                              37

<210> SEQ ID NO 247
<211> LENGTH: 40
<212> TYPE: DNA
<213> ORGANISM: Zea mays

<400> SEQUENCE: 247
agtccgctgg ccgaggtcga ctaccaggcc ggtgaagcac                           40

<210> SEQ ID NO 248
<211> LENGTH: 38
<212> TYPE: DNA
<213> ORGANISM: Zea mays

<400> SEQUENCE: 248
agtccgctgg ccgaggtcga ctacggccgg tgaagcac                             38

<210> SEQ ID NO 249
<211> LENGTH: 40
<212> TYPE: DNA
<213> ORGANISM: Zea mays

<400> SEQUENCE: 249
agtccgctgg ccgaggtcga ctacctggcc ggtgaagcac                           40

<210> SEQ ID NO 250
<211> LENGTH: 40
<212> TYPE: DNA
<213> ORGANISM: Zea mays

<400> SEQUENCE: 250
agtccgctgg ccgaggtcga ctacccggcc ggtgaagcac                           40

<210> SEQ ID NO 251
<211> LENGTH: 28
<212> TYPE: DNA
<213> ORGANISM: Zea mays

<400> SEQUENCE: 251
agtccgctgg tcaaggccgg cgaagcac                                        28

<210> SEQ ID NO 252
<211> LENGTH: 22
<212> TYPE: DNA
```

```
<213> ORGANISM: Zea mays

<400> SEQUENCE: 252
agtccgctgg ccggtgaagc ac                                              22

<210> SEQ ID NO 253
<211> LENGTH: 37
<212> TYPE: DNA
<213> ORGANISM: Zea mays

<400> SEQUENCE: 253
agtccgctgg ccgaggtcga ctaagccggt gaagcac                              37

<210> SEQ ID NO 254
<211> LENGTH: 24
<212> TYPE: DNA
<213> ORGANISM: Zea mays

<400> SEQUENCE: 254
agtccgctgg ccgaggtgaa gcac                                            24
```